United States Patent
Wiedenmayer et al.

(10) Patent No.: US 12,091,399 B2
(45) Date of Patent: Sep. 17, 2024

(54) PHENYLTETRAZOLE DERIVATIVES AS PLASMA KALLIKREIN INHIBITORS

(71) Applicant: Boehringer Ingelheim International GmbH, Ingelheim am Rhein (DE)

(72) Inventors: Dieter Wiedenmayer, Biberach an der Riss (DE); Andreas Gollner, Vienna (AT); Iain Lingard, Monza (IT); Holger Wagner, Mettenberg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 750 days.

(21) Appl. No.: 17/282,789

(22) PCT Filed: Oct. 7, 2019

(86) PCT No.: PCT/EP2019/077082
§ 371 (c)(1),
(2) Date: Apr. 5, 2021

(87) PCT Pub. No.: WO2020/074442
PCT Pub. Date: Apr. 16, 2020

(65) Prior Publication Data
US 2021/0387963 A1    Dec. 16, 2021

(30) Foreign Application Priority Data

Oct. 10, 2018 (EP) ..................... 18199704

(51) Int. Cl.
| | | |
|---|---|---|
| C07D 401/14 | (2006.01) | |
| C07D 471/08 | (2006.01) | |
| C07D 487/04 | (2006.01) | |
| C07D 487/08 | (2006.01) | |
| C07D 491/048 | (2006.01) | |
| C07D 491/107 | (2006.01) | |
| C07D 498/08 | (2006.01) | |
| A61K 45/06 | (2006.01) | |
| A61P 27/02 | (2006.01) | |
| C07D 403/14 | (2006.01) | |
| C07D 471/04 | (2006.01) | |
| C07D 487/10 | (2006.01) | |
| C07D 491/08 | (2006.01) | |

(52) U.S. Cl.
CPC ......... *C07D 401/14* (2013.01); *C07D 471/08* (2013.01); *C07D 487/04* (2013.01); *C07D 487/08* (2013.01); *C07D 491/048* (2013.01); *C07D 491/107* (2013.01); *C07D 498/08* (2013.01); *A61K 45/06* (2013.01)

(58) Field of Classification Search
CPC .. C07D 401/14; C07D 471/08; C07D 487/04; C07D 487/08; C07D 491/048; C07D 491/107; C07D 498/08; C07D 403/14; C07D 471/04; C07D 487/10; C07D 491/08; A61K 45/06; A61P 27/02
See application file for complete search history.

(56) References Cited

U.S. PATENT DOCUMENTS

| 10,399,961 B2 | 9/2019 | Frattini et al. |
|---|---|---|
| 10,501,440 B2 | 12/2019 | Frattini et al. |
| 10,640,486 B2 | 5/2020 | Frattini et al. |
| 10,695,334 B2 | 6/2020 | Eckhardt et al. |
| 2005/0090529 A1 | 4/2005 | McAlpine et al. |
| 2020/0054617 A1 | 2/2020 | Eckhardt et al. |
| 2021/0276976 A1 | 9/2021 | Eckhardt et al. |
| 2021/0292301 A1 | 9/2021 | Eckhardt et al. |

FOREIGN PATENT DOCUMENTS

| JP | 2005089362 A | 4/2005 |
|---|---|---|
| WO | 2002064545 A1 | 8/2002 |
| WO | 2009097141 A1 | 8/2009 |
| WO | 2013111107 A1 | 8/2013 |
| WO | 2013111108 A1 | 8/2013 |
| WO | 2014188211 A1 | 11/2014 |
| WO | 2017072020 A1 | 5/2017 |

(Continued)

OTHER PUBLICATIONS

Lee BJ, Afshari NA. Advances in drug therapy and delivery for cataract treatment. Curr Opin Ophthalmol. Jan. 1, 2023;34(1):3-8. doi: 10.1097/ICU.0000000000000910. Epub Nov. 14, 2022. PMID: 36484206. (Year: 2023).*
Thrimawithana TR, Rupenthal ID, Räsch SS, Lim JC, Morton JD, Bunt CR. Drug delivery to the lens for the management of cataracts. Adv Drug Deliv Rev. Feb. 15, 2018;126:185-194. doi: 10.1016/j.addr.2018.03.009. Epub Mar. 28, 2018. PMID: 29604375. (Year: 2018).*
International Search Report for PCT/EP2016/075221 mailed Jan. 18, 2017.
Written Opinion for PCT/EP2016/075221 mailed Jan. 18, 2017.
Keener, Plasma Kallikrein and Diabetic Macular Edema, Curr. Diab. Rep. 2010.

(Continued)

*Primary Examiner* — Deepak R Rao
*Assistant Examiner* — Kevin S Martin
(74) *Attorney, Agent, or Firm* — Shelley A. Jones

(57) ABSTRACT

Disclosed are phenyltetrazole derivatives of formula (I),

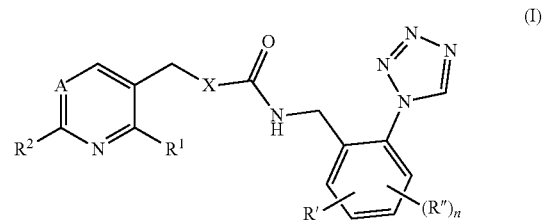

wherein A, $R^1$, $R^2$, X, R', R", and n are as defined herein, and pharmaceutically acceptable salts thereof. Also disclosed are methods of using the phenyltetrazole derivatives for the treatment of diseases which can be influenced by inhibition of plasma kallikrein.

14 Claims, No Drawings

(56) References Cited

FOREIGN PATENT DOCUMENTS

| | | | |
|---|---|---|---|
| WO | 2017072021 A1 | 5/2017 |
| WO | 2017207983 A1 | 12/2017 |
| WO | 2018011628 A1 | 1/2018 |
| WO | 2018192866 A1 | 10/2018 |

OTHER PUBLICATIONS

International Search Report for PCT/EP2016/075222 mailed Oct. 25, 2016.
Written Opinion for PCT/EP2016/075222 mailed Oct. 26, 2016.
International Search Report and Written Opinion for PCT/EP2018059633 mailed Jul. 6, 2018.
Japtap, Heck Reaction, Catalysts, 2017.
Hashiguchi, Asymmetric Transfer Hrydogenation of Aromatic Ketones Catalyzed by Chiral Ruthenium (II) Complexes, J. Am. Chem. Soc, 1995, vol. 117, p. 7562-7563.
Li, Enantioselective, Organocataltyic Reduction of Ketones using Bifunctional Thiorea-Amine Catalysts, Organic Letters, 2010, vol. 12, p. 1756-1759.
Kim, Asymmetric Reductions involving Borohydrides, Organic Research and Development, 2006, vol. 10, p. 949-958.
Nakamura, Recent Developments in asymmetric reduction of ketones with biocatalysts, Tetrahedron: Asymmetry, 2003, vol. 14, p. 2659-2681.
Yoshimura, Recent topics in catalytic asymmetric hydrogenation of ketones, Tetrahedron Letters, 2014, vol. 55, p. 3635-3640.
Biagetti, Synthesis and structure-activity relationship of N-(3-azabicyclo[3.1.0]hex-6-ylmethyl)-5-(2-yridinyl)-1,3-thiazol-2-amines derivatives as NPY Y5 antagonists, Bioorganic & Medicinal Chem Letters, 2010, vol. 20, p. 4741-4744.
International Search Report and Written Opinion for PCT/EP2019/071855 mailed Sep. 1, 2019.
Database Pub Chem, NCBI, No. 8248531, 2014.
InternationalSearch Report for PCT/EP2019/077082 mailed Nov. 13, 2019.
Written Opinion for PCT/EP2019/077082 mailed Nov. 15, 2019.
International Search Report and Written Opinion for PCT/EP2021/053286 mailed May 18, 2021. 15 pgs.
Mormino et al., "Copper-Mediated Perfluoroalkylation of Heteroaryl Bromides with (phen)CuRf", Organic Letters, 2014, vol. 16, No. 6, pp. 1744-1747.
PubChem Substance Record SID 299284535; (2016) 5 pgs.
PubChem Substance Record SID 299284560; (2016) 5 pgs.

* cited by examiner

PHENYLTETRAZOLE DERIVATIVES AS PLASMA KALLIKREIN INHIBITORS

FIELD OF THE INVENTION

This invention relates to novel phenyltetrazole derivatives, and pharmaceutically acceptable salts thereof, that are plasma kallikrein inhibitors. In addition, the invention relates to pharmaceutical compositions and combinations comprising said compounds and to their use in methods for the treatment of diseases which can be influenced by the inhibition of plasma kallikrein. Particularly, the pharmaceutical compositions of the invention are suitable for the prophylaxis and/or therapy of diabetic complications, ocular diseases and edema-associated diseases, in particular diabetic macular edema, age-related macular degeneration, choroidal neovascularization and hereditary angioedema.

BACKGROUND OF THE INVENTION

Plasma kallikrein (PKK) is a trypsin-like serine protease secreted by hepatocytes in the liver as an inactive plasma prekallikrein that circulates in plasma either as a free zymogen or as a heterodimer complex bound to high molecular weight kininogen which is activated to give the active PKK that can liberate kinins from kininogens in addition to processing other substrates. Kinins are potent mediators of inflammation that act through G protein-coupled receptors such as bradykinin receptors.

PKK is thought to play a role in a number of inflammatory disorders and may have numerous implications in disorders such as hereditary angioedema (HAE), retinopathy or diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), choroidal neovascularization (CNV; e.g. non-exudative choroidal neovascularization), posterior vitreous detachment (PVD), ischemic reperfusion injuries, e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, acquired angioedema, drug-related (ACE-inhibitors) edema, high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associated with injury or surgery, brain aneurysm, arterio-venous malformation, reduction of blood losses during surgical procedures (e.g. cardiothoracic surgery, such as cardiopulmonary bypass or coronary artery bypass grafting), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), cerebral hemorrhage, deep vein thrombosis, coagulation from post fibrinolytic treatments, angina, angioedema, sepsis, arthritis (e.g. rheumatoid arthritis, osteoarthritis, infection arthritis), lupus, gout, psoriasis, inflammatory bowel, diabetes, diabetic complications, complications arising from metabolic syndrome, infectious diseases, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma), allergic edema e.g. airflow obstruction in chronic allergic sinusitis or perennial rhinitis; airflow obstruction in acute asthma; serositis associated with systemic lupus erythematosus (SLE), acute respiratory distress syndrome (ARDS) and other diseases.

PKK inhibitors are considered to be useful in the treatment of a wide range of disorders, particularly in the treatment of edema formation in diseases, e.g. edema formation related to ischemic reperfusion injuries, retinopathy or edema-associated diseases, such as hereditary angioedema, macular edema and brain edema. PKK inhibitors are considered to be especially useful in the treatment of retinopathy, e.g. retinopathy associated with diabetes and/or hypertension, and in the treatment of macular edema, e.g. macular edema associated with diabetes and/or hypertension.

PKK inhibitors suitable for therapeutic use should bind potently and with high selectivity to PKK. They should be well absorbed from the gastrointestinal tract, be sufficiently metabolically stable and possess favorable pharmacokinetic properties. They should be non-toxic and demonstrate few side-effects.

The compounds of the invention are PKK inhibitors and are therefore potentially useful in the treatment of disorders mentioned hereinbefore, particularly should have utility as a treatment to reduce retinal vascular permeability associated with diabetic retinopathy and diabetic macular edema retinopathy or edema-associated diseases. Other complications of diabetes such as cerebral haemorrhage, nephropathy, cardiomyopathy and neuropathy, all of which have associations with PKK may also be considered as targets for a PKK inhibitor.

Low molecular weight plasma kallikrein inhibitors are known in the art, for example, the compounds disclosed in WO 2013/111108, WO 2013/111107, WO 2014/188211, WO 2017/072020, and WO 2017/072021.

SUMMARY OF THE INVENTION

In a first aspect, the present invention relates to a compound of formula (I)

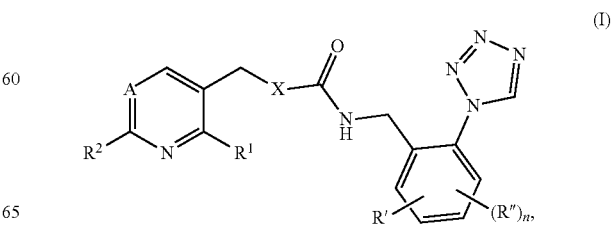

wherein

A is selected from the group A-G1 consisting of N, CH, C—F, C—Cl, C—Br, C—CN, and C—CH$_3$;

R$^1$ is selected from the group R$^1$-G1 consisting of H and C$_{1-3}$-alkyl optionally substituted with 1 to 3 F;

R$^2$ is selected from the group R$^2$-G1 consisting of
saturated 6-12-membered bicyclic ring systems containing 1 to 3 N atoms as ring members and optionally 1 to 2 ring members selected from the group consisting of C═O, O, S, S═O, and SO$_2$,
provided that the ring systems do not contain any heteroatom-heteroatom bonds between ring members,
wherein said ring systems are attached to the heteroaromatic ring in formula (I) via an N atom, and
wherein said ring systems are optionally substituted with 1 to 6 F, optionally substituted with 1 substituent R$^3$, and optionally substituted with 1 or 2 CH$_3$ groups;

X is selected from the group X-G1 consisting of
5-membered heteroaryls containing 1 to 3 N atoms, and
9-membered heteroaryls consisting of a 5-membered ring fused to a 6-membered ring and containing 1 to 3 N atoms,
wherein said heteroaryls are attached to the carbonyl group in formula (I) via a C atom of the 5-membered ring and to the CH$_2$ group in formula (I) via a non-adjacent C or N atom of the 5-membered ring, and
wherein said heteroaryls are optionally substituted with 1 substituent R$^4$;

R$^3$ is selected from the group R$^3$-G1 consisting of
C$_{1-3}$-alkyl, C$_{1-3}$-alkylene-OH, C$_{1-3}$-alkylene-O—CH$_3$, —CN, —NH$_2$, —OH, and —O—C$_{1-3}$-alkyl;

R$^4$ is selected from the group R$^4$-G1 consisting of
F, Cl, Br, C$_{1-3}$-alkyl, C$_{1-3}$-alkylene-OH, C$_{1-3}$-alkylene-O—CH$_3$, —CN, —NH$_2$, —OH, —O—C$_{1-3}$-alkyl, and 5-membered heteroaryls containing 1 —NH—, —N<, —O—, or —S— ring member and optionally additionally 1 or 2 ═N— ring members and being optionally substituted with 1 or 2 CH$_3$ groups, wherein said C$_{1-3}$-alkyl group is optionally substituted with 1 to 3 F;

R' is selected from the group R'-G1 consisting of
F, Cl, C$_{1-3}$-alkyl, C$_{3-4}$-cycloalkyl, —CN, —O—C$_{1-3}$-alkyl, and —SO$_2$—C$_{1-3}$-alkyl, wherein said C$_{1-3}$-alkyl and —O—C$_{1-3}$-alkyl groups are optionally substituted with 1 to 3 F;

R" is at each occurrence independently selected from the group R"-G1 consisting of F, Cl, and CH$_3$; and n is an integer selected from the group n-G1 consisting of 0, 1, and 2;

wherein in any definition mentioned hereinbefore and if not specified otherwise, any alkyl or alkylene group or subgroup may be straight-chained or branched, the isoforms, tautomers, stereoisomers, metabolites, prodrugs, solvates, hydrates, and the salts thereof, particularly the pharmaceutically acceptable salts thereof, or the combinations thereof.

In a second aspect, the present invention relates to a pharmaceutical composition comprising one or more compounds of formula (I), as defined hereinbefore or hereinafter, or pharmaceutically acceptable salts thereof, optionally together with one or more inert carriers and/or diluents.

In a third aspect, the present invention relates to a pharmaceutical composition comprising one or more compounds of formula (I), as defined hereinbefore or hereinafter, or pharmaceutically acceptable salts thereof, and one or more additional therapeutic agents, optionally together with one or more inert carriers and/or diluents.

In a fourth aspect, the present invention relates to a compound of formula (I), as defined hereinbefore or hereinafter, or a pharmaceutically acceptable salt thereof for use as a medicament.

In a fifth aspect, the present invention relates to a method for the treatment of diseases or conditions which can be influenced by the inhibition of plasma kallikrein in a patient in need thereof, the method being characterized in that one or more compounds of formula (I), as defined hereinbefore or hereinafter, or pharmaceutically acceptable salts thereof are administered to the patient.

Also, the present invention relates to the use of one or more compounds of formula (I), as defined hereinbefore or hereinafter, in the manufacture of a medicament for the treatment of diseases or conditions which can be influenced by the inhibition of plasma kallikrein.

Also, the present invention relates to a compound of formula (I), as defined hereinbefore or hereinafter, or a pharmaceutically acceptable salt thereof for use in a method for the treatment of diseases or conditions which can be influenced by the inhibition of plasma kallikrein, in a patient in need thereof.

Further aspects of the present invention will become apparent to the person skilled in the art directly from the foregoing and following description and the examples.

General Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

Also, unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, EtOAc, EtOH, isopropanol, or ACN, or a mixture thereof.

Salts of other acids than those mentioned above which for example are useful for purifying or isolating the compounds of the present invention (e.g. trifluoro acetate salts) also comprise a part of the invention.

In case a compound of the present invention is depicted in form of a chemical name and as a formula in case of any discrepancy the formula shall prevail.

In the groups, radicals, or moieties defined below, the number of carbon atoms is often specified preceding the group, for example, $C_{1-6}$-alkyl means an alkyl group or radical having 1 to 6 carbon atoms.

An asterisk may be used in sub-formulas to indicate the bond which is connected to the core molecule as defined or to a substituent. In the case of more than one attachment point, i.e. more than one asterisk, in a sub-formula, the asterisks may be further specified by a bracketed designation of the connected part of the core molecule or the substituent.

The numeration of the atoms of a substituent starts with the atom which is closest to the core or to the group to which the substituent is attached.

For example, the term "3-carboxypropyl-group" represents the following substituent:

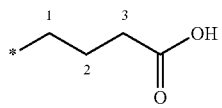

wherein the carboxy group is attached to the third carbon atom of the propyl group. The terms "1-methylpropyl-", "2,2-dimethylpropyl-" or "cyclopropylmethyl-" group represent the following groups:

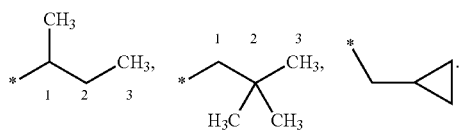

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In a definition of a group, the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkylene or $C_{1-3}$-alkyl-O—, wherein each alkyl and alkylene group is optionally substituted with one or more $L^{ex}$." or the like means that in each of the beforementioned groups which comprise the term alkyl or alkylene, i.e. in each of the groups $C_{1-3}$-alkyl, $C_{3-6}$-cycloalkyl-$C_{1-3}$-alkylene and $C_{1-3}$-alkyl-O—, the alkyl and alkylene moiety may be substituted with $L^{ex}$ as defined.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-n}$ alkylene" wherein n is an integer selected from 2, 3, 4, 5 or 6, preferably 4 or 6, either alone or in combination with another radical, denotes an acyclic, straight or branched chain divalent alkyl radical containing from 1 to n carbon atoms. For example the term $C_{1-4}$-alkylene includes —CH$_2$—, —CH$_2$—CH$_2$—, —CH(CH$_3$)—, —CH$_2$—CH$_2$—CH$_2$—, —C(CH$_3$)$_2$—, —CH(CH$_2$CH$_3$)—, —CH(CH$_3$)—CH$_2$—, —CH$_2$—CH(CH$_3$)—, —CH$_2$—CH$_2$—CH$_2$—CH$_2$—, —CH$_2$—CH$_2$—CH(CH$_3$)—, —CH(CH$_3$)—CH$_2$—CH$_2$—, —CH$_2$—CH(CH$_3$)—CH$_2$—, —CH$_2$—C(CH$_3$)$_2$—, —C(CH$_3$)$_2$—CH$_2$—, —CH(CH$_3$)—CH(CH$_3$)—, —CH$_2$—CH(CH$_2$CH$_3$)—, —CH(CH$_2$CH$_3$)—CH$_2$—, —CH(CH$_2$CH$_2$CH$_3$)—, —CH(CH(CH$_3$))$_2$— and —C(CH$_3$)(CH$_2$CH$_3$)—.

The term "$C_{3-n}$-cycloalkyl", wherein n is an integer 3 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclo-pentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "aryl" as used herein, either alone or in combination with another radical, denotes a carbocyclic aromatic monocyclic group containing 6 carbon atoms which is optionally further fused to a second five- or six-membered, carbocyclic group which is optionally aromatic, saturated or unsaturated. The term "aryl" includes, but is not limited to, phenyl, indanyl, indenyl, naphthyl, anthracenyl, phenanthrenyl, tetrahydronaphthyl and dihydronaphthyl.

The term "heteroaryl" means a mono- or polycyclic aromatic ring system containing one or more heteroatoms selected from N, O or S(O)$_r$, wherein r=0, 1 or 2, consisting of 5 to 14 ring atoms wherein at least one of the heteroatoms is part of an aromatic ring. The term "heteroaryl" is intended to include all the possible isomeric forms.

Thus, the term "heteroaryl" includes the following exemplary structures; they are not depicted as radicals as each form is optionally attached through a covalent bond to any atom so long as appropriate valences are maintained:

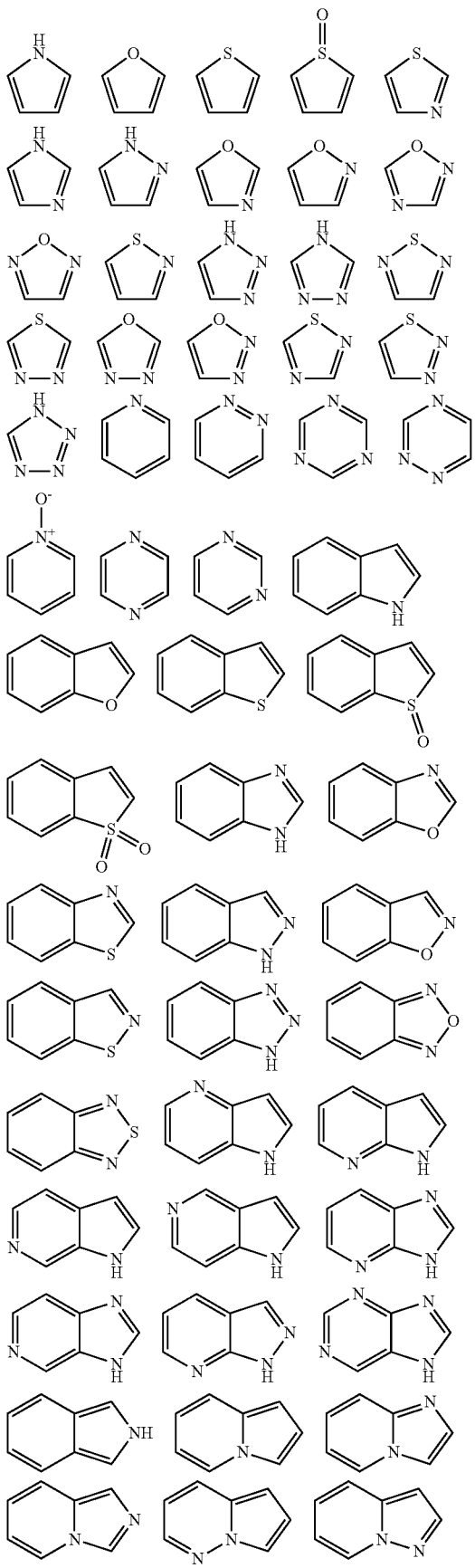

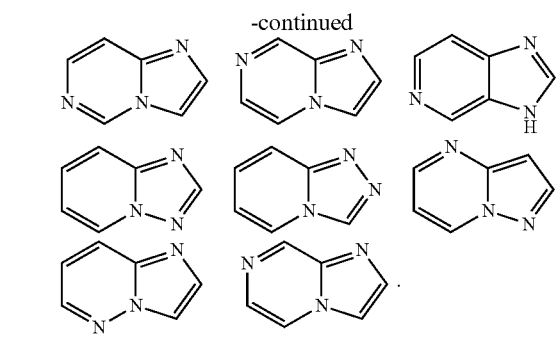

The term "bicyclic ring systems" means groups consisting of 2 joined cyclic substructures including spirocyclic, fused, and bridged ring systems.

The term halogen generally denotes fluorine, chlorine, bromine and iodine.

Many of the terms given above may be used repeatedly in the definition of a formula or group and in each case have one of the meanings given above, independently of one another.

The terms "treatment" and "treating" as used herein embrace both therapeutic, i.e. curative and/or palliative, and preventive, i.e. prophylactic, treatment.

Therapeutic treatment refers to the treatment of patients having already developed one or more of said conditions in manifest, acute or chronic form. Therapeutic treatment may be symptomatic treatment in order to relieve the symptoms of the specific indication or causal treatment in order to reverse or partially reverse the conditions of the indication or to stop or slow down progression of the disease.

Preventive treatment ("prevention") refers to the treatment of patients at risk of developing one or more of said conditions, prior to the clinical onset of the disease in order to reduce said risk.

The terms "treatment" and "treating" include the administration of one or more active compounds in order to prevent or delay the onset of the symptoms or complications and to prevent or delay the development of the disease, condition or disorder and/or in order to eliminate or control the disease, condition or disorder as well as to alleviate the symptoms or complications associated with the disease, condition or disorder.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

Abbreviations

Ac acetyl
ACN acetonitrile
AMC 7-amino-4-methylcoumarin
Boc tert-butyloxycarbonyl
BSA bovine serum albumin
Bzl benzyl
d day(s)
DAD diode array detector
DBAD di-tert-butyl azodicarboxylate DBU 1,8-diazabicyclo[5.4.0]undec-7-ene
DCM dichloromethane
DEAD diethyl azodicarboxylate
DIAD diisopropyl azodicarboxylate
DMEM Dulbecco's modified eagle medium
DMF N,N-dimethylformamide
DMSO dimethyl sulfoxide
EDTA ethylenediaminetetraacetate
ESI electrospray ionization (in MS)
EtOAc ethyl acetate
EtOH ethanol
h hour(s)
HATU O-(7-azabenzotriazol-1-yl)-N,N,N',N'-tetramethyluronium-hexafluorophosphate
HPLC high performance liquid chromatography
HPLC-MS coupled high performance liquid chromatography-mass spectrometry
LC liquid chromatography
LC-MS coupled liquid chromatography-mass spectrometry
LG leaving group
M molar (mol/L)
MeOH methanol
min minute(s)
MS mass spectrometry
NADPH nicotinamide adenine dinucleotide phosphate
NMR nuclear magnetic resonance
PET polyethylene terephthalate
PyBop (benzotriazol-1-yloxy)tripyrrolidinophosphonium hexafluorophosphate
Rf retardation factor (TLC)
RFU relative fluorescence units
RP reverse phase
rt room temperature
$t_R$ retention time (in HPLC/LC)
TBTU O-(benzotriazol-1-yl)-N,N,N',N'-tetramethyluronium tetrafluoroborate
TFA trifluoroacetic acid
THF tetrahydrofuran
TLC thin layer chromatography
UV ultraviolet

DETAILED DESCRIPTION OF THE INVENTION

The present invention discloses novel phenyltetrazole derivatives, which are effective plasma kallikrein (PKK) inhibitors and possess suitable pharmacological and pharmacokinetic properties to use them as medicaments for the treatment of diseases and/or conditions that may be influenced by PKK inhibition, including but not limited to diabetic complications, ocular diseases and edema-associated diseases, in particular diabetic macular edema, age-related macular degeneration, choroidal neovascularization and hereditary angioedema.

The compounds of the present invention may provide several advantages, such as enhanced potency, high metabolic and/or chemical stability, high selectivity, safety and tolerability, enhanced solubility, enhanced permeability, desirable plasma protein binding, enhanced bioavailability, improved pharmacokinetic profiles, and the possibility to form stable salts.

COMPOUNDS OF THE INVENTION

In a first aspect of the present invention, it is found that compounds of formula (I)

(I)

wherein A, $R^1$, $R^2$, X, R', R", and n are defined as hereinbefore and hereinafter, are potent inhibitors of PKK and exhibit favorable properties with regard to selectivity, safety and tolerability, metabolic and/or chemical stability, pharmacokinetic and physicochemical characteristics, solubility, permeability, plasma protein binding, bioavailability and the possibility to form stable salts. In particular, they provide an advantageous combination of high potency on human PKK, significant selectivity, e.g. vs. various serine proteases, such as human tissue kallikrein 1 (TK1), and safety features, such as low potential of mutagenicity and low propensity for mechanism based inhibition of cytochrom P450 3A4.

Therefore, the compounds of formula (I), as defined hereinbefore or hereinafter, or pharmaceutically acceptable salts thereof are expected to be useful in the treatment of diseases and/or conditions which can be influenced by PKK inhibition.

Thus, according to one aspect of the present invention, a compound of formula (I)

(I)

wherein A, $R^1$, $R^2$, X, R', R", and n are defined as hereinbefore or hereinafter, is provided as well as the isomers, tautomers, stereoisomers, metabolites, prodrugs, solvates, hydrates, and the salts thereof, particularly the pharmaceutically acceptable salts thereof.

Unless otherwise stated, the groups, residues and substituents, particularly A, $R^1$, $R^2$, X, $R^3$, $R^4$, R', R", and n are defined as hereinbefore and hereinafter. Some preferred meanings of the substituents A, $R^1$, $R^2$, X, $R^3$, $R^4$, R', R", and n will be given hereinafter as embodiments of the invention. Any and each of these definitions and embodiments may be combined with one another.

A:

According to one embodiment, A is selected from the group A-G1 consisting of N, CH, C—F, C—Cl, C—Br, C—CN, and C—CH₃.

According to another embodiment, A is selected from the group A-G2 consisting of N, CH and C—Br.

According to another embodiment, A is selected from the group A-G3 consisting of N.

According to another embodiment, A is selected from the group A-G4 consisting of CH.

According to another embodiment, A is selected from the group A-G5 consisting of C—Br.

R¹:

According to one embodiment, R¹ is selected from the group R¹-G1 consisting of H and $C_{1-3}$-alkyl optionally substituted with 1 to 3 F.

According to another embodiment, R¹ is selected from the group R¹-G2 consisting of H and $CH_3$.

According to another embodiment, R¹ is selected from the group R¹-G3 consisting of H.

According to another embodiment, R¹ is selected from the group R¹-G4 consisting of $CH_3$.

R²:

According to one embodiment, R² is selected from the group R²-G1 consisting of
saturated 6-12-membered bicyclic ring systems containing 1 to 3 N atoms as ring members and optionally 1 to 2 ring members selected from the group consisting of C=O, O, S, S=O, and $SO_2$,
provided that the ring systems do not contain any heteroatom-heteroatom bonds between ring members,
wherein said ring systems are attached to the heteroaromatic ring in formula (I) via an N atom, and
wherein said ring systems are optionally substituted with 1 to 6 F, optionally substituted with 1 substituent R³, and optionally substituted with 1 or 2 $CH_3$ groups.

According to another embodiment, R² is selected from the group R²-G2 consisting of saturated 6-10-membered bicyclic ring systems containing 1 to 2 N atoms as ring members and optionally 1 ring member selected from the group consisting of C=O and O,
provided that the ring systems do not contain any heteroatom-heteroatom bonds between ring members,
wherein said ring systems are attached to the heteroaromatic ring in formula (I) via an N atom, and
wherein said ring systems are optionally substituted with 1 or 2 F, optionally substituted with 1 substituent R³, and optionally substituted with 1 $CH_3$ group.

According to another embodiment, R² is selected from the group R²-G3 consisting of

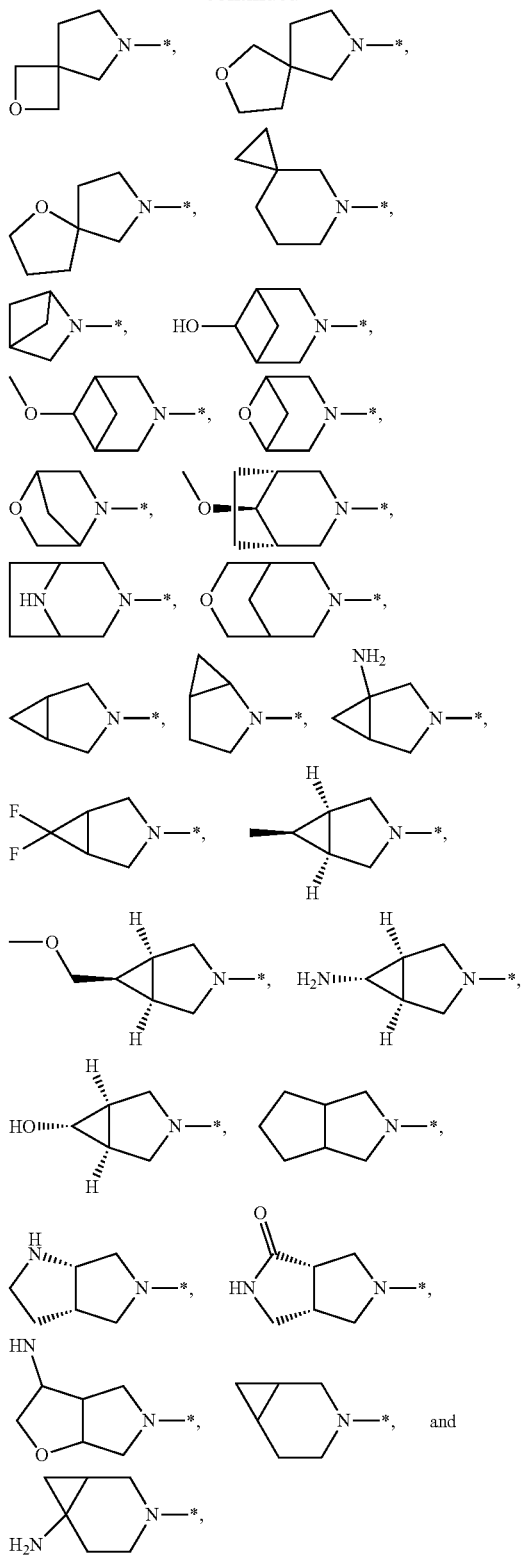

wherein, as indicated by the asterisk, the ring system is attached to the heteroaromatic ring in formula (I) via the N atom.

According to another embodiment, R² is selected from the group R²-G4 consisting of According to another embodiment, R² is selected from the group R²-G5 consisting of [structures shown].

According to another embodiment, R² is selected from the group R²-G6 consisting of [structures shown].

According to another embodiment, R² is selected from the group R²-G7 consisting of [structures shown].

According to another embodiment, R² is selected from the group R²-G8 consisting of [structure shown].

According to another embodiment, R² is selected from the group R²-G9 consisting of [structures shown].

According to another embodiment, R² is selected from the group R²-G10 consisting of [structures shown].

X:

According to one embodiment, X is selected from the group X-G1 consisting of
5-membered heteroaryls containing 1 to 3 N atoms, and
9-membered heteroaryls consisting of a 5-membered ring fused to a 6-membered ring and containing 1 to 3 N atoms, wherein said heteroaryls are attached to the carbonyl group in formula (I) via a C atom of the 5-membered ring and to the CH₂ group in formula (I) via a non-adjacent C or N atom of the 5-membered ring, and wherein said heteroaryls are optionally substituted with 1 substituent $R^4$.

According to another embodiment, X is selected from the group X-G2 consisting of

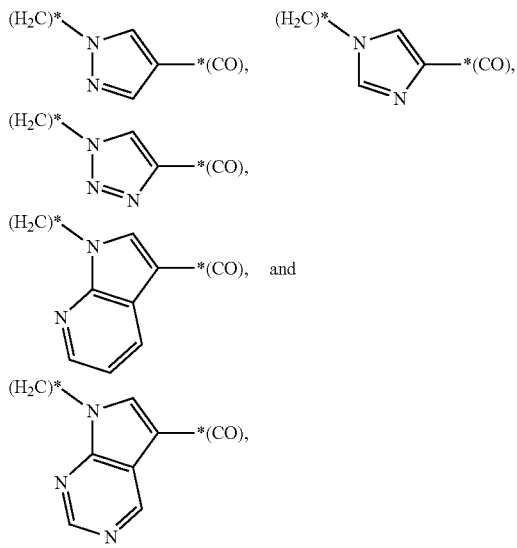

each of which is optionally substituted with 1 substituent $R^4$ and
wherein the bonds with asterisk and brackets indicate the sites of attachment of the groups C=O and $CH_2$ of formula (I).

According to another embodiment, X is selected from the group X-G3 consisting of

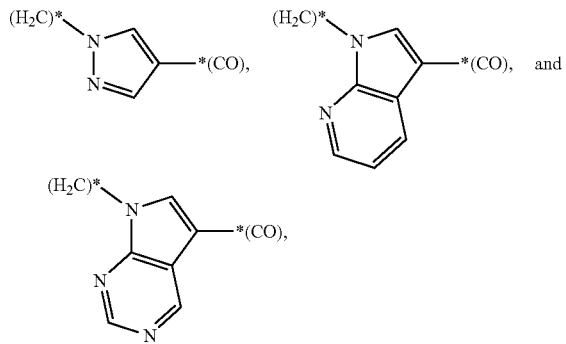

each of which is optionally substituted with 1 substituent $R^4$ and
wherein the bonds with asterisk and brackets indicate the sites of attachment of the groups C=O and $CH_2$ of formula (I).

According to another embodiment, X is selected from the group X-G4 consisting of

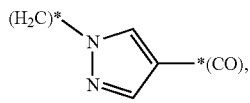

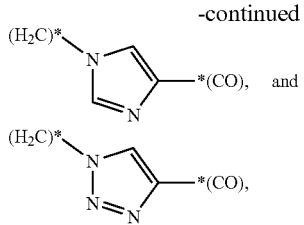

each of which is optionally substituted with 1 substituent $R^4$ and
wherein the bonds with asterisk and brackets indicate the sites of attachment of the groups C=O and $CH_2$ of formula (I).

According to another embodiment, X is selected from the group X-G5 consisting of

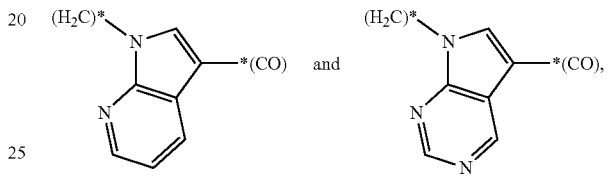

each of which is optionally substituted with 1 substituent $R^4$ and
wherein the bonds with asterisk and brackets indicate the sites of attachment of the groups C=O and $CH_2$ of formula (I).

According to another embodiment, X is selected from the group X-G6 consisting of

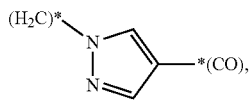

which is optionally substituted with 1 substituent $R^4$ and
wherein the bonds with asterisk and brackets indicate the sites of attachment of the groups C=O and $CH_2$ of formula (I).

According to another embodiment, X is selected from the group X-G7 consisting of

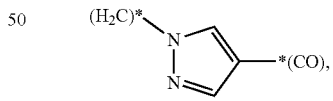

which is optionally substituted with 1 substituent $R^4$ at the C atom adjacent to the —N= atom and
wherein the bonds with asterisk and brackets indicate the sites of attachment of the groups C=O and $CH_2$ of formula (I).

$R^3$:

According to one embodiment, $R^3$ is selected from the group $R^3$-G1 consisting of $C_{1-3}$-alkyl, $C_{1-3}$-alkylene-OH, $C_{1-3}$-alkylene-O—$CH_3$, —CN, —$NH_2$, —OH, and —O—$C_{1-3}$-alkyl.

According to another embodiment, $R^3$ is selected from the group $R^3$-G2 consisting of $CH_3$, $CH(CH_3)_2$, $CH_2$—$OCH_3$, $NH_2$, —OH, and —O—$CH_3$.

According to another embodiment, $R^3$ is selected from the group $R^3$-G3 consisting of $CH_3$ and $CH(CH_3)_2$.

According to another embodiment, $R^3$ is selected from the group $R^3$-G4 consisting of $CH_2$—$OCH_3$ and —O—$CH_3$.

According to another embodiment, $R^3$ is selected from the group $R^3$-G5 consisting of $NH_2$ and —OH.

$R^4$:

According to one embodiment, $R^4$ is selected from the group $R^4$-G1 consisting of F, Cl, Br, $C_{1-3}$-alkyl, $C_{1-3}$-alkylene-OH, $C_{1-3}$-alkylene-O—$CH_3$, —CN, —$NH_2$, —OH, —O—$C_{1-3}$-alkyl, and 5-membered heteroaryls containing 1 —NH—, —N<, —O—, or —S— ring member and optionally additionally 1 or 2 =N— ring members and being optionally substituted with 1 or 2 $CH_3$ groups, wherein said $C_{1-3}$-alkyl group is optionally substituted with 1 to 3 F.

According to one embodiment, $R^4$ is selected from the group $R^4$-G2 consisting of F, Cl, Br, $C_{1-3}$-alkyl, $C_{1-3}$-alkylene-OH, $C_{1-3}$-alkylene-O—$CH_3$, —CN, —$NH_2$, —OH, —O—$C_{1-3}$-alkyl, and 5-membered heteroaryls containing 1 —NH— or, —N< ring member and optionally additionally 1 or 2 =N— ring members and being optionally substituted with 1 or 2 $CH_3$ groups, wherein said $C_{1-3}$-alkyl group is optionally substituted with 1 to 3 F.

According to another embodiment, $R^4$ is selected from the group $R^4$-G3 consisting of Cl, Br, $C_{1-3}$-alkyl, $C_{1-3}$-alkylene-O—$CH_3$, —$NH_2$, —O—$CH_3$, and 5-membered heteroaryls containing 1 —NH— ring member and optionally additionally 1 or 2 =N— ring members and being optionally substituted with 1 $CH_3$ group, wherein said $C_{1-3}$-alkyl group is optionally substituted with 1 to 3 F.

According to another embodiment, $R^4$ is selected from the group $R^4$-G4 consisting of Cl, Br, $CH_3$, $CHF_2$, $CH_2$—O—$CH_3$, $NH_2$, O—$CH_3$, and N-methyl-pyrazol-4-yl.

According to another embodiment, $R^4$ is selected from the group $R^4$-G5 consisting of Cl and Br.

According to another embodiment, $R^4$ is selected from the group $R^4$-G6 consisting of $CH_3$ and $CHF_2$.

According to another embodiment, $R^4$ is selected from the group $R^4$-G7 consisting of $CH_2$—O—$CH_3$ and O—$CH_3$.

According to another embodiment, $R^4$ is selected from the group $R^4$-G8 consisting of $NH_2$.

According to another embodiment, $R^4$ is selected from the group $R^4$-G9 consisting of N-methyl-pyrazol-4-yl.

R':

According to one embodiment, R' is selected from the group R'-G1 consisting of F, Cl, $C_{1-3}$-alkyl, $C_{3-4}$-cycloalkyl, —CN, —O—$C_{1-3}$-alkyl, and —$SO_2$—$C_{1-3}$-alkyl, wherein said $C_{1-3}$-alkyl and —O—$C_{1-3}$-alkyl groups are optionally substituted with 1 to 3 F.

According to another embodiment, R' is selected from the group R'-G2 consisting of F, Cl, $C_{1-3}$-alkyl, $CHF_2$, $CF_3$, cyclopropyl, $C_{1-3}$-alkylene-OH, $C_{1-3}$-alkylene-O—$CH_3$, —CN, —OH, —O—$CH_3$, —O—$CHF_2$, O—$CF_3$, and —$SO_2$—$CH_3$.

According to another embodiment, R' is selected from the group R'-G3 consisting of F, Cl, $CH_3$, $CHF_2$, $CF_3$, and —CN.

According to another embodiment, R' is selected from the group R'-G4 consisting of F, Cl, and $CH_3$.

According to another embodiment, R' is selected from the group R'-G5 consisting of F.

According to another embodiment, R' is selected from the group R'-G6 consisting of Cl.

According to another embodiment, R' is selected from the group R'-G7 consisting of $CH_3$.

R":

According to one embodiment, R" is at each occurrence independently selected from the group R"-G1 consisting of F, Cl, and $CH_3$.

According to another embodiment, R" is selected from the group R"-G2 consisting of F.

According to another embodiment, R" is selected from the group R"-G3 consisting of Cl.

According to another embodiment, R" is selected from the group R"-G4 consisting of $CH_3$.

n:

According to one embodiment, n is an integer selected from the group n-G1 consisting of 0, 1, and 2.

According to another embodiment, n is an integer selected from the group n-G2 consisting of 0 and 1.

According to another embodiment, n is an integer selected from the group n-G3, consisting of 0.

According to another embodiment, n is an integer selected from the group n-G4, consisting of 1.

Further preferred subgeneric embodiments of the compounds of formula (I) are set forth as embodiments (I-a) to (I-q) in the following Table 1, wherein the above-mentioned substituent definitions are used. For example, the entry -G1 in column $R^1$ and row (I-a) means that in embodiment (I-a) substituent $R^1$ is selected from the definition designated $R^1$-G1. The same applies analogously to the other variables incorporated in the general formulas.

TABLE 1

| Embodiment | A | $R^1$ | $R^2$ | X | $R^3$ | $R^4$ | R' | R" | n |
|---|---|---|---|---|---|---|---|---|---|
| (I-a) | A-G1 | $R^1$-G1 | $R^2$-G1 | X-G1 | $R^3$-G1 | $R^4$-G2 | R'-G2 | R"-G1 | n-G1 |
| (I-b) | A-G1 | $R^1$-G1 | $R^2$-G2 | X-G2 | $R^3$-G1 | $R^4$-G2 | R'-G2 | R"-G1 | n-G1 |
| (I-c) | A-G1 | $R^1$-G1 | $R^2$-G2 | X-G2 | $R^3$-G1 | $R^4$-G3 | R'-G3 | R"-G1 | n-G1 |
| (I-d) | A-G1 | $R^1$-G1 | $R^2$-G2 | X-G2 | $R^3$-G2 | $R^4$-G3 | R'-G3 | R"-G1 | n-G1 |
| (I-e) | A-G2 | $R^1$-G1 | $R^2$-G2 | X-G2 | $R^3$-G2 | $R^4$-G3 | R'-G3 | R"-G1 | n-G1 |
| (I-f) | A-G2 | $R^1$-G2 | $R^2$-G2 | X-G2 | $R^3$-G2 | $R^4$-G3 | R'-G3 | R"-G1 | n-G1 |
| (I-g) | A-G2 | $R^1$-G2 | $R^2$-G3 | X-G2 | — | $R^4$-G4 | R'-G3 | R"-G1 | n-G1 |
| (I-h) | A-G2 | $R^1$-G2 | $R^2$-G3 | X-G3 | — | $R^4$-G4 | R'-G3 | R"-G1 | n-G1 |
| (I-i) | A-G2 | $R^1$-G2 | $R^2$-G3 | X-G3 | — | $R^4$-G4 | R'-G4 | R"-G1 | n-G2 |
| (I-j) | A-G3 | $R^1$-G4 | $R^2$-G4 | X-G4 | — | $R^4$-G6 | R'-G6 | R"-G2 | n-G2 |
| (I-k) | A-G3 | $R^1$-G4 | $R^2$-G4 | X-G4 | — | $R^4$-G7 | R'-G6 | R"-G2 | n-G2 |
| (I-l) | A-G3 | $R^1$-G4 | $R^2$-G7 | X-G4 | — | $R^4$-G6 | R'-G6 | R"-G2 | n-G2 |
| (I-m) | A-G3 | $R^1$-G4 | $R^2$-G7 | X-G4 | — | $R^4$-G7 | R'-G6 | R"-G2 | n-G2 |
| (I-n) | A-G4 | $R^1$-G4 | $R^2$-G4 | X-G4 | — | $R^4$-G6 | R'-G6 | R"-G2 | n-G2 |
| (I-o) | A-G4 | $R^1$-G4 | $R^2$-G4 | X-G4 | — | $R^4$-G7 | R'-G6 | R"-G2 | n-G2 |
| (I-p) | A-G3 | $R^1$-G4 | $R^2$-G7 | X-G5 | — | $R^4$-G6 | R'-G6 | R"-G2 | n-G2 |

TABLE 1-continued

| | | | Substituents | | | | | |
|---|---|---|---|---|---|---|---|---|
| Embodiment | A | $R^1$ | $R^2$ | X | $R^3$ | $R^4$ | R' | R" | n |
| (I-q) | A-G4 | $R^1$-G4 | $R^2$-G7 | X-G5 | — | $R^4$-G6 | R'-G6 | R"-G2 | n-G2 |
| (I-r) | A-G4 | $R^1$-G4 | $R^2$-G7 | X-G6 | | $R^4$-G6 | R'-G6 | R"-G2 | n-G2 |
| (I-s) | A-G4 | $R^1$-G4 | $R^2$-G7 | X-G6 | | $R^4$-G7 | R'-G6 | R"-G2 | n-G2 |
| (I-t) | A-G4 | $R^1$-G4 | $R^2$-G7 | X-G7 | | $R^4$-G5 | R'-G6 | R"-G2 | n-G2 |
| (I-u) | A-G4 | $R^1$-G2 | $R^2$-G7 | X-G7 | | $R^4$-G8 | R'-G6 | R"-G2 | n-G2 |
| (I-v) | A-G4 | $R^1$-G2 | $R^2$-G7 | X-G7 | | $R^4$-G9 | R'-G6 | R"-G2 | n-G2 |
| (I-w) | A-G5 | $R^1$-G3 | $R^2$-G7 | X-G6 | | $R^4$-G6 | R'-G6 | R"-G2 | n-G2 |

Particularly preferred compounds, including their tautomers, the salts thereof, or any solvates or hydrates thereof, are those described in the section Examples and Experimental Data.

Preparation

The compounds according to the invention and their intermediates may be obtained using methods of synthesis which are known to the one skilled in the art and described in the literature of organic synthesis for example using methods described in "Comprehensive Organic Transformations", 2$^{nd}$ Edition, Richard C. Larock, John Wiley & Sons, 2010, and "March's Advanced Organic Chemistry", 7th Edition, Michael B. Smith, John Wiley & Sons, 2013. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out, any corresponding functional groups in the starting compounds may be protected using conventional protecting groups. These protecting groups may be cleaved again at a suitable stage within the reaction sequence using methods familiar to the skilled man and described in the literature for example in "Protecting Groups", 3$^{rd}$ Edition, Philip J. Kocienski, Thieme, 2005, and "Protective Groups in Organic Synthesis", 4$^{th}$ Edition, Peter G. M. Wuts, Theodora W. Greene, John Wiley & Sons, 2006.

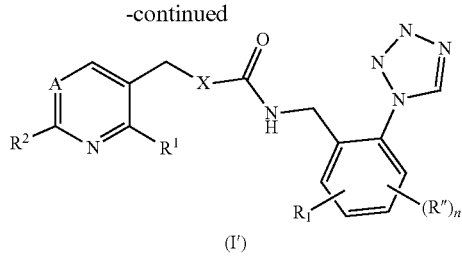

(I')

Scheme 1: Compounds of formula (I') can be prepared by reaction of a suitable acid of formula (II) (either as free acid or carboxylate with a suitable metal cation such as Li$^+$, Na$^+$, K$^+$, etc.) and a suitable amine of formula (III) (either as free amine or a salt such as hydrochloride, hydrobromide, etc.) in a suitable solvent (e.g., DCM, THF, 1,4-dioxane, DMF, N,N-dimethylacetamide, and 1-methyl-2-pyrrolidinone) in the presence of a suitable coupling agent (e.g., O-(7-azabenzotriazol-1-yl)-N,N,N',N'-tetramethyluronium-hexafluoro-phosphate (HATU), O-(benzotriazol-1-yl)-N,N,N',N'-tetramethyluronium tetrafluoroborate (TBTU), (benzotriazol-1-yloxy)tripyrrolidinophosphonium hexafluorophosphate (PyBOP), carbodiimide reagents, etc.) and a base (e.g., triethylamine, N,N-diisopropyl-ethylamine, pyridine, etc.) to form an amide bond; A, $R^1$, $R^2$, X, R', R", and n in Scheme 1 have the meanings as defined hereinbefore. Alternatively, the carboxylic acid is transformed into a carboxylic chloride (using, e.g., oxalyl chloride or thionyl chloride in DCM) and coupled as such with amine (III) in the presence of a suited base (e.g., triethylamine, N,N-diisopropyl-ethylamine, pyridine, etc.).

Scheme 1

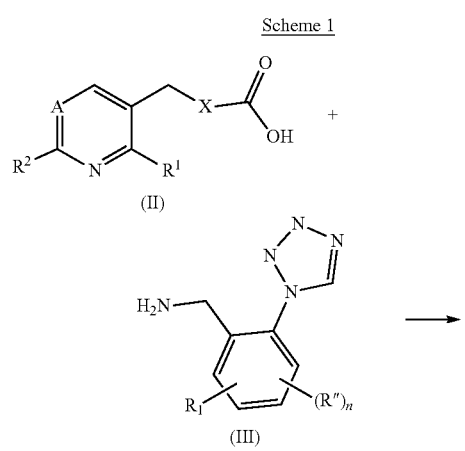

Scheme 2

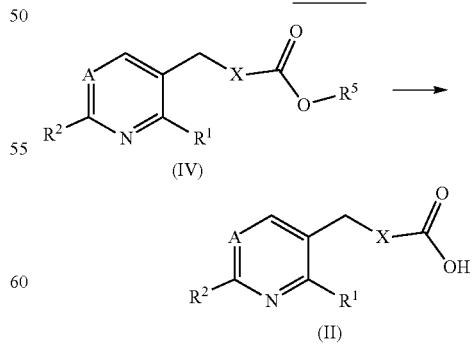

$R^5 = C_{1-4}$-alkyl, benzyl

Scheme 2: Acids of formula (II), wherein A, $R^1$, $R^2$, and X have the meanings as defined hereinbefore, are preferably prepared from the corresponding ester (IV) through hydrolysis or hydrogenolysis depending on the nature of $R^5$. Lower alkyl group esters such as ethyl or methyl esters are preferably cleaved by hydrolysis with a hydroxide salt such as NaOH, LiOH, or KOH in a mixture of water and a suitable miscible solvent (e.g., THF, MeOH, EtOH, 1,4-dioxane, or mixtures of these) at ambient or elevated temperature. The acid may be isolated either as a salt with the metal cation or as free acid. tert-Butyl ester is preferably cleaved by treatment with an acid (e.g., hydrochloric acid or TFA) in a suitable solvent (e.g., DCM, 1,4-dioxane, THF, water, or mixtures of these). A benzyl ester is preferably cleaved by hydrogenolysis with a suitable catalyst (e.g., palladium on carbon) in a suitable solvent (e.g., EtOH, MeOH, THF, DCM, or EtOAc) under an atmosphere of hydrogen (preferably 1 to 5 bar).

Scheme 3

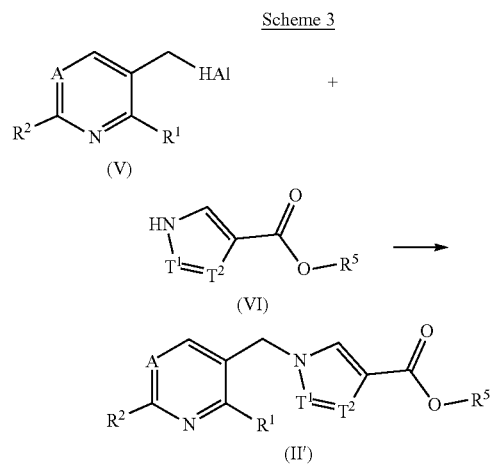

$T^1$ and $T^2$ are independently of each other N, C—H, or C—$R^4$; or
$T^1$ and $T^2$ form together an annulated benzo, pyrido, or pyrimido ring, which is optionally monosubstituted with $R^4$
$R^5 = C_{1-4}$-alkyl or benzyl Scheme 3: Some of the compounds (II') can be prepared by reaction of an alcohol (V) with an ester (VI) employing the conditions of the Mitsunobu reaction (e.g., triphenylphosphine or tri-n-butylphosphine combined with, e.g., diethyl azodicarboxylate (DEAD), diisopropyl azodicarboxylate (DIAD), or di-tert-butyl azodicarboxylate (DBAD) in a solvent such as THF, 1,4-dioxane, toluene, etc.); A, $R^1$, $R^2$, and $R^4$ in Scheme 3 have the meanings as defined hereinbefore. Alcohol (V) may bear the desired residue $R^2$ on the heteroaromatic ring or a leaving group instead to introduce $R^2$ later on. Alternatively, some of the compounds (II) can be obtained by reacting alcohol (V) and ester (VI) in the presence of a Lewis acid or Brønsted acid (e.g., 4-toluenesulfonic acid) in a suited solvent (e.g., ACN) at elevated temperature (20 to 120° C.).

Scheme 4

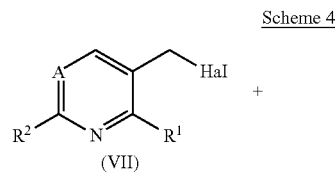

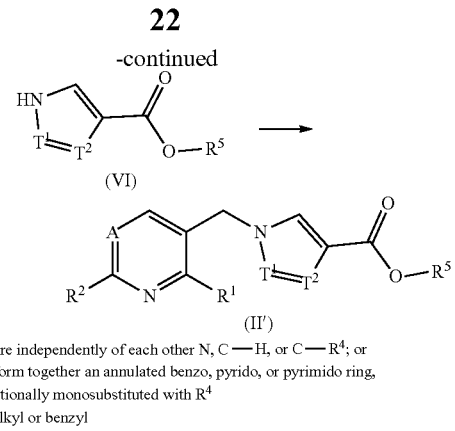

$T^1$ and $T^2$ are independently of each other N, C—H, or C—$R^4$; or
$T^1$ and $T^2$ form together an annulated benzo, pyrido, or pyrimido ring, which is optionally monosubstituted with $R^4$
$R^5 = C_{1-4}$-alkyl or benzyl
Hal = leaving group such as Cl, Br, I, $OSO_2CH_3$ Scheme 4: Some of the compounds (II') can also be prepared by reaction of compound (VII), bearing a leaving group at the heteroarylmethyl position such as Cl, Br, or mesyloxy (methanesulfonyloxy), with ester (VI) in the presence of a suitable base (e.g., sodium hydride, cesium carbonate, potassium carbonate, etc.) in a suitable solvent (e.g., THF, DMF, etc.); A, $R^1$, $R^2$, and $R^4$ in Scheme 4 have the meanings as defined hereinbefore. Compound (VII) may bear the desired residue $R^2$ on the heteroaromatic ring or a leaving group instead to introduce $R^2$ later on.

Scheme 5

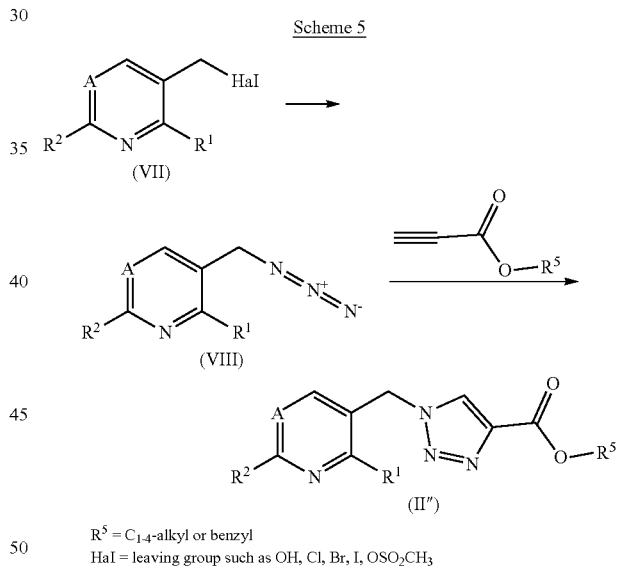

$R^5 = C_{1-4}$-alkyl or benzyl
Hal = leaving group such as OH, Cl, Br, I, $OSO_2CH_3$ Scheme 5: Some esters of formula (II"), wherein A, $R^1$, and $R^2$ have the meanings defined hereinbefore, can be prepared by the treatment of a corresponding alkyl halide (bromide or chloride) or sulfonate (e.g., mesylate) of formula (VII) with an azide source (e.g., sodium azide) in DMF or another suitable solvent to give an intermediate of formula (VIII) which is then reacted with a suitable propiolic acid ester under copper catalyzed conditions (e.g., ethyl propiolate or tert-butyl propiolate with catalytic copper sulfate and sodium ascorbate in water/tert-butanol) to give compound (II"). Alternatively, azide (VIII) can be obtained from an alcohol of formula (V) (Hal in compound (VII) is OH) by treatment with diphenylphosphoryl azide in the presence of a suitable base such as DBU in a suitable solvent (e.g., THF or DMF). Compound (VII) may bear the desired residue R² on the heteroaromatic ring or a leaving group instead to introduce R² later on.

Scheme 6

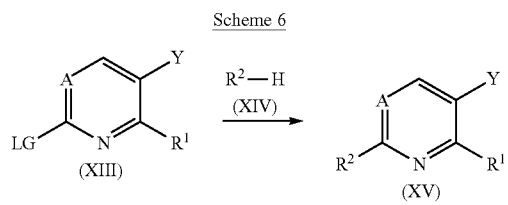

LG = leaving group such as F, Cl, Br, I

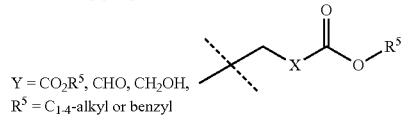

Y = CO₂R⁵, CHO, CH₂OH,
R⁵ = C₁₋₄-alkyl or benzyl

Scheme 6: Intermediates of formula (XV) can be prepared from heteroaromatic compound (XIII) and amine (XIV) via either a nucleophilic substitution reaction on the heteroaromatic ring or a transition metal catalyzed coupling reaction; A, X, R¹, and R² in Scheme 6 have the meanings defined hereinbefore. The nucleophilic substitution of a leaving group on the heteroaromatic ring in (XIII) with the N in compound (XIV) can be conducted in the presence of a suitable base (e.g., sodium hydride, cesium carbonate, potassium carbonate, or N,N-diisopropyl-ethylamine) in a suitable solvent (e.g., THF, 1,4-dioxane, DMF, or DMSO) at ambient or elevated temperature. A transition metal catalyzed coupling reaction is preferably carried out in analogy to procedures reported in the literature of organic chemistry referred to as Ullmann or Buchwald/Hartwig coupling reaction using suitable palladium or copper salts or complexes thereof, optionally combined with additional ligands, in the presence of a base and in a suited solvent.

Scheme 7

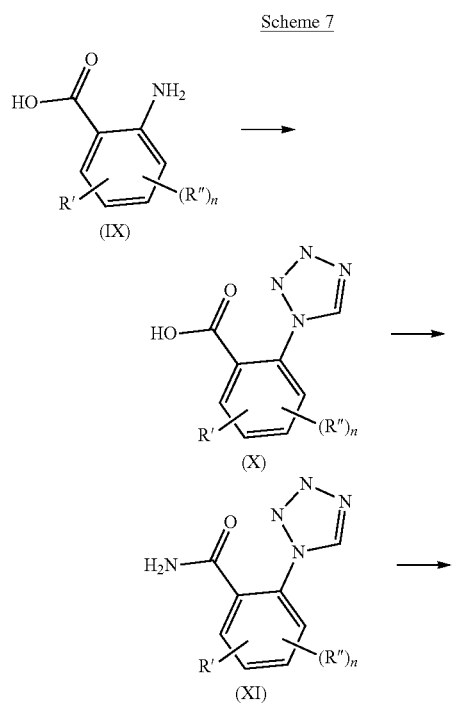

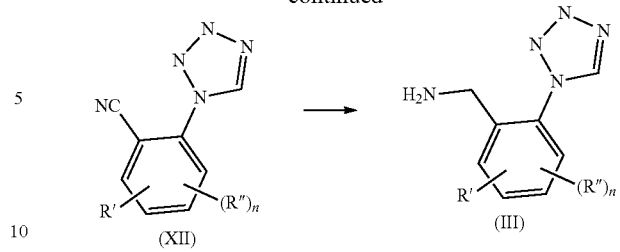

Scheme 7: Benzyl amines of formula (III) can be prepared from benzoic acids in a four-step synthesis sequence as delineated in Scheme 7; R', R", and n in Scheme 7 have the meanings defined hereinbefore. Treatment of carboxylic acid (IX) with an azide source (e.g., sodium azide) and an ortho ester of formic acid (e.g., trimethyl orthoformate) in acetic acid may provide tetrazole (X). Amide (XI) can be prepared from acid (X) by reaction with an ammonia source (e.g., aqueous ammonia, ammonia in an organic solvent, or ammonium chloride) in the presence of a suitable coupling agent (e.g., O-(7-azabenzotriazol-1-yl)-N,N,N',N'-tetramethyluronium-hexafluorophosphate (HATU), O-(benzotriazol-1-yl)-N,N,N',N'-tetramethyluronium tetrafluoroborate (TBTU), (benzotriazol-1-yloxy)tripyrrolidino-phosphonium hexafluorophosphate (PyBOP), carbodiimide reagents, etc.) and a base (e.g., triethylamine, N,N-diisopropyl-ethylamine, pyridine, etc.) in a suitable solvent (e.g., DCM, THF, 1,4-dioxane, DMF, N,N-dimethylacetamide, and 1-methyl-2-pyrrolidinone). Dehydration of amide (XI) can be accomplished by using a dehydrating reagent (e.g., Burgess reagent, trifluoroacetic acid anhydride, or thionyl chloride), optionally in the presence of a base (e.g., triethylamine, N,N-diisopropyl-ethylamine, or pyridine), in an inert solvent (e.g., DCM, THF, 1,4-dioxane, or toluene) to give nitrile (XII). Nitrile (XII) can be reduced with hydrogen (preferably 1 to 5 bar) in the presence of a transition metal (e.g., Raney Ni or Pd on carbon), optionally in the presence of ammonia, in a suitable solvent (e.g., alcohol, THF, EtOAc, or mixture of them) to furnish amine (III). Alternatively, the amine is intercepted during the hydrogenation process with an acylating reagent (e.g., di-tert-butyl dicarbonate) to give the N-acylated form of amine (III) (e.g., tert-butoxycarbonylated) which can then be liberated from the acyl group by employing conditions suited for the respective acyl group (e.g., tert-butyloxycarbonyl is preferably cleaved off with acid, e.g., TFA or hydrogen chloride in DCM or dioxane).

The compounds of formula (I) may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of formula (I) which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physicochemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula (I) may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

Pharmacological Activity

The activity of the compounds of the invention may be demonstrated using the following assay:

Biological Methods

The ability of compounds of formula (I) to inhibit plasma kallikrein (PKK), Factor XIIa (FXIIa), Factor XIa (FXIa), Factor Xa (FXa), Factor IIa (alpha-thrombin; FIIa), plasmin, trypsin, tissue kallikrein 1 (TK1), Factor VIIa (FVIIa), or FVIIa complexed with Tissue Factor, phospholipids and $CaCl_2$) (FVIIa/TF/PL/$CaCl_2$) was determined using the following biochemical assays in assay buffer (100 mM Tris, 150 mM NaCL, adjusted to a pH of 7.8 with HCl, and containing 0.1% (w/v) BSA and 0.05% (v/v) Tween20) in the presence of 1% (v/v) DMSO:

Evaluation of the Inhibition of PKK Using an Endpoint Assay

Human PKK (0.01 U/mL; Enzyme Research Laboratories) or rat PKK (0.625 nM; produced in-house) was incubated for 1 h at rt with 0.10 μM fluorogenic substrate H-Pro-Phe-Arg-AMC (11295 from Bachem) and various concentrations of the test compound in assay buffer. Subsequently, PPACK II (Calbiochem) was added as a stop solution to achieve a final concentration of 1 μM and fluorescence was measured using an Envision Reader (PerkinElmer) with the wavelength excitation setting of 355 nm and the wavelength emission setting of 460 nm. $IC_{50}$ values for compounds according to the invention are shown in the following table. The number of the compound corresponds to the number of the Example in the experimental section.

| Example | $IC_{50}$ (nM) |
| --- | --- |
| 1 | 0.5 |
| 2 | 5 |
| 3 | 0.4 |
| 4 | 82 |
| 5 | 0.9 |
| 6 | 0.4 |
| 7 | 0.8 |
| 8 | 1 |
| 9 | 1 |
| 10 | 0.5 |
| 11 | 0.6 |
| 12 | 0.9 |
| 13 | 0.9 |
| 14 | 0.6 |
| 15 | 2 |
| 16 | 0.6 |
| 17 | 0.4 |
| 18 | 1 |
| 19 | 0.7 |
| 20 | 0.4 |
| 21 | 3 |
| 22 | 1 |
| 23 | 1 |
| 24 | 2 |
| 25 | 1 |
| 26 | 0.9 |
| 27 | 3 |
| 28 | 14 |
| 29 | 2 |
| 30 | 0.8 |
| 31 | 2 |
| 32 | 1 |
| 33 | 0.8 |
| 34 | 1 |
| 35 | 1 |
| 36 | 5 |
| 37 | 2 |
| 38 | 0.7 |
| 39 | 3 |
| 40 | 0.5 |
| 41 | 6 |
| 42 | 0.6 |
| 43 | 0.4 |
| 44 | 1 |
| 45 | 3 |
| 46 | 0.7 |
| 47 | 3 |
| 48 | 0.8 |
| 49 | 1 |
| 50 | 9 |
| 51 | 2 |
| 52 | 0.6 |
| 53 | 0.2 |
| 54 | 3 |
| 55 | 3 |
| 56 | 6 |
| 57 | 5 |
| 58 | 38 |
| 59 | 0.7 |
| 60 | 4 |
| 61 | 12 |
| 62 | 3 |
| 63 | 0.5 |
| 64 | 225 |
| 65 | 10 |
| 66 | 9 |
| 67 | 10 |
| 68 | 4 |
| 69 | 5 |
| 70 | 845 |
| 71 | 8 |
| 72 | 74 |
| 73 | 9 |
| 74 | 232 |
| 75 | 7 |
| 76 | 3 |
| 77 | 49 |
| 78 | 19 |
| 79 | 1063 |
| 80 | 22 |
| 81 | 22 |
| 82 | 7 |
| 83 | 1090 |
| 84 | 4 |
| 85 | 3 |

-continued

| Example | IC$_{50}$ (nM) |
|---|---|
| 86 | 7 |
| 87 | 0.9 |
| 88 | 127 |
| 89 | 61 |
| 90 | 119 |
| 91 | 122 |
| 92 | 155 |
| 93 | 286 |
| 94 | 4 |

Evaluation of the Inhibition of PKK in Kaolin Activated Human PPP

Platelet poor plasma (PPP) obtained from human whole-blood, anticoagulated with Na-Citrate, was incubated with various concentrations of the test compound together with either 25, 75, 250, or 750 µg/mL kaolin in assay buffer for 20 min at 37° C. such that for each kaolin dose used a concentration response was obtained for the test compound. Afterwards 0.25 mM fluorogenic substrate H-Pro-Phe-Arg-AMC (11295 from Bachem) was added to the mixture and measurements were performed in a kinetic interval every 2nd minute for 12 min using a Spectramax M5 (Molecular Devices) with the following settings of the wavelength excitation of 350 nm and wavelength emission of 450 nm. pIC50 and pIC90 values were obtained from 4 x/y-plots (x=log M, Compound; y=delta RFU/min) fitted with GraphPad prism 7.0 (Equation: log(agonist) vs. response—Find ECanything; the four concentration response curves obtained for the test compound, each obtained using a different kaolin dose, were fitted using a global fitting procedure yielding shared pIC50 or pIC90 values).

IC90 values for compounds according to the invention are shown in the following table. The number of the compound corresponds to the number of the Example in the experimental section.

| Example | IC$_{90}$ (nM) |
|---|---|
| 1 | 202 |
| 2 | 1150 |
| 3 | 170 |
| 5 | 316 |
| 6 | 184 |
| 9 | 239 |
| 13 | 396 |
| 15 | 419 |
| 21 | 713 |
| 42 | 257 |
| 44 | 341 |
| 45 | 106 |
| 46 | 341 |
| 47 | 711 |
| 48 | 316 |
| 49 | 932 |
| 52 | 103 |
| 54 | 969 |
| 59 | 847 |
| 60 | 4070 |
| 63 | 209 |
| 87 | 252 |

Evaluation of the Inhibition of PKK ($K_i$)

Human PKK (1.78 nM or 0.025 U/mL; Enzyme Research Laboratories) was incubated at 24° C. with 0.25 mM fluorogenic substrate H-Pro-Phe-Arg-AMC (11295 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm. $K_i$ values for compounds according to the invention are shown in the following table. The number of the compound corresponds to the number of the Example in the experimental section.

| Example | $K_i$ (nM) |
|---|---|
| 1 | 0.3 |
| 2 | 0.8 |
| 3 | 0.2 |
| 5 | 0.4 |
| 9 | 0.8 |
| 13 | 0.8 |
| 15 | 0.7 |
| 21 | 1 |
| 42 | 1 |
| 44 | 0.5 |
| 45 | 0.3 |
| 46 | 1 |
| 47 | 0.7 |
| 48 | 0.5 |
| 49 | 0.4 |
| 52 | 0.4 |
| 54 | 1 |
| 59 | 0.3 |
| 60 | 2 |
| 63 | 0.3 |
| 87 | 0.8 |

Evaluation of the Inhibition of FXIIA ($K_i$)

Human FXIIa (47.5 nM or 1.1 U/mL; Enzyme Research Laboratories) was incubated at 24° C. with 0.5 mM chromogenic Substrate S2302 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FXIA ($K_i$)

Human FXIa (0.5 nM or 0.016 U/mL; Enzyme Research Laboratories) was incubated at 24° C. with 0.25 mM fluorogenic substrate Boc-Glu(OBzl)-Ala-Arg-AMC.HCl (11575 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FXa ($K_i$)

Human FXa (0.86 nM or 0.01 U/mL; Enzyme Research Laboratories) was incubated at 24° C. with 0.5 mM chromogenic Substrate S2765 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FIIa ($K_i$)

Human FIIa (44.6 nM or 5 U/mL; Enzyme Research Laboratories) was incubated at 24° C. with 0.5 mM chromogenic Substrate S2238 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of Plasmin ($K_i$)

Human plasmin (64.1 nM or 0.0275 U/mL; Enzyme Research Laboratories) was incubated at 24° C. with 0.3 mM chromogenic Substrate S2251 (Chromogenix) and various concentrations of the test compound in assay buffer.

Measurements were performed in a kinetic interval every $2^{nd}$ minute for 16 min using a Spectramax M5 (Molecular Devices) measuring the optical absorbance at 405 nm.

Evaluation of the Inhibition of Trypsin ($K_i$)

Human trypsin (4.54 nM or 250 U/mL; Calbiochem) was incubated at 24° C. with 0.5 mM chromogenic Substrate S2222 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of TK1 ($K_i$)

Prior to the assay, human TK1 (R&D Systems) was activated by incubation with human trypsin (Calbiochem) in a 1:10,000 ratio for 15 min at 37° C. For assaying TK1 inhibitory activity, activated TK1 (31.25 nM or 1 U/mL) was incubated at 24° C. with 0.1 mM fluorogenic substrate H-Pro-Phe-Arg-AMC (I1295 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FVIIa ($K_i$)

Human FVIIa (0.86 nM or 0.01 U/mL; Enzyme Research Laboratories) was incubated at 24° C. with 1.5 mM chromogenic Pefachrome® FVIIa (Loxo) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FVIIa/TF/PL/CaCl$_2$ ($K_i$)

Human FVIIa (300 nM or 585 U/mL; Enzyme Research Laboratories) together with 10 mM CaCl$_2$)*2H$_2$O and 13.3% (v/v) Dade®Innovin® (Siemens; OQUMI94E0002 (5534), which contains recombinant human tissue factor synthetic phospholipids (thromboplastin), was incubated at 24° C. with 1.5 mM chromogenic Pefachrome® FVIIa (Loxo) and various concentrations of the test compound in assay buffer. Measurements were performed in a kinetic interval every $2^{nd}$ minute for 16 min using a Spectramax M5 (Molecular Devices) measuring the optical absorbance at 405 nm.

Calculation of pIC$_{50}$ and pK$_i$ Values

The average V$_{max}$ values for the time interval from 2 to 12 min after initiation of the assay (expressed as either delta OD/min for assays using a chromogenic substrate or delta RFU/min for assays using a fluorigenic substrate, respectively) were plotted versus the Log of the concentration in molar of the evaluated inhibitor compound. The pIC$_{50}$ values were then fitted using a four-parametric fitting procedure using using GraphPad Prism (version 6; GraphPad Software, Inc.). Respective $K_i$ values were obtained by correction of the IC50 values for the respective $K_M$ value of the used substrate (see Table A for the obtained $K_M$ values of the used substrates) using the following formula:

$$K_i = \frac{IC_{50}}{1 + \frac{[\text{Substrate, mM}]}{K_M}}$$

Where the IC$_{50}$ is in mol/L and the K$_M$ value in mmol/L.

TABLE A

K$_M$ values obtained for the substrates used in the enzymatic assays.

| Enzyme | Substrate | K$_M$ (mM) |
|---|---|---|
| PKK | I1295 | 0.16 |
| FXIIa | S2302 | 0.20 |
| FXIa | I1575 | 0.29 |
| FXa | S2765 | 1.31 |
| FIIa | S2238 | 1.25 |
| Plasmin | S2251 | 1.45 |
| Trypsin | S2222 | 2.03 |
| TK1 | I1295 | 0.07 |
| FVIIa | Pefachrome ® FVIIa | 0.42 |
| FVIIa/TF/PL/CaCl$_2$ | Pefachrome ® FVIIa | 3.92 |

Evaluation of Permeability

Caco-2 cells (1-2×10$^5$ cells/1 cm$^2$ area) are seeded on filter inserts (Costar transwell polycarbonate or PET filters, 0.4 μm pore size) and cultured (DMEM) for 10 to 25 d.

Compounds are dissolved in appropriate solvent (like DMSO, 1-20 mM stock solutions). Stock solutions are diluted with HTP-4 buffer (128.13 mM NaCl, 5.36 mM KCl, 1 mM MgSO$_4$, 1.8 mM CaCl$_2$), 4.17 mM NaHCO$_3$, 1.19 mM Na$_2$HPO$_4$×7H$_2$O, 0.41 mM NaH$_2$PO$_4$×H$_2$O, 15 mM HEPES, 20 mM glucose, pH 7.2) to prepare the transport solutions (0.1-300 μM compound, final DMSO <=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 h also from the receiver side for concentration measurement by HPLC-MS/MS or scintillation counting. Sampled receiver volumes are replaced with fresh receiver solution.

Evaluation of Metabolic Stability in Human or Rat Liver Microsomes

The metabolic degradation of the test compound is assayed at 37° C. with pooled human or rat liver microsomes. The final incubation volume of 100 μL per time point contains TRIS buffer pH 7.6 at RT (0.1 M), magnesium chloride (5 mM), microsomal protein (1 mg/mL) and the test compound at a final concentration of 1 μM.

Following a short preincubation period at 37° C., the reactions were initiated by addition of beta-nicotinamide adenine dinucleotide phosphate, reduced form (NADPH, 1 mM) and terminated by transferring an aliquot into solvent after different time points. Additionally, the NADPH-independent degradation was monitored in incubations without NADPH, terminated at the last time point. The quenched incubations are pelleted by centrifugation (10000 g, 5 min). An aliquot of the supernatant is assayed by LC-MS/MS for the amount of parent compound. The half-life (t½ INVITRO) is determined by the slope of the semilogarithmic plot of the concentration-time profile.

Evaluation of Metabolic Stability in Human or Rat Hepatocytes

The metabolic degradation of the test compound is assayed in a hepatocyte suspension. Hepatocytes (typically cryopreserved) are incubated in an appropriate buffer system (e.g. Dulbecco's modified eagle medium plus 3.5 μg glucagon/500 mL, 2.5 mg insulin/500 mL and 3.75 mg/500 mL hydrocortison) containing 5% species serum. Following a (typically) 30 min preincubation in an incubator (37° C., 10% CO$_2$) 5 μL of test compound solution (80 μM; from 2 mM in DMSO stock solution diluted 1:25 with medium) are added into 395 μL hepatocyte suspension (cell density in the range 0.25-5 Mio cells/mL, typically 1 Mio cells/mL; final concentration of test compound 1 µM, final DMSO concentration 0.05%).

The cells are incubated for 6 h (incubator, orbital shaker) and samples (25 µL) are taken at 0, 0.5, 1, 2, 4 and 6 h. Samples are transferred into ACN and pelleted by centrifugation (5 min). The supernatant is transferred to a new 96-deepwell plate, evaporated under nitrogen and resuspended.

Decline of parent compound is analyzed by HPLC-MS/MS CLint is calculated as follows CL_INTRINSIC=Dose/AUC=(C0/CD)/(AUD+clast/k)×1000/60. C0: initial concentration in the incubation [µM], CD: cell density of vital cells [10e6 cells/mL], AUD: area under the data [µM×h], clast: concentration of last data point [µM], k: slope of the regression line for parent decline [h-1].

Evaluation of Plasma Protein Binding

This equilibrium dialysis (ED) technique is used to determine the approximate in vitro fractional binding of test compounds to plasma proteins. Dianorm Teflon dialysis cells (micro 0.2) are used. Each cell consists of a donor and an acceptor chamber, separated by an ultrathin semipermeable membrane with a 5 kDa molecular weight cutoff. Stock solutions for each test compound are prepared in DMSO at 1 mM and diluted to a final concentration of 1.0 µM. The subsequent dialysis solutions are prepared in pooled human or rat plasma (with NaEDTA) from male and female donors. Aliquots of 200 µL dialysis buffer (100 mM potassium phosphate, pH 7.4) are dispensed into the buffer chamber. Aliquots of 200 µL test compound dialysis solution are dispensed into the plasma chambers. Incubation is carried out for 2 h under rotation at 37° C.

At the end of the dialysis period, the dialysate is transferred into reaction tubes. The tubes for the buffer fraction contain 0.2 mL ACN/water (80/20). Aliquots of 25 µL of the plasma dialysate are transferred into deep well plates and mixed with 25 µL ACN/water (80/20), 25 µL buffer, 25 µL calibration solution and 25 µL Internal Standard solution. Protein precipitation is done by adding 200 µL ACN.

Aliquots of 50 µL of the buffer dialysate are transferred into deep well plates and mixed with 25 µL blank plasma, 25 µL Internal Standard solution and 200 µL ACN.

Samples are measured on HPLC-MS/MS-Systems and evaluated with Analyst-Software.

Percent bound is calculated with the formula: % bound=(plasma concentration−buffer concentration/plasma concentration)×100

Evaluation of Solubility

The aqueous solubility of the test compound is determined by comparing the amount dissolved in buffer to the amount in an ACN/water (1/1) solution. Starting from a 10 mM DMSO stock solution aliquots are diluted with ACN/water (1/1) or buffer resp. After 24 h of shaking, the solutions are filtrated and analyzed by LC-UV. The amount dissolved in buffer is compared to the amount in the ACN solution.

Solubility will usually be measured from 0.001 to 0.125 mg/mL at a DMSO concentration of 2.5%. If more than 90% of the compound is dissolved in buffer, the value is marked with ">".

Evaluation of Pharmacokinetic Characteristics in Rodents

The test compound is administered either intravenously to fed rats or orally to fasted rats. Blood samples are taken at several time points post application of the test compound, anticoagulated and centrifuged.

The concentration of analytes—the administered compound and/or metabolites—are quantified in the plasma samples. PK parameters are calculated using non compartment methods. AUC and Cmax are normalized to a dose of 1 µmol/kg.

Methods of Treatment

In another aspect of the present invention, it is found that compounds of formula (I) or pharmaceutically acceptable salts thereof may be useful for the treatment of diseases or conditions mediated by unwanted PKK activity in a mammal.

Diseases and conditions mediated by unwanted PKK activity embrace diabetic complications, diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retinal vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), choroidal neovascularization (CNV; e.g. non-exudative choroidal neovascularization), hereditary angioedema and acute respiratory distress syndrome (ARDS).

Thus, the compounds and pharmaceutical compositions of the present invention are particularly suitable for treating ocular diseases including diabetic retinopathy, proliferative and non-proliferative retinopathy, diabetic macular edema (DME), retinal vein occlusion, age-related macular degeneration (AMD), polypoidal choroidal vasculopathy (PCV) and choroidal neovascularization (CNV; e.g. non-exudative choroidal neovascularization).

In addition, the compounds and pharmaceutical compositions according to the invention are particularly suitable for the treatment of edema, such as hereditary angioedema.

In particular, the compounds and pharmaceutical compositions according to the invention are suitable for the treatment of diabetic retinopathy, proliferative and non-proliferative retinopathy, diabetic macular edema (DME), age-related macular degeneration (AMD), polypoidal choroidal vasculopathy (PCV), choroidal neovascularization (CNV) and hereditary angioedema.

The compounds and pharmaceutical compositions according to the invention are most particularly suitable for treating diabetic macular edema (DME), wet age-related macular degeneration (AMD), non-exudative choroidal neovascularization (CNV) and hereditary angioedema.

The dose range of the compounds of formula (I) applicable per day is usually from 0.01 to 10 mg per kg body weight. The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, intravitreal, transdermal, inhalative, parenteral or sublingual route. Of the possible methods of administration, oral or intravitreal administration is preferred. In case of intravitreal injection the preferred dose should not exceed 5 mg per eye.

Thus, in a further aspect the invention provides new compounds of formula (I), including pharmaceutically acceptable salts thereof, which inhibit plasma kallikrein and possess suitable pharmacological and pharmacokinetic properties for use in therapy, i.e. for use as medicaments.

In a further aspect the invention provides new compounds of formula (I), including pharmaceutically acceptable salts thereof, for use in a method for the treatment of a disease or condition which can be influenced in a beneficial way by inhibition of plasma kallikrein.

In a further aspect the invention provides new compounds of formula (I), or pharmaceutically acceptable salts thereof, for the treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) as well as of edema-associated diseases such as hereditary angioedema.

In another aspect, the present invention provides the use of a compound of formula (I), or pharmaceutically acceptable salts thereof, in the manufacture of a medicament for use in the treatment of a disease or condition in which inhibition of plasma kallikrein is beneficial.

In a further aspect, the present invention provides the use of a compound of formula (I), or pharmaceutically acceptable salts thereof, in the manufacture of a medicament for use in the treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) and of edema-associated diseases such as hereditary angioedema.

Accordingly, the present invention relates to compounds of formula (I) as a medicament.

Furthermore, the present invention relates to the use of a compound of formula (I) in a method for the treatment of diseases or conditions which are mediated by unwanted plasma kallikrein activity in a patient, preferably in a human.

Furthermore, the present invention relates to the use of a compound of formula (I) in a method for the treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) and of edema-associated diseases such as hereditary angioedema.

In yet another aspect the present invention relates to a method for the treatment of a disease or condition which can be influenced by the inhibition of plasma kallikrein in a mammal that includes the step of administering to a patient, preferably a human, in need of such treatment a therapeutically effective amount of a compound or a pharmaceutical composition of the present invention.

In a further aspect the invention provides a method for the treatment of a disease or condition which can be influenced in a beneficial way by inhibition of plasma kallikrein, in a subject comprising administering a therapeutically effective amount of a compound of formula (I), or a pharmaceutically acceptable salt thereof, to a patient in need thereof.

In a further aspect the invention provides a method for the treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) and of edema-associated diseases such as hereditary angioedema in a patient, comprising administering a therapeutically effective amount of a compound of formula (I), or a pharmaceutically acceptable salt, thereof to a patient in need thereof.

According to another aspect of the invention, there is provided a method for the treatment of diabetic complications, particularly of retinal vascular permeability associated with diabetic retinopathy and diabetic macular edema, in a patient in need thereof characterized in that a therapeutically effective amount of a compound of formula (I) or a pharmaceutically acceptable salt thereof is administered to the patient.

Pharmaceutical Compositions

In another aspect of the present invention, it is described that a compound of the invention or a pharmaceutically acceptable salt thereof may be used as active ingredients in pharmaceutical compositions.

Suitable preparations for administering the compounds of the invention, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. For intravitreal injection, solutions are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula (I) according to the invention, or a pharmaceutically acceptable salt of such a compound, and one or more excipients, carriers and/or diluents.

Thus, according to another aspect of the present invention, pharmaceutical compositions comprising one or more compounds of formula (I), or pharmaceutically acceptable salts thereof, optionally together with one or more inert carriers and/or diluents are provided.

Also, a pharmaceutical composition is provided that comprises one or more of the above-mentioned compounds, or pharmaceutically acceptable salts thereof, optionally together with one or more inert carriers and/or diluents for use in a method for the treatment of diseases or conditions which can be influenced by the inhibition of PKK.

In particular, the invention provides a pharmaceutical composition according to the invention for use in a method of treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) and of edema-associated diseases such as hereditary angioedema.

Furthermore, the present invention relates to the use of a pharmaceutical composition according to this invention for the treatment of diseases or conditions which are mediated by unwanted PKK activity in a patient, preferably in a human.

Also, the present invention relates to the use of a pharmaceutical composition according to this invention for the treatment of diseases or conditions which can be influenced by the inhibition of PKK in a patient, preferably in a human.

According to another embodiment, a pharmaceutical composition comprising one or more compounds of formula (I), or pharmaceutically acceptable salts thereof, and one or more additional therapeutic agents, optionally together with one or more inert carriers and/or diluents is provided. Preferably, this composition comprises one compound of formula (I) or a pharmaceutically acceptable salt thereof and one or more additional therapeutic agents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia, or therapeutic agents useful for the treatment of ocular diseases. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity, agents for the treatment of high blood pressure, heart failure and/or atherosclerosis and agents for the treatment of ocular diseases. Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, 33-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

Therapeutic agents for the treatment of ocular diseases may include for example intravitreally administered corticosteroids, intravitreally administered anti-VEGF therapy, anti-Ang2 inhibitors, dual anti-VEGF/anti-Ang2 inhibitors, anti PDGF, dual anti-VEGF/anti-PDGF, VAP-1 (AOC3) inhibitors, Complement inhibitors (e.g. Complement factors 3, 5, B, and D inhibitors), Bradykinin receptor 1 antagonists, CCR-2 antagonists.

Additional treatments for ocular diseases may include laser coagulation therapy.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by unwanted plasma kallikrein activity, in particular diseases or conditions as described hereinbefore and hereinafter.

In a further aspect this invention relates to a method for treating a disease or condition which can be influenced by the inhibition of plasma kallikrein in a patient that includes the step of administering to the patient in need of such treatment a therapeutically effective amount of a compound of formula (I) or a pharmaceutically acceptable salt thereof in combination with a therapeutically effective amount of one or more additional therapeutic agents.

In a further aspect this invention relates to the use of a compound of formula (I) or a pharmaceutically acceptable salt thereof in combination with one or more additional therapeutic agents for the treatment of diseases or conditions which can be influenced by the inhibition of plasma kallikrein in a patient in need thereof.

In yet another aspect the present invention relates a method for the treatment of a disease or condition mediated by unwanted plasma kallikrein activity in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter.

The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES AND EXPERIMENTAL DATA

The following examples are for the purpose of illustration of the invention only and are not intended in any way to limit the scope of the present invention.

The terms "ambient temperature" and "room temperature" are used interchangeably and designate a temperature of about 20° C., e.g., 15 to 25° C.

As a rule, $^1$H-NMR and/or mass spectra have been obtained for the compounds prepared.

Unless otherwise specified, compounds containing chiral centers have the stereochemistry depicted. The assignment of stereochemistry has been made either by use of a chiral starting material of known stereochemistry, by stereoselective synthesis of known stereochemistry or by biological activity.

Analytical Methods

| Method: | 1 |
|---|---|
| Device: | Agilent 1200 with DA- and MS-Detector |
| Column: | Sunfire C18, 3 × 30 mm, 2.5 μm |
| Column Supplier: | Waters |

| Gradient/ Solvent Time [min] | % Solvent [H$_2$O, 0.1% TFA] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 2 |
|---|---|
| Device: | Agilent 1200 with DA- and MS-Detector |
| Column: | XBridge C18, 3 × 30 mm, 2.5 μm |
| Column Supplier: | Waters |

| Gradient/ Solvent Time [min] | % Solvent [H$_2$O, 0.1% NH$_3$] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 3 |
|---|---|
| Device: | Agilent 1200 with DA- and MS-Detector |
| Column: | XBridge C18, 3 × 30 mm, 2.5 μm |
| Column Supplier: | Waters |

| Gradient/ Solvent Time [min] | % Solvent [H$_2$O, 0.1% NH$_3$] | % Solvent [ACN] | Flow [mL/min] | Temperature [° C.] |
|---|---|---|---|---|
| 0.00 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.70 | 0 | 100 | 2.9 | 60 |

| Method: | 4 |
|---|---|
| Device: | Waters Acquity with DA- and MS-Detector |
| Column: | Sunfire C18, 2.1 × 30 mm, 2.5 μm |
| Column Supplier: | Waters |

| Gradient/ Solvent Time [min] | % Solvent [H$_2$O, 0.1% TFA] | % Solvent [ACN] | Flow [mL/min] | Temperature [° C.] |
|---|---|---|---|---|
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

| Method: | 5 |
|---|---|
| Device: | Waters Acquity, QDa Detector |
| Column: | Sunfire C18, 3 × 30 mm, 2.5 μm |
| Column Supplier: | Waters |

| Gradient/ Solvent Time [min] | % Solvent [H$_2$O, 0.1% TFA] | % Solvent [ACN, 0.08% TFA] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

| Method: | 6 |
|---|---|
| Device: | Waters Acquity, QDa Detector |
| Column: | XBridge C18, 3 × 30 mm, 2.5 μm |
| Column Supplier: | Waters |

| Gradient/ Solvent Time [min] | % Solvent [H$_2$O, 0.1% NH$_3$] | % Solvent [ACN] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

| Method: | 7 |
|---|---|
| Device: | Waters Acquity, QDa Detector |
| Column: | XBridge C18, 3 × 30 mm, 2.5 μm |
| Column Supplier: | Waters |

| Gradient/ Solvent Time [min] | % Solvent [H$_2$O, 0.1% NH$_3$] | % Solvent [ACN] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

| Method: | 8 |
| --- | --- |
| Device: | LC/MS Waters Acquity UPLC System DAD, SQD single quadrupole |
| Column: | BEH C18 1.7 µm 2.1 × 50 mm, Temp 35° C. |
| Column Supplier: | Waters |

| Gradient/ Solvent Time [min] | % Solvent [$H_2O$ 90% + ACN 10% + $NH_4COOH$ 5 mM] | % Solvent [ACN 90% + $H_2O$ 10%] | Flow [mL/min] | Temperature [° C.] |
| --- | --- | --- | --- | --- |
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

| Method: | 9 |
| --- | --- |
| Device: | LC/MS ThermoFinnigan HPLC Surveyor DAD, MSQ single quadrupole |
| Column: | Synergi Hydro RP100A, 2.5 µm, 3 × 50 mm |
| Column Supplier: | Phenomenex |

| Gradient/ Solvent Time [min] | % Solvent [$H_2O$ 90% + ACN 10% + $NH_4COOH$ 10 mM] | % Solvent [ACN 90% + $H_2O$ 10% + $NH_4COOH$ 10 mM] | Flow [mL/min] | Temperature [° C.] |
| --- | --- | --- | --- | --- |
| 0.00 | 100 | 0 | 1.2 | 35 |
| 0.50 | 100 | 0 | 1.2 | 35 |
| 6.50 | 0 | 100 | 1.2 | 35 |
| 7.50 | 0 | 100 | 1.2 | 35 |
| 8.00 | 100 | 0 | 1.2 | 35 |
| 9.00 | 100 | 0 | 1.2 | 35 |

SYNTHESIS OF INTERMEDIATES

Intermediate 1

(2-{6,6-Difluoro-3-azabicyclo[3.1.0]hexan-3-yl}-4-methylpyrimidin-5-yl)methanol

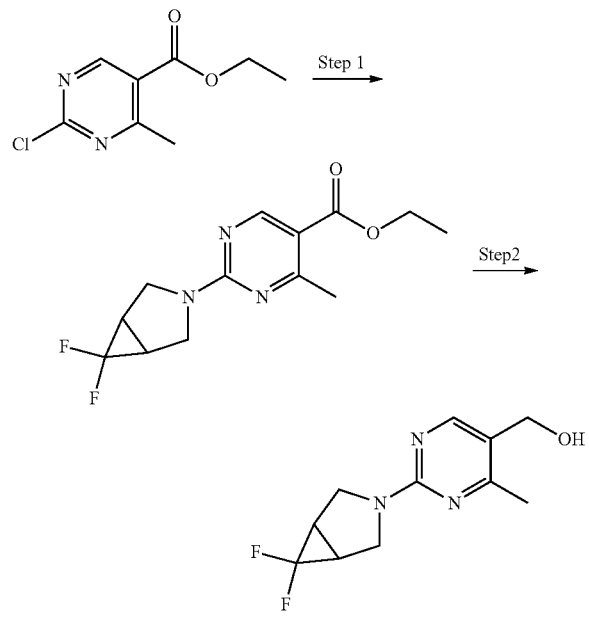

Step 1: Ethyl 2-{6,6-difluoro-3-azabicyclo[3.1.0]hexan-3-yl}-4-methylpyrimidine-5-carboxylate Ethyl-2-chloro-4-methylpyrimidine-5-carboxylate (5.0 g), 6,6-difluoro-3-azabicyclo[3.1.0]hexane hydrochloride (4.26 g) and $K_2CO_3$ (10.3 g) are suspended in DMF (50 mL) and heated to 90° C. for 1 h. The mixture is cooled, partitioned between water and EtOAc and the phases are separated. The organic phase is washed with brine. After drying ($MgSO_4$) the solvents are evaporated in vacuo to give the title compound.

LC (Method 1): $t_R$=1.065 min; Mass spectrum (ESI$^+$): m/z=284 [M+H]$^+$.

Step 2: (2-{6,6-Difluoro-3-azabicyclo[3.1.0]hexan-3-yl}-4-methylpyrimidin-5-yl)methanol To a solution of ethyl 2-{6,6-difluoro-3-azabicyclo[3.1.0]hexan-3-yl}-4-methylpyrimidine-5-carboxylate (7.15 g) in THF (20 mL) is added $LiBH_4$ (16.62 mL; 2M solution in THF). The mixture is stirred for 20 min, MeOH (2.0 mL) is added and stirring continued for 16 h at rt. After cooling to 0° C. the mixture is slowly treated with water and stirred for 10 min. Then the mixture is extracted with EtOAc and the solvents are evaporated in vacuo to give the title compound.
LC (Method 1): $t_R$=0.64 min; Mass spectrum (ESI$^+$): m/z=242 [M+H]$^+$.

Intermediate 2

(2-{3-Azabicyclo[3.1.0]hexan-3-yl}-4-methylpyrimidin-5-yl)methanol

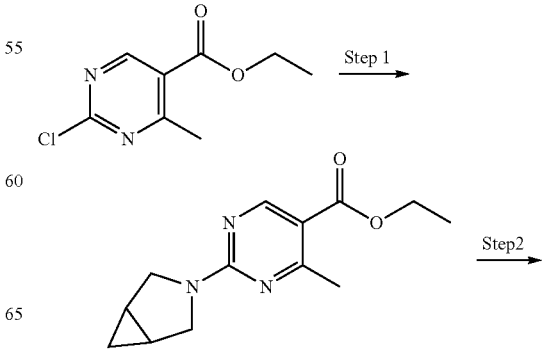

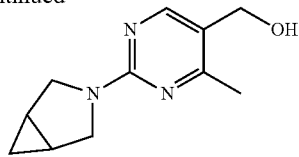

Step 1: Ethyl 2-{3-azabicyclo[3.1.0]hexan-3-yl}-4-methylpyrimidine-5-carboxylate Ethyl-2-chloro-4-methylpyrimidine-5-carboxylate (1.0 g), 6,6-difluoro-3-azabicyclo[3.1.0]hexane hydrochloride (0.66 g) and $K_2CO_3$ (2.1 g) are suspended in DMF (15 mL) and heated to 100° C. for 1 h. The mixture is cooled, partitioned between water and EtOAc and the phases are separated. The organic phase is washed with brine. After drying ($MgSO_4$) the solvents are evaporated in vacuo to give the title compound.

LC (Method 1): $t_R$=1.04 min; Mass spectrum (ESI$^+$): m/z=248 [M+H]$^+$.

Step 2: (2-{3-Azabicyclo[3.1.0]hexan-3-yl}-4-methylpyrimidin-5-yl)methanol

A solution of ethyl 2-{3-azabicyclo[3.1.0]hexan-3-yl}-4-methylpyrimidine-5-carboxylate (1.2 g) in THF (10 mL) is cooled in an ice/acetone bath and diisobutylaluminiumhydride (10 mL; 1M solution in THF) is added. The mixture is stirred for 1 h under cooling. The mixture is slowly treated with water (0.75 mL) and 4 M NaOH (0.75 mL), stirred for 30 min and filtered through a pad of celite. After drying ($MgSO_4$) the mixture is concentrated in vacuo and the residue is chromatographed over silica gel (EtOAc/MeOH 100:0→50:50). The solvents are evaporated in vacuo to give the title compound.

LC (Method 1): $t_R$=0.58 min; Mass spectrum (ESI$^+$): m/z=206 [M+H]$^+$.

Intermediate 3

(2-{5-Azaspiro[2.3]hexan-5-yl}-4-methylpyrimidin-5-yl)methanol

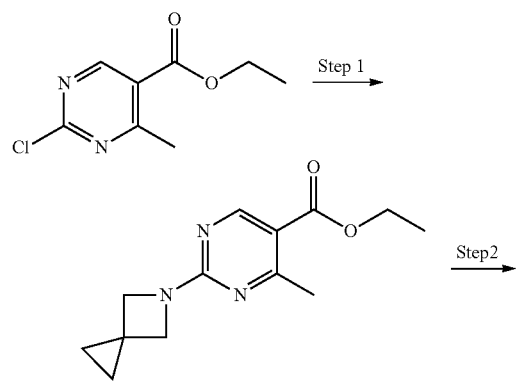

Intermediate 3 was prepared in analogy to Intermediate 2.

Starting materials Step 1: Ethyl-2-chloro-4-methylpyrimidine-5-carboxylate (1 g), 5-azaspiro[2.3]hexane trifluoroacetate (1.1 g), $K_2CO_3$ (1.45 g) in DMF (10 mL).

LC (Method 1): $t_R$=1.00 min; Mass spectrum (ESI$^+$): m/z=248 [M+H]$^+$.

Starting materials Step 2: Ethyl 2-{5-azaspiro[2.3]hexan-5-yl}-4-methylpyrimidine-5-carboxylate (0.659 g), diisobutylaluminiumhydride (7 mL, 1M solution in THF) in 5 mL THF.

LC (Method 1): $t_R$=0.60 min; Mass spectrum (ESI$^+$): m/z=206 [M+H]$^+$.

Intermediate 4

(6-{3-azabicyclo[3.1.0]hexan-3-yl}pyridin-3-yl)methanol

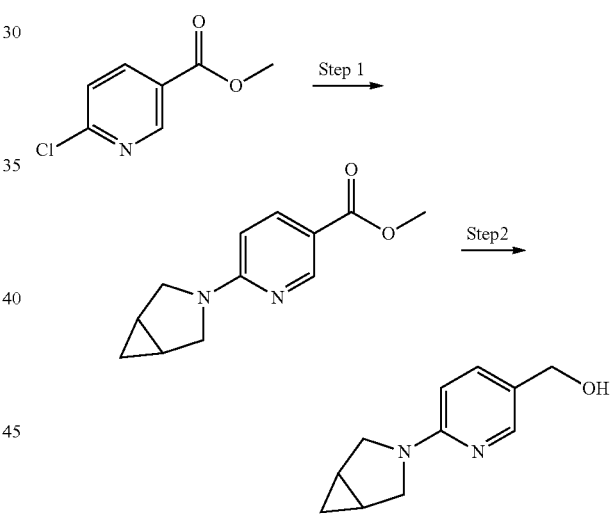

Step 1: Methyl 6-{3-azabicyclo[3.1.0]hexan-3-yl}pyridine-3-carboxylate

Methyl 6-chloropyridine-3-carboxylate (3.0 g), 3-azabicyclo[3.1.0]hexane hydrochloride (2.93 g) and $K_2CO_3$ (7.25 g) are suspended in DMF (20 mL) and heated to 90° C. for 16 h. The mixture is cooled, poured into water, stirred for 1 h and the precipitate is filtered off and dried to give the title compound.

LC (Method 1): $t_R$=0.68 min; Mass spectrum (ESI$^+$): m/z=219 [M+H]$^+$.

Step 2: (6-{3-azabicyclo[3.1.0]hexan-3-yl}pyridin-3-yl)methanol

To a solution of methyl 6-{3-azabicyclo[3.1.0]hexan-3-yl}pyridine-3-carboxylate (3.3 g) in THF (25 mL) is added LiBH₄ (8.32 mL; 2 M solution in THF) and MeOH (1.22 mL). The mixture is stirred for 16 h at 65° C. and concentrated in vacuo. Water is added to the residue, extracted with DCM and concentrated in vacuo. The crude is chromatographed over silica gel (EtOAc/MeOH 65:35→30:70). The solvents are evaporated in vacuo to give the title compound. LC (Method 1): $t_R$=0.52 min; Mass spectrum (ESI⁺): m/z=190 [M+H]⁺.

Intermediate 5

(5-bromo-6-{6,6-difluoro-3-azabicyclo[3.1.0]hexan-3-yl}pyridin-3-yl)methanol

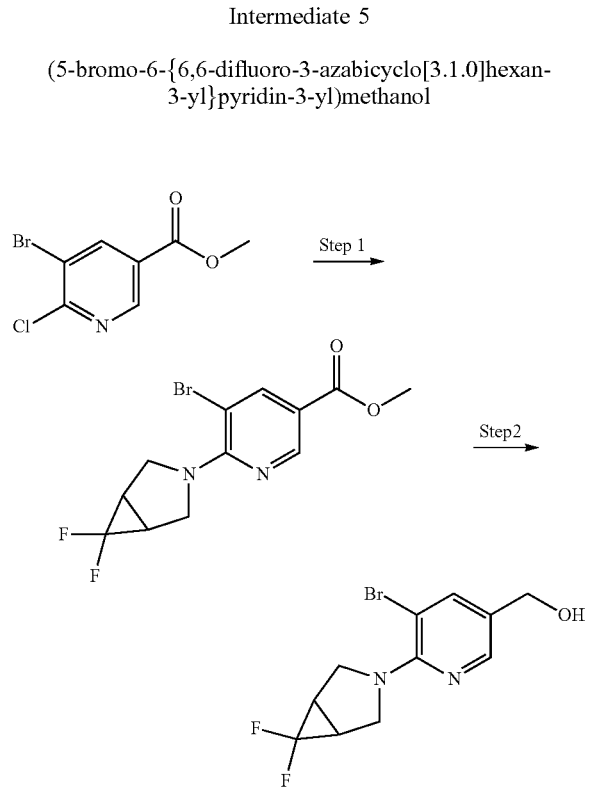

Step 1: Methyl 5-bromo-6-{6,6-difluoro-3-azabicyclo[3.1.0]hexan-3-yl}pyridine-3-carboxylate Methyl 5-bromo-6-chloropyridine-3-carboxylate (2.0 g), 6,6-difluoro-3-azabicyclo[3.1.0]hexane hydrochloride (1.36 g) and K₂CO₃ (3.3 g) are suspended in DMF (30 mL) and heated to 50° C. for 2 h. The mixture is cooled, poured into water, stirred for 1 h and the precipitate is filtered off and dried to give the title compound.

LC (Method 1): $t_R$=1.13 min; Mass spectrum (ESI⁺): m/z=333 [M+H]⁺.

Step 2: (5-bromo-6-{6,6-difluoro-3-azabicyclo[3.1.0]hexan-3-yl}pyridin-3-yl)methanol To a solution of methyl 5-bromo-6-{6,6-difluoro-3-azabicyclo[3.1.0]hexan-3-yl}pyridine-3-carboxylate (2.4 g) in THF (30 mL) is added LiBH₄ (10.8 mL; 2M solution in THF) and MeOH (1.74 mL). The mixture is stirred for 1 h at rt and 3 h at 50° C. After cooling to rt, K₂CO₃ solution (10% in water) is added and concentrated in vacuo. EtOAc is added to the residue, washed with water, dried with MgSO₄ and concentrated in vacuo to give the title compound.

LC (Method 1): $t_R$=0.84 min; Mass spectrum (ESI⁺): m/z=305 [M+H]⁺.

Intermediate 6

(1R,5S,6R)-6-(methoxymethyl)-3-azabicyclo[3.1.0]hexane

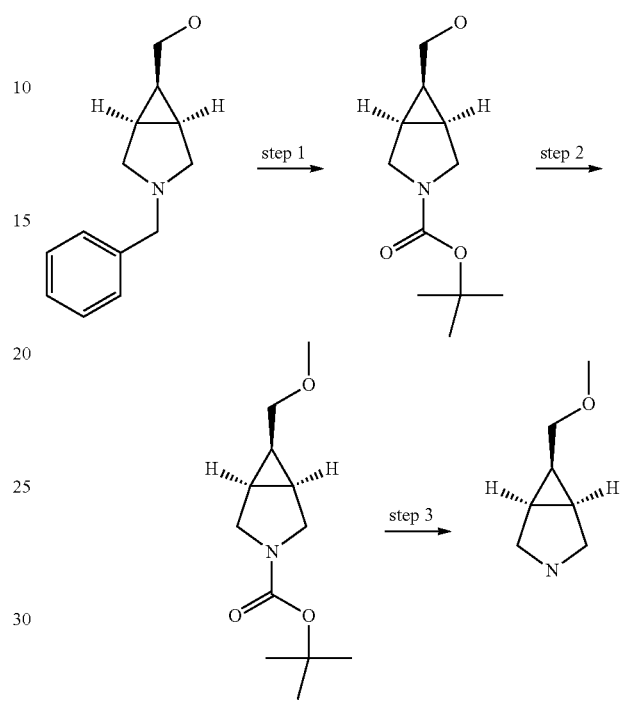

Step 1: Tert-butyl (1R,5S,6S)-6-(hydroxymethyl)-3-azabicyclo[3.1.0]hexane-3-carboxylate

[(1R,5S,6S)-3-benzyl-3-azabicyclo[3.1.0]hexan-6-yl]methanol (1.39 g) is dissolved in EtOH (50 mL), di-tert-butyl dicarbonate (1.55 g) and Pd/C (10%; 730 mg) are added and the mixture is shaked for 6 h under 50 psi hydrogen pressure. The mixture is filtered and concentrated in vacuo to give the title compound.

LC (Method 8): $t_R$=0.82 min; Mass spectrum (ESI⁺): m/z=214 [M+H]⁺.

Step 2: Tert-butyl (1R,5S,6S)-6-(methoxymethyl)-3-azabicyclo[3.1.0]hexane-3-carboxylate Tert-butyl (1R,5S,6S)-6-(hydroxymethyl)-3-azabicyclo[3.1.0]hexane-3-carboxylate (300 mg) is dissolved in DMF (3 mL), sodium hydride (60%; 61 mg) is added, stirred at rt for 30 min, methyliodide (2 M solution in t-butyl-methylether; 2.1 mL) is added and stirred for 3 d at rt. Ammoniumchloride solution is added to the mixture, extracted with EtOAc, the organic phase washed with brine, dried (MgSO₄) and concentrated in vacuo to give the title compound.

Mass spectrum (ESI⁺): m/z=228 [M+H]⁺.

Step 3: (1R,5S,6R)-6-(methoxymethyl)-3-azabicyclo[3.1.0]hexane

Tert-butyl (1R,5S,6S)-6-(methoxymethyl)-3-azabicyclo[3.1.0]hexane-3-carboxylate (531 mg) is dissolved in DCM (4 mL), TFA (1 mL) is added, stirred at rt for 2 h and concentrated in vacuo to give the title compound.

Mass spectrum (ESI⁺): m/z=128 [M+H]⁺.

Intermediate 7

[5-chloro-4-fluoro-2-(1H-1,2,3,4-tetrazol-1-yl)phenyl]methanamine

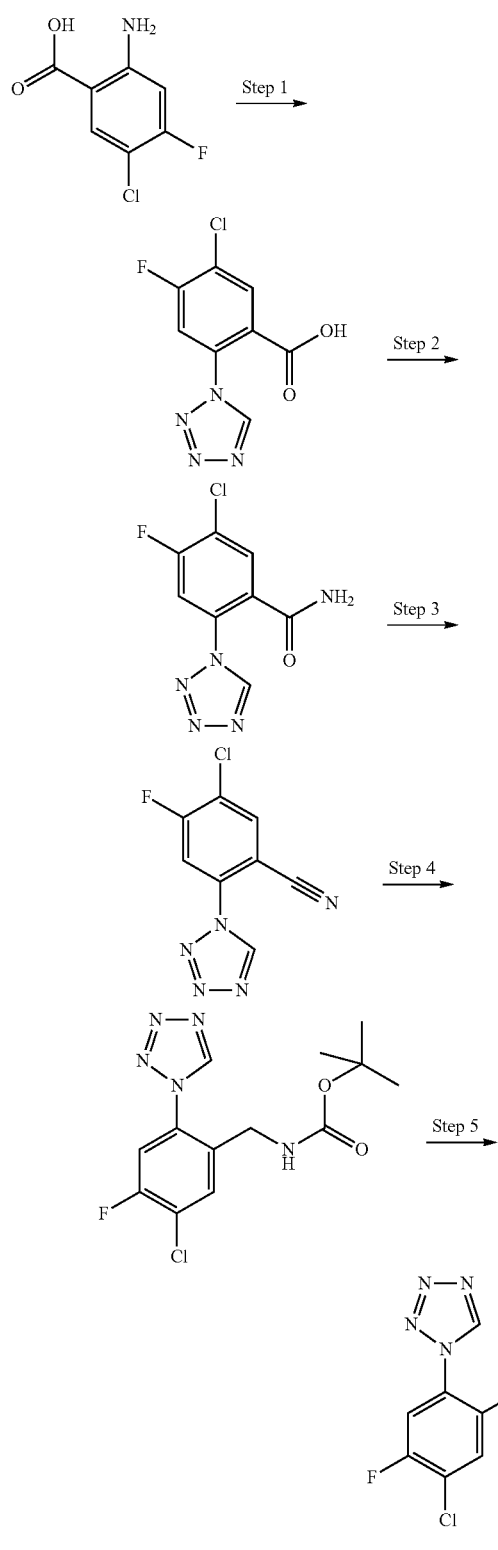

Step 1: 5-chloro-4-fluoro-2-(1H-1,2,3,4-tetrazol-1-yl)benzoic acid

To 2-amino-5-chloro-4-fluorobenzoic acid (40.0 g) in acetic acid (600 mL) are added sodium azide (41.2 g) and trimethyl orthoformate (67.1 g) and stirred for 2 h at rt. The mixture is poured into water (500 mL) and filtered to get the title compound.

TLC (DCM:MeOH 10:1): Rf=0.2

Step 2: 5-chloro-4-fluoro-2-(1H-1,2,3,4-tetrazol-1-yl)benzamide

A mixture of 5-chloro-4-fluoro-2-(1H-1,2,3,4-tetrazol-1-yl)benzoic acid (16.5 g), ammonium chloride (7.2 g), 1-ethyl-3-(3-dimethylaminopropyl)carbodiimide (18.4 g), N,N-diisopropylethylamine (26.3 g) and [1,2,3]Triazolo[4,5-b]pyridin-3-ol (18.5 g) in DMF (150 mL) is stirred at rt for 12 h. The mixture is poured into ammonium chloride (150 mL), extracted with EtOAc and the organic phase is concentrated. The crude product is purified by silica gel (petrol ether: EtOAc) to get the title compound.

TLC (petrol ether: EtOAc 1:1): Rf=0.2

Step 3: 5-chloro-4-fluoro-2-(1H-1,2,3,4-tetrazol-1-yl)benzonitrile

A mixture of 5-chloro-4-fluoro-2-(1H-1,2,3,4-tetrazol-1yl)benzamide (200 mg) and methyl N-(triethylammoniumsulfonyl)carbamate (240 mg) in THF (2 mL) is stirred at rt for 12 h and concentrated in vacuo. The crude product is purified by silica gel (petrol ether: EtOAc) to get the title compound.

TLC (petrol ether:EtOAc 1:1): Rf=0.7

Step 4: tert-butyl N-{[5-chloro-4-fluoro-2-(1H-1,2,3,4-tetrazol-1-yl)phenyl]methyl}carbamate A mixture of 5-chloro-4-fluoro-2-(1H-1,2,3,4-tetrazol-1-yl)benzonitrile (3.4 g), nickel (500 mg) and di-tert-butyl dicarbonate (4.0 g) in MeOH (50 mL) is stirred at rt for 5 h under 15 psi hydrogen pressure, filtered and concentrated in vacuo. The crude product is purified by silica gel (petrol ether:EtOAc) to get the title compound.

TLC (petrol ether:EtOAc 1:1): Rf=0.4

Step 5: [5-chloro-4-fluoro-2-(1H-1,2,3,4-tetrazol-1-yl)phenyl]methanamine

A mixture of tert-butyl N-{[5-chloro-4-fluoro-2-(1H-1,2,3,4-tetrazol-1-yl)phenyl]methyl}carbamate (1.2 g) in EtOAc;hydrochloride (10 mL) is stirred at rt for 2 h and concentrated in vacuo to get the title compound TLC (DCM:MeOH 10:1): Rf=0.1; Mass spectrum (ESI$^+$): m/z=228 [M+H]$^+$.

Intermediate 8

3-chloro-2-fluoro-6-(1H-1,2,3,4-tetrazol-1-yl)phenyl]methanamine

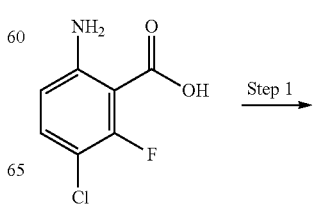

Step 1

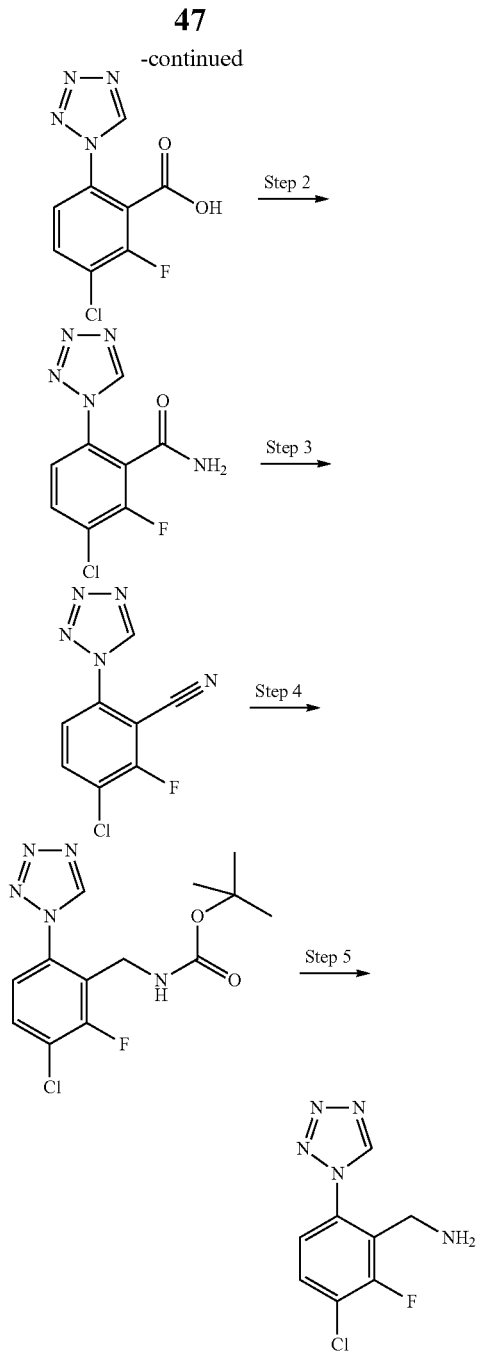

Step 1: 3-chloro-2-fluoro-6-(1H-1,2,3,4-tetrazol-1-yl)benzoic acid

To 6-amino-3-chloro-2-fluorobenzoic acid (50.0 g) in acetic acid (500 mL) are added sodium azide (51.4 g) and trimethyl orthoformate (83.9 g) and stirred for 12 h at rt. The mixture is poured into water (400 mL) and filtered to get the title compound.
TLC (DCM:MeOH 3:1): Rf=0.4

Step 2: 3-chloro-2-fluoro-6-(1H-1,2,3,4-tetrazol-1-yl)benzamide

A mixture of 3-chloro-2-fluoro-6-(1H-1,2,3,4-tetrazol-1-yl)benzoic acid (11.0 g), ammonium chloride (4.8 g), 1-ethyl-3-(3-dimethylaminopropyl)carbodiimide (12.2 g), N,N-diisopropylethylamine (17.5 g) and [1,2,3]Triazolo[4,5-b]pyridin-3-ol (12.3 g) in DMF (110 mL) is stirred at rt for 12 h. The mixture is poured into ammonium chloride (50 mL), extracted with EtOAc and the organic phase is concentrated. The crude product is purified by silica gel (petrol ether:EtOAc) to get the title compound.
TLC (petrol ether:EtOAc 1:1): Rf=0.2

Step 3: 3-chloro-2-fluoro-6-(1H-1,2,3,4-tetrazol-1-yl)benzonitrile

A mixture of 3-chloro-2-fluoro-6-(1H-1,2,3,4-tetrazol-1-yl)benzamide (6.0 g) and methyl N-(triethylammonium-sulfonyl)carbamate (7.1 g) in THF (60 mL) is stirred at rt for 12 h and concentrated in vacuo. The crude product is purified by silica gel (petrol ether:EtOAc) to get the title compound.
TLC (petrol ether:EtOAc 1:1): Rf=0.3

Step 4: tert-butyl N-{[3-chloro-2-fluoro-6-(1H-1,2,3,4-tetrazol-1-yl)phenyl]methyl}carbamate A mixture of 3-chloro-2-fluoro-6-(1H-1,2,3,4-tetrazol-1-yl)benzonitrile (4.0 g), nickel (1.0 g) and di-tert-butyl dicarbonate (4.7 g) in MeOH (100 mL) is stirred at rt for 5 h under 15 psi hydrogen pressure, filtered and concentrated in vacuo. The crude product is purified by silica gel (petrol ether:EtOAc) to get the title compound.
TLC (petrol ether:EtOAc 1:1): Rf=0.6

Step 5: [3-chloro-2-fluoro-6-(1H-1,2,3,4-tetrazol-1-yl)phenyl]methanamine

A mixture of tert-butyl N-{[3-chloro-2-fluoro-6-(1H-1,2,3,4-tetrazol-1-yl)phenyl]methyl}carbamate (550 mg) in EtOAc;hydrochloride (5 mL) is stirred at rt for 2 h and concentrated in vacuo to get the title compound
TLC (DCM:MeOH 10:1): Rf=0.1; Mass spectrum (ESI$^+$): m/z=228 [M+H]$^+$.

Intermediate 9

5-chloro-3-methyl-2-(1H-1,2,3,4-tetrazol-1-yl)phenyl]methanamine

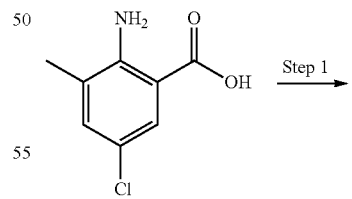

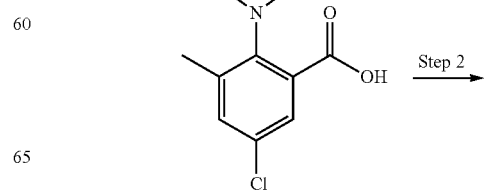

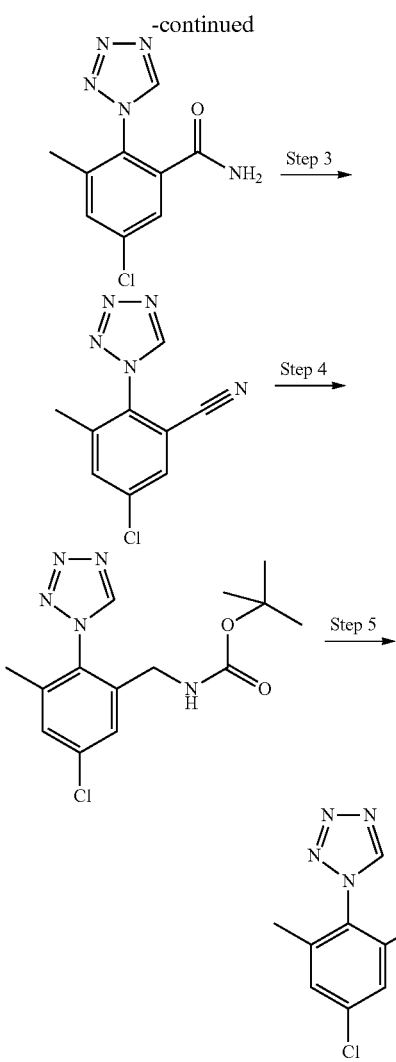

Step 1: 5-chloro-3-methyl-2-(1H-1,2,3,4-tetrazol-1-yl)benzoic acid

To 2-amino-5-chloro-3-methylbenzoic acid (20.0 g) in acetic acid (200 mL) are added sodium azide (21.0 g) and trimethyl orthoformate (34.3 g) and stirred for 12 h at rt. The mixture is poured into water (400 mL) and filtered to get the title compound.

TLC (DCM:MeOH 3:1): Rf=0.2

Step 2: 5-chloro-3-methyl-2-(1H-1,2,3,4-tetrazol-1-yl)benzamide

A mixture of 5-chloro-3-methyl-2-(1H-1,2,3,4-tetrazol-1-yl)benzoic acid (15.0 g), ammonium chloride (6.7 g), 1-ethyl-3-(3-dimethylaminopropyl)carbodiimide (17.0 g), N,N-diisopropylethylamine (24.3 g) and [1,2,3]Triazolo[4,5-b]pyridin-3-ol (17.1 g) in DMF (150 mL) is stirred at rt for 12 h. The mixture is poured into ammonium chloride (150 mL), extracted with EtOAc and the organic phase is concentrated. The crude product is purified by silica gel (petrol ether:EtOAc) to get the title compound.

TLC (petrol ether:EtOAc 1:1): Rf=0.4

Step 3: 5-chloro-3-methyl-2-(1H-1,2,3,4-tetrazol-1-yl)benzonitrile

A mixture of 5-chloro-3-methyl-2-(1H-1,2,3,4-tetrazol-1-yl)benzamide (5.0 g) and methyl N-(triethylammoniumsulfonyl)carbamate (7.5 g) in THF (50 mL) is stirred at rt for 12 h and concentrated in vacuo. The crude product is purified by silica gel (petrol ether:EtOAc) to get the title compound.

TLC (petrol ether:EtOAc 1:1): Rf=0.6

Step 4: tert-butyl N-{[5-chloro-3-methyl-2-(1H-1,2,3,4-tetrazol-1-yl)phenyl]methyl}carbamate A mixture of 5-chloro-3-methyl-2-(1H-1,2,3,4-tetrazol-1-yl)benzonitrile (4.0 g), nickel (4.0 g) and di-tert-butyl dicarbonate (4.8 g) in MeOH (40 mL) is stirred at rt for 5 h under 15 psi hydrogen pressure, filtered and concentrated in vacuo. The crude product is purified by silica gel (petrol ether:EtOAc) to get the title compound.

TLC (petrol ether:EtOAc 1:1): Rf=0.7

Step 5: [5-chloro-3-methyl-2-(1H-1,2,3,4-tetrazol-1-yl)phenyl]methanamine

A mixture of tert-butyl N-{[5-chloro-3-methyl-2-(1H-1,2,3,4-tetrazol-1-yl)phenyl]methyl}carbamate (500 mg) in EtOAc;hydrochloride (5 mL) is stirred at rt for 2 h and concentrated in vacuo to get the title compound TLC (DCM:MeOH 10:1): Rf=0.1; Mass spectrum (ESI$^+$): m/z=224 [M+H]$^+$.

Intermediate 10

1-[(6-{3-Azabicyclo[3.1.0]hexan-3-yl}-2-methylpyridin-3-yl)methyl]-1H-pyrazole-4-carboxylic acid

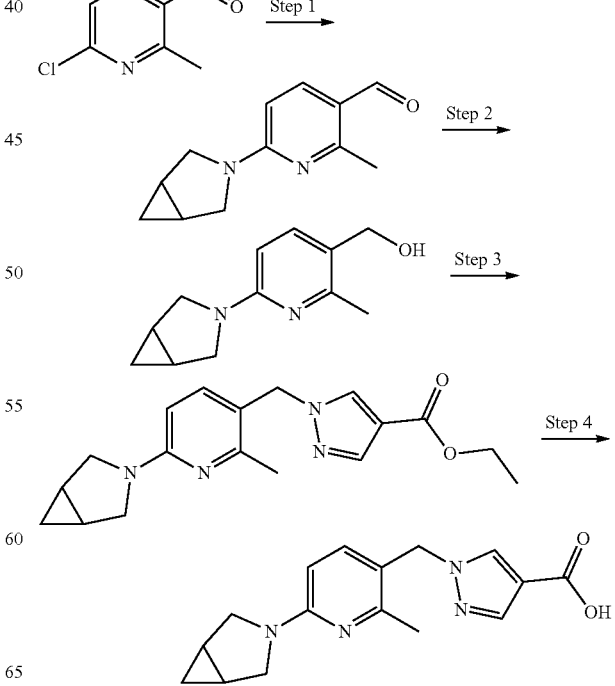

Step 1: 6-{3-Azabicyclo[3.1.0]hexan-3-yl}-2-methylpyridine-3-carbaldehyde

6-Chloro-2-methylpyridine-3-carbaldehyde (15 g), 3-azabicyclo[3.1.0]hexane hydrochloride (14 g) and KHCO₃ (22.5 g) are suspended in DMSO (70 mL) and heated to 60° C. for 12 h. The mixture is cooled, partitioned between water and DCM and the phases are separated. The aqueous phase is extracted three times with DCM and the combined organic phases are washed with brine. After drying (MgSO₄) the solvents are evaporated in vacuo to give the title compound.

LC (Method 1): $t_R$=0.59 min; Mass spectrum (ESI⁺): m/z=203 [M+H]⁺.

Step 2: (6-{3-Azabicyclo[3.1.0]hexan-3-yl}-2-methylpyridin-3-yl)methanol

To a solution of 6-{3-azabicyclo[3.1.0]hexan-3-yl}-2-methylpyridine-3-carbaldehyde (19.5 g) in EtOH (300 mL) is added under ice-cooling NaBH₄ (4 g). The mixture is stirred for 2 h at rt. After cooling to 0° C. the mixture is slowly treated with 4 M aqueous HCl (72 mL) and stirred for 15 min. Then the mixture is basified by addition of 4 M aqueous NaOH. EtOH is distilled off in vacuo. The residue is extracted with DCM. The organic phase is washed with brine and dried (MgSO₄). The solvents are evaporated in vacuo to give the title compound.

LC (Method 1): $t_R$=0.55 min; Mass spectrum (ESI⁺): m/z=205 [M+H]⁺.

Step 3: Ethyl 1-[(6-{3-azabicyclo[3.1.0]hexan-3-yl}-2-methylpyridin-3-yl)methyl]-1H-pyrazole-4-carboxylate (6-{3-Azabicyclo[3.1.0]hexan-3-yl}-2-methylpyridin-3-yl)methanol (19.2 g) is dissolved in THF (150 mL) and cooled to 0° C. Ethyl 1H-pyrazole-4-carboxylate (14.5 g) and tributyl phosphine (30 mL) are added. Di-tert.-butyl-azodicarboxylate (26 g) is slowly added portionwise and the mixture is stirred for 45 min. Saturated aqueous NaHCO₃ is added, the mixture is vigorously stirred for 10 min and then extracted with EtOAc. The organic phase is washed with brine, dried (MgSO₄) and concentrated in vacuo. The residue is chromatographed on silica gel (petrole ether:EtOAc 80:20→50:50) to give the title compound.

LC (Method 1): $t_R$=0.73 min; Mass spectrum (ESI⁺): m/z=327 [M+H]⁺.

Step 4: 1-[(6-{3-Azabicyclo[3.1.0]hexan-3-yl}-2-methylpyridin-3-yl)methyl]-1H-pyrazole-4-carboxylic acid A mixture of ethyl 1-[(6-{3-azabicyclo[3.1.0]hexan-3-yl}-2-methylpyridin-3-yl)methyl]-1H-pyrazole-4-carboxylate (15.5 g), 1 M KOH in EtOH (100 mL) and THF (250 mL) is stirred at 50° C. for 48 h. After cooling to rt acetic acid (5.5 mL) is added and the solvents are evaporated in vacuo. The residue is partitioned between water and DCM/isopropanol 9:1. The organic phase is washed with brine and dried (MgSO₄). The solvents are evaporated in vacuo and the residue is crystallized from ACN to give the title compound.

LC (Method 1): $t_R$=0.60 min; Mass spectrum (ESI⁺): m/z=299 [M+H]⁺.

Intermediate 11

1-[(6-{6,6-Difluoro-3-azabicyclo[3.1.0]hexan-3-yl}-2-methylpyridin-3-yl)methyl]-1H-pyrazole-4-carboxylic acid

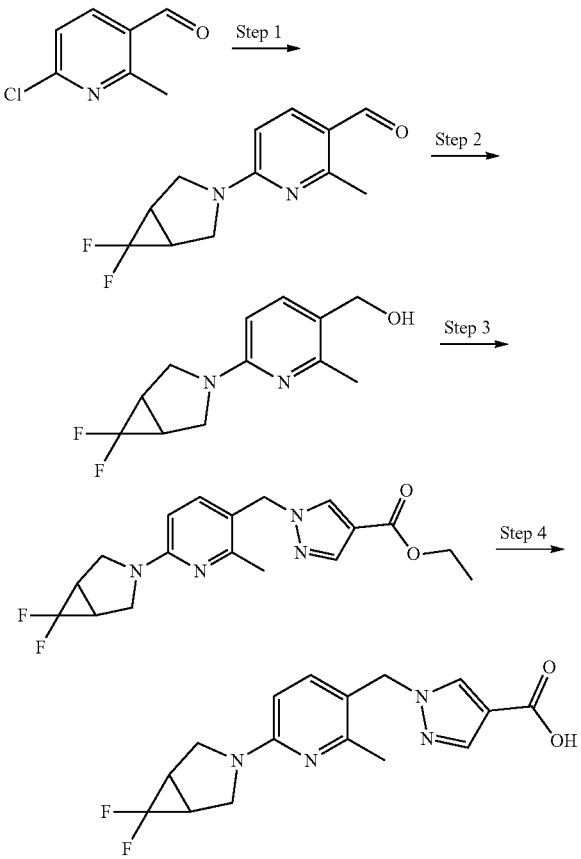

Step 1: 6-{6,6-Difluoro-3-azabicyclo[3.1.0]hexan-3-yl}-2-methylpyridine-3-carbaldehyde 6-Chloro-2-methylpyridine-3-carbaldehyde (19.6 g), 6,6-difluoro-3-azabicyclo[3.1.0]hexane hydrochloride (19.6 g) and KHCO₃ (58 g) are suspended in DMSO (70 mL) and heated to 75° C. for 48 h. The mixture is cooled, partitioned between water and EtOAc and the phases are separated. The organic phase is washed with brine. After drying (MgSO₄) the solvents are evaporated in vacuo to give the title compound.

LC (Method 1): $t_R$=0.66 min; Mass spectrum (ESI⁺): m/z=239 [M+H]⁺.

Step 2: (6-{6,6-Difluoro-3-azabicyclo[3.1.0]hexan-3-yl}-2-methylpyridin-3-yl)methanol To a solution 6-{6,6-difluoro-3-azabicyclo[3.1.0]hexan-3-yl}-2-methylpyridine-3-carbaldehyde (41.6 g) in EtOH (600 mL) is added under ice-cooling NaBH₄ (9 g). The mixture is stirred for 12 h at rt. After cooling to 0° C. the mixture is slowly treated with 4 M aqueous HCl (150 mL) and stirred for 15 min. Then the mixture is basified by addition of 4 M aqueous NaOH. EtOH is distilled off in vacuo. The residue is extracted with DCM. The organic phase is washed with brine and dried (MgSO₄). The solvents are evaporated in vacuo and the residue is triturated from diisopropylether to give the title compound.

LC (Method 1): $t_R$=0.54 min; Mass spectrum (ESI⁺): m/z=241 [M+H]⁺.

Step 3: Ethyl 1-[(6-{6,6-difluoro-3-azabicyclo[3.1.0]hexan-3-yl}-2-methylpyridin-3-yl)methyl]-1H-pyrazole-4-carboxylate (6-{6,6-Difluoro-3-azabicyclo[3.1.0]hexan-3-yl}-2-methylpyridin-3-yl)methanol (24.4 g) is dissolved in THF (500 mL) and cooled to 0° C. Ethyl 1H-pyrazole-4-carboxylate (15.3 g), tributyl phosphine (28 mL) are added. Di-tert.-butyl-azodicarboxylate (24.6 g) is slowly added portionwise and the mixture is stirred for 45 min. Saturated aqueous NaHCO₃ is added, the mixture is vigorously stirred for 10 min and then extracted with EtOAc. The organic phase is washed with brine, dried (MgSO₄) and concentrated in vacuo. The residue is chromatographed on silica gel (cyclohexane:EtOAc 50:50→20:80) to give the title compound.

LC (Method 1): $t_R$=0.75 min; Mass spectrum (ESI⁺): m/z=363 [M+H]⁺.

Step 4: 1-[(6-{6,6-Difluoro-3-azabicyclo[3.1.0]hexan-3-yl}-2-methylpyridin-3-yl)methyl]-1H-pyrazole-4-carboxylic acid A mixture of ethyl 1-[(6-{6,6-difluoro-3-azabicyclo[3.1.0]hexan-3-yl}-2-methylpyridin-3-yl)methyl]-1H-pyrazole-4-carboxylate (24.5 g), 4 M aqueous NaOH (30 mL) and EtOH (220 mL) is stirred at 60° C. for 4 h. After cooling to rt 4 M aqueous HCl (30 mL) is added and the solvents are evaporated in vacuo. The residue is taken up in water. The precipitate is isolated by filtration to give the title compound.

LC (Method 1): $t_R$=0.61 min; Mass spectrum (ESI⁺): m/z=335 [M+H]⁺.

Intermediate 12

Methyl 7-[(6-{6,6-difluoro-3-azabicyclo[3.1.0]hexan-3-yl}-2-methylpyridin-3-yl)methyl]-7H-pyrrolo[2,3-d]pyrimidine-5-carboxylate

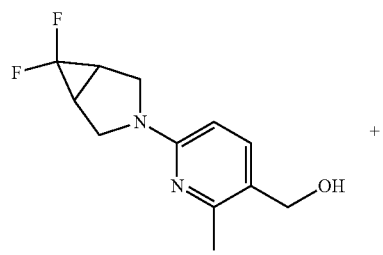

+

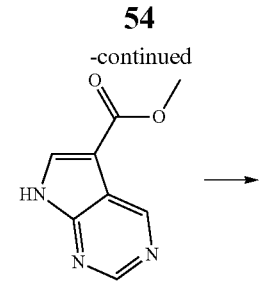

→

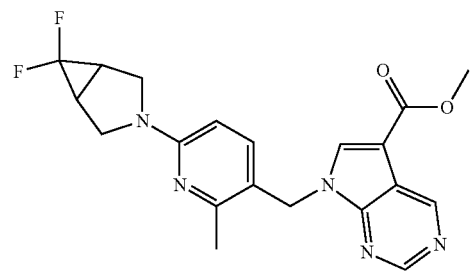

(6-{6,6-Difluoro-3-azabicyclo[3.1.0]hexan-3-yl}-2-methylpyridin-3-yl)methanol (150 mg) is dissolved in THF (8 mL) and cooled to −10° C. Methyl 7H-pyrrolo[2,3-d]pyrimidine-5-carboxylate (120 mg), tributyl phosphine (585 µL) are added. Di-tert.-butyl-azodicarboxylate (480 mg) is slowly added portionwise and the mixture is stirred at rt until completion of the reaction. Water is added and the mixture is extracted with EtOAc. The organic phase is washed with brine, dried (MgSO₄) and concentrated in vacuo. The residue is chromatographed on silica gel (petrole ether:EtOAc 80:20→0:100) to give the title compound.

LC (Method 1): $t_R$=0.67 min; Mass spectrum (ESI⁺): m/z=400 [M+H]⁺.

Intermediates 13-40 are prepared in analogy to Intermediate 12:

| Intermediate | Structure | $t_R$ | Mass spectrum (ESI+): m/z [M + H]⁺ | LC Method |
|---|---|---|---|---|
| 13 | 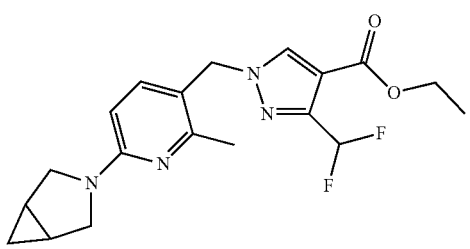 [SMILES: CCOC(=O)c1cn(Cc2ccc(N3CC4CC4C3)nc2C)nc1C(F)F] | 1.14 | 377 | Method 2 |

-continued

| Intermediate | Structure | $r_R$ | Mass spectrum (ESI+): m/z [M + H]+ | LC Method |
|---|---|---|---|---|
| 14 | 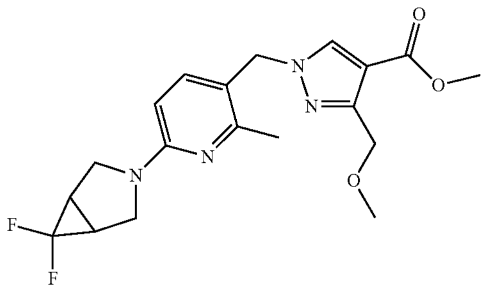 | 0.73 | 393 | Method 1 |
| 15 | 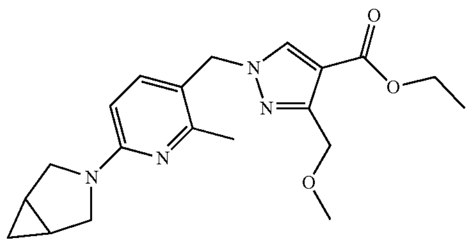 [SMILES: CCOC(=O)c1cn(Cc2ccc(N3CC4CC4C3)nc2C)nc1COC] | 0.71 | 357 | Method 1 |
| 16 | 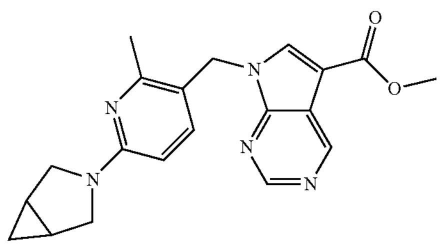 [SMILES: COC(=O)c1cn(Cc2ccc(N3CC4CC4C3)nc2C)c2ncncc12] | 0.65 | 364 | Method 1 |
| 17 | 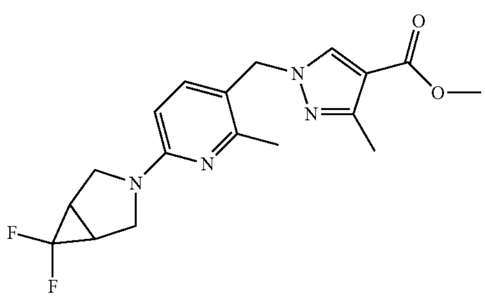 [SMILES: COC(=O)c1cn(Cc2ccc(N3CC4C(C3)C4(F)F)nc2C)nc1C] | 0.74 | 363 | Method 1 |
| 18 | 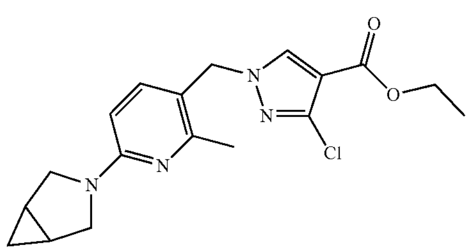 [SMILES: CCOC(=O)c1cn(Cc2ccc(N3CC4CC4C3)nc2C)nc1Cl] | 1.12 | 361 | Method 2 |
| 19 | 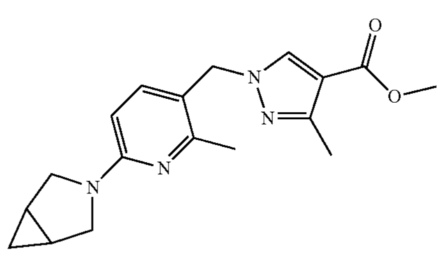 [SMILES: COC(=O)c1cn(Cc2ccc(N3CC4CC4C3)nc2C)nc1C] | 0.73 | 327 | Method 1 |

-continued
| Intermediate | Structure | $r_R$ | Mass spectrum (ESI+): m/z [M + H]⁺ | LC Method |
|---|---|---|---|---|
| 20 | 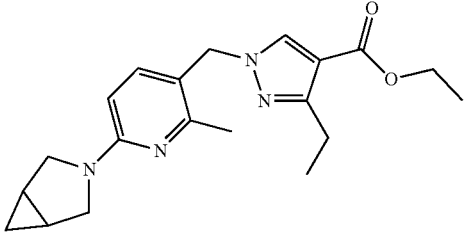 [SMILES: CCOC(=O)c1cn(Cc2ccc(N3CC4CC4C3)nc2C)nc1CC] | 1.09 | 357 | Method 2 |
| 21 | 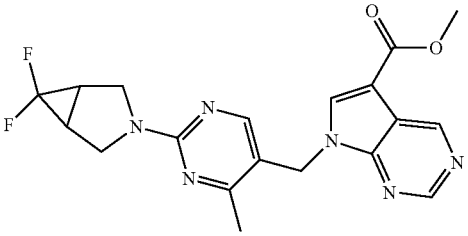 [SMILES: COC(=O)c1cn(Cc2cnc(N3CC4C(C3)C4(F)F)nc2C)c2ncncc12] | 0.84 | 401 | Method 1 |
| 22 | 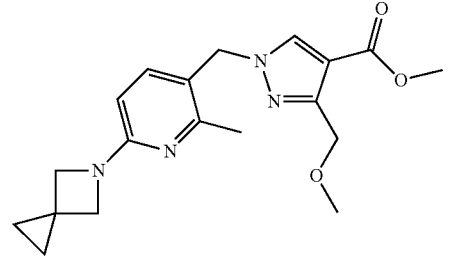 [SMILES: COCc1nn(Cc2ccc(N3CC4(CC4)C3)nc2C)cc1C(=O)OC] | 0.73 | 357 | Method 1 |
| 23 | 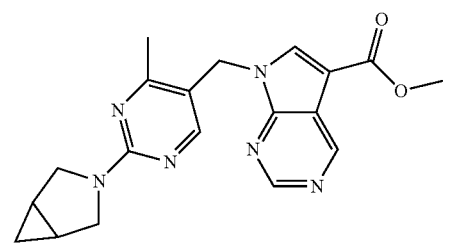 [SMILES: COC(=O)c1cn(Cc2cnc(N3CC4CC4C3)nc2C)c2ncncc12] | 0.77 | 365 | Method 1 |
| 24 | 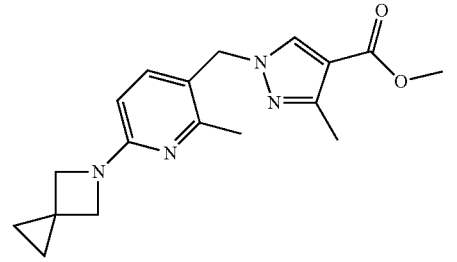 [SMILES: COC(=O)c1cn(Cc2ccc(N3CC4(CC4)C3)nc2C)nc1C] | 0.74 | 327 | Method 1 |
| 25 | 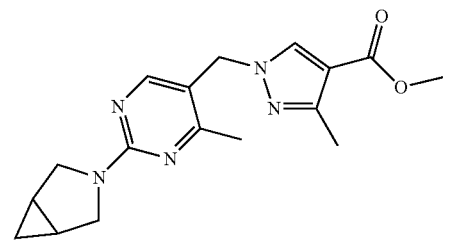 | 0.82 | 328 | Method 1 |

-continued

| Intermediate | Structure | $r_R$ | Mass spectrum (ESI+): m/z [M + H]+ | LC Method |
|---|---|---|---|---|
| 26 | 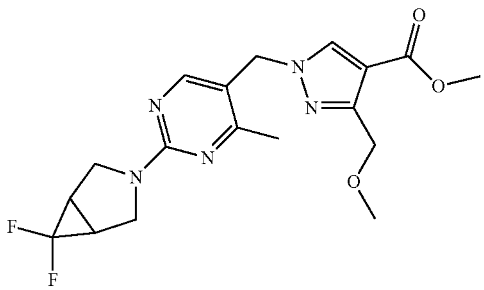 [SMILES: COCc1nn(Cc2cnc(N3CC4C(C3)C4(F)F)nc2C)cc1C(=O)OC] | 0.89 | 394 | Method 1 |
| 27 | 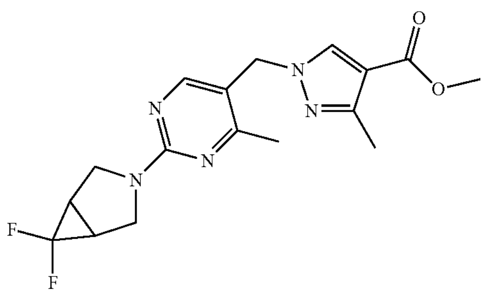 [SMILES: COC(=O)c1cn(Cc2cnc(N3CC4C(C3)C4(F)F)nc2C)nc1C] | 0.92 | 364 | Method 1 |
| 28 | 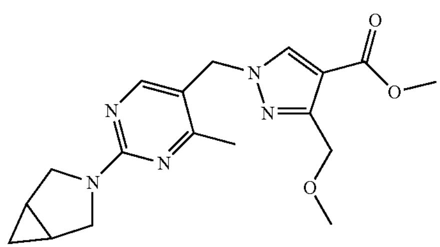 [SMILES: COCc1nn(Cc2cnc(N3CC4CC4C3)nc2C)cc1C(=O)OC] | 0.80 | 358 | Method 1 |
| 29 | 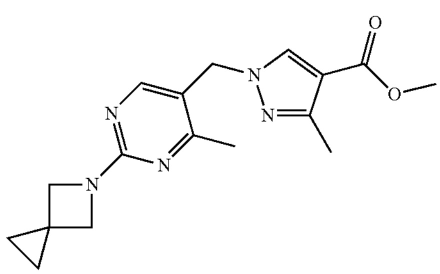 [SMILES: COC(=O)c1cn(Cc2cnc(N3CC4(CC4)C3)nc2C)nc1C] | 0.81 | 328 | Method 1 |
| 30 | 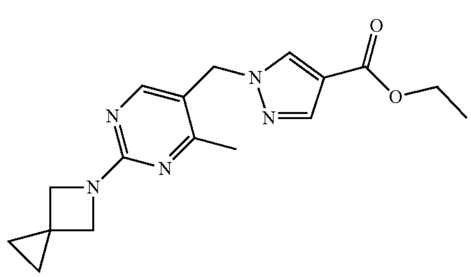 [SMILES: CCOC(=O)c1cnn(Cc2cnc(N3CC4(CC4)C3)nc2C)c1] | 0.95 | 328 | Method 2 |

-continued
| Intermediate | Structure | $r_R$ | Mass spectrum (ESI+): m/z [M + H]+ | LC Method |
|---|---|---|---|---|
| 31 | 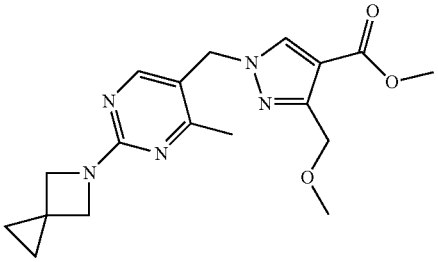 [SMILES: COCc1nn(Cc2cnc(N3CC4(CC4)C3)nc2C)cc1C(=O)OC] | 0.79 | 358 | Method 1 |
| 32 | 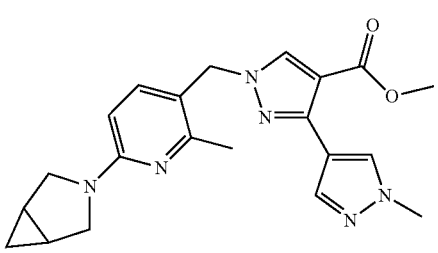 [SMILES: COC(=O)c1cn(Cc2ccc(N3CC4CC4C3)nc2C)nc1-c1cnn(C)c1] | 1.03 | 393 | Method 2 |
| 33 | 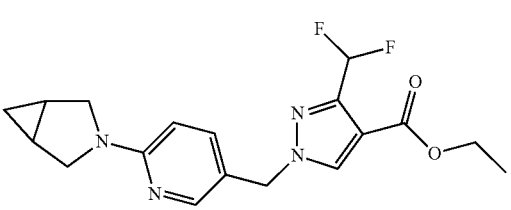 [SMILES: CCOC(=O)c1cn(Cc2ccc(N3CC4CC4C3)nc2)nc1C(F)F] | 1.06 | 363 | Method 2 |
| 34 | 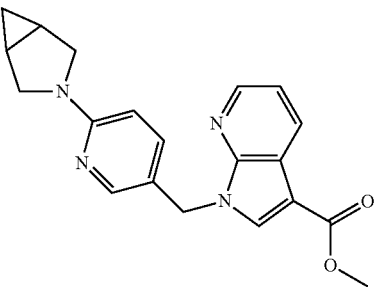 [SMILES: COC(=O)c1cn(Cc2ccc(N3CC4CC4C3)nc2)c2ncccc12] | 1.05 | 349 | Method 2 |
| 35 | 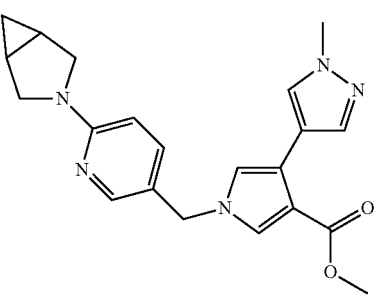 [SMILES: COC(=O)c1cn(Cc2ccc(N3CC4CC4C3)nc2)cc1-c1cnn(C)c1] | 0.95 | 379 | Method 2 |

-continued

| Intermediate | Structure | $r_R$ | Mass spectrum (ESI+): m/z [M + H]⁺ | LC Method |
|---|---|---|---|---|
| 36 | 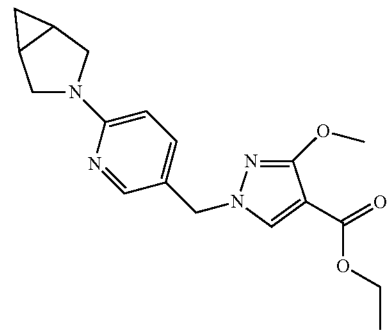 [SMILES: CCOC(=O)c1cn(Cc2ccc(N3CC4CC4C3)nc2)nc1OC] | 1.00 | 343 | Method 2 |
| 37 | 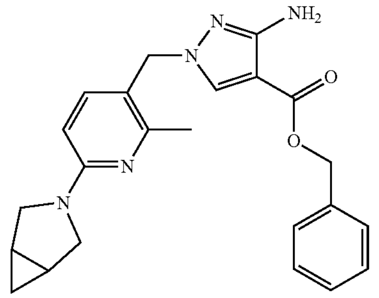 [SMILES: Cc1nc(N2CC3CC3C2)ccc1Cn1cc(C(=O)OCc2ccccc2)c(N)n1] | 0.84 | 404 | Method 1 |
| 38 | 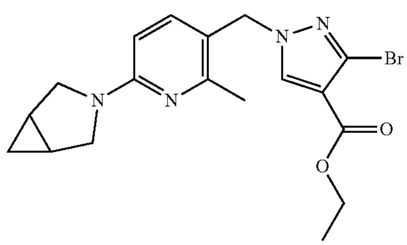 [SMILES: CCOC(=O)c1cn(Cc2ccc(N3CC4CC4C3)nc2C)nc1Br] | 1.14 | 405 | Method 2 |
| 39 | 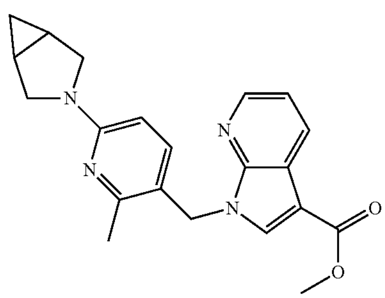 [SMILES: COC(=O)c1cn(Cc2ccc(N3CC4CC4C3)nc2C)c2ncccc12] | 1.14 | 363 | Method 2 |
| 40 | 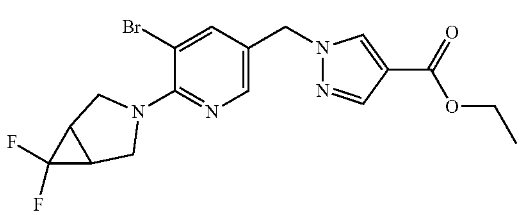 [SMILES: CCOC(=O)c1cnn(Cc2cnc(N3CC4C(C3)C4(F)F)c(Br)c2)c1] | 1.10 | 428 | Method 1 |

| Intermediate | Name | Name of starting material 1 | Name of starting material 2 |
|---|---|---|---|
| 13 | Ethyl 1-[(6-{3-azabicyclo[3.1.0]hexan-3-yl}-2-methylpyridin-3-yl)methyl]-3-(difluoromethyl)-1H-pyrazole-4-carboxylate | (6-{3-Azabicyclo[3.1.0]hexan-3-yl}-2-methyl-pyridin-3-yl)methanol | Ethyl 3-(difluoromethyl)-1H-pyrazole-4-carboxylate |
| 14 | Methyl 1-[(6-{6,6-difluoro-3-azabicyclo-[3.1.0]hexan-3-yl}-2-methylpyridin-3-yl)methyl]-3-(methoxy-methyl)-1H-pyrazole-4-carboxylate | (6-{6,6-Difluoro-3-azabicyclo[3.1.0]hexan-3-yl}-2-methylpyridin-3-yl)methanol | Methyl 3-(methoxy-methyl)-1H-pyrazole-4-carboxylate |
| 15 | Methyl 1-[(6-{3-azabicyclo[3.1.0]hexan-3-yl}-2-methylpyridin-3-yl)methyl]-3-(methoxymethyl)-1H-pyrazole-4-carboxylate | (6-{3-Azabicyclo[3.1.0]hexan-3-yl}-2-methyl-pyridin-3-yl)methanol | Methyl 3-(methoxy-methyl)-1H-pyrazole-4-carboxylate |
| 16 | Methyl 7-[(6-{3-azabicyclo[3.1.0]hexan-3-yl}-2-methylpyridin-3-yl)methyl]-7H-pyrrolo[2,3-d]pyrimidine-5-carboxylate | (6-{3-Azabicyclo[3.1.0]hexan-3-yl}-2-methyl-pyridin-3-yl)methanol | Methyl 7H-pyrrolo[2,3-d]-pyrimidine-5-carboxylate |
| 17 | Methyl 1-[(6-{6,6-difluoro-3-aza-bicyclo[3.1.0]hexan-3-yl}-2-methyl-pyridin-3-yl)methyl]-3-methyl-1H-pyrazole-4-carboxylate | (6-{6,6-Difluoro-3-aza-bicyclo[3.1.0]hexan-3-yl}-2-methylpyridin-3-yl)methanol | Methyl 3-methyl-1H-pyrazole-4-carboxylate |
| 18 | Ethyl 1-[(6-{3-Azabicyclo[3.1.0]hexan-3-yl}-2-methylpyridin-3-yl)methyl]-3-chloro-1H-pyrazole-4-carboxylate | (6-{3-Azabicyclo[3.1.0]hexan-3-yl}-2-methyl-pyridin-3-yl)methanol | Ethyl 3-chloro-1H-pyrazole-4-carboxylate |
| 19 | Methyl 1-[(6-{3-azabicyclo[3.1.0]hexan-3-yl}-2-methylpyridin-3-yl)methyl]-3-methyl-1H-pyrazole-4-carboxylate | (6-{3-Azabicyclo[3.1.0]hexan-3-yl}-2-methyl-pyridin-3-yl)methanol | Methyl 3-methyl-1H-pyrazole-4-carboxylate |
| 20 | Ethyl 1-[(6-{3-Azabicyclo[3.1.0]hexan-3-yl}-2-methylpyridin-3-yl)methyl]-3-methoxy-1H-pyrazole-4-carboxylate | (6-{3-Azabicyclo[3.1.0]hexan-3-yl}-2-methyl-pyridin-3-yl)methanol | Ethyl 3-methoxy-1H-pyrazole-4-carboxylate |
| 21 | Methyl 7-[(2-{6,6-difluoro-3-aza-bicyclo[3.1.0]hexan-3-yl}-4-methyl-pyrimidin-5-yl)methyl]-7H-pyrrolo[2,3-d]pyrimidine-5-carboxylate | (2-{6,6-Difluoro-3-aza-bicyclo[3.1.0]hexan-3-yl}-4-methylpyrimidin-5-yl)methanol | Methyl 7H-pyrrolo[2,3-d]pyrimidine-5-carboxylate |
| 22 | Methyl 1-[(6-{5-azaspiro[2.3]hexan-5-yl}-2-methylpyridin-3-yl)methyl]-3-(methoxymethyl)-1H-pyrazole-4-carboxylate | (6-{5-Azaspiro[2.3]-hexan-5-yl}-2-methyl-pyridin-3-yl)methanol | Methyl 3-(methoxy-methyl)-1H-pyrazole-4-carboxylate |
| 23 | Methyl 7-[(2-{3-azabicyclo[3.1.0]hexan-3-yl}-4-methylpyrimidin-5-yl)methyl]-7H-pyrrolo[2,3-d]pyrimidine-5-carboxylate | (2-{3-Azabicyclo[3.1.0]hexan-3-yl}-4-methyl-pyrimidin-5-yl)methanol | Methyl 7H-pyrrolo[2,3-d]-pyrimidine-5-carboxylate |
| 24 | Methyl 1-[(6-{5-azaspiro[2.3]hexan-5-yl}-2-methylpyridin-3-yl)methyl]-3-methyl-1H-pyrazole-4-carboxylate | (6-{5-Azaspiro[2.3]-hexan-5-yl}-2-methyl-pyridin-3-yl)methanol | Methyl 3-methyl-1H-pyrazole-4-carboxylate |
| 25 | Methyl 1-[(2-{3-azabicyclo[3.1.0]hexan-3-yl}-4-methylpyrimidin-5-yl)methyl]-3-methyl-1H-pyrazole-4-carboxylate | (2-{3-Azabicyclo[3.1.0]hexan-3-yl}-4-methyl-pyrimidin-5-yl)methanol | Methyl 3-methyl-1H-pyrazole-4-carboxylate |
| 26 | Methyl 1-[(2-{6,6-difluoro-3-aza-bicyclo[3.1.0]hexan-3-yl}-4-methyl-pyrimidin-5-yl)methyl]-3-(methoxy-methyl)-1H-pyrazole-4-carboxylate | (2-{6,6-Difluoro-3-aza-bicyclo[3.1.0]hexan-3-yl}-4-methylpyrimidin-5-yl)methanol | Methyl 3-(methoxy-methyl)-1H-pyrazole-4-carboxylate |
| 27 | Methyl 1-[(2-{6,6-difluoro-3-aza-bicyclo[3.1.0]hexan-3-yl}-4-methyl-pyrimidin-5-yl)methyl]-3-methyl-1H-pyrazole-4-carboxylate | (2-{6,6-Difluoro-3-aza-bicyclo[3.1.0]hexan-3-yl}-4-methylpyrimidin-5-yl)methanol | Methyl 3-methyl-1H-pyrazole-4-carboxylate |
| 28 | Methyl 1-[(2-{3-azabicyclo[3.1.0]hexan-3-yl}-4-methylpyrimidin-5-yl)methyl]-3-(methoxymethyl)-1H-pyrazole-4-carboxylate | (2-{3-Azabicyclo[3.1.0]hexan-3-yl}-4-methyl-pyrimidin-5-yl)methanol | Methyl 3-(methoxy-methyl)-1H-pyrazole-4-carboxylate |
| 29 | Methyl 1-[(2-{5-azaspiro[2.3]hexan-5-yl}-4-methylpyrimidin-5-yl)methyl]-3-methyl-1H-pyrazole-4-carboxylate | (2-{5-Azaspiro[2.3]-hexan-5-yl}-4-methyl-pyrimidin-5-yl)methanol | Methyl 3-methyl-1H-pyrazole-4-carboxylate |
| 30 | Ethyl 1-[(2-{5-azaspiro[2.3]hexan-5-yl}-4-methylpyrimidin-5-yl)methyl]-1H-pyrazole-4-carboxylate | (2-{5-Azaspiro[2.3]-hexan-5-yl}-4-methyl-pyrimidin-5-yl)methanol | Ethyl 1H-pyrazole-4-carboxylate |
| 31 | Methyl 1-[(2-{5-azaspiro[2.3]hexan-5-yl}-4-methylpyrimidin-5-yl)methyl]-3-(methoxymethyl)-1H-pyrazole-4-carboxylate | (2-{5-Azaspiro[2.3]-hexan-5-yl}-4-methyl-pyrimidin-5-yl)methanol | Methyl 3-(methoxy-methyl)-1H-pyrazole-4-carboxylate |
| 32 | Methyl 1-[(6-{3-azabicyclo[3.1.0]hexan-3-yl}-2-methylpyridin-3-yl)methyl]-3-(1-methyl-1H-pyrazol-4-yl)-1H-pyrazole-4-carboxylate | (6-{3-Azabicyclo[3.1.0]hexan-3-yl}-2-methyl-pyridin-3-yl)methanol | Methyl 3-(1-methyl-1H-pyrazol-4-yl)-1H-pyrazole-4-carboxylate |
| 33 | Ethyl 1-[(6-{3-azabicyclo[3.1.0]hexan-3-yl}pyridin-3-yl)methyl]-3-(difluoro-methyl)-1H-pyrazole-4-carboxylate | (6-{3-azabicyclo[3.1.0]hexan-3-yl}pyridin-3-yl)-methanol | Ethyl 3-(difluoromethyl)-1H-pyrazole-4-carboxylate |
| 34 | Methyl 1-[(6-{3-azabicyclo[3.1.0]hexan-3-yl}pyridin-3-yl)methyl]-1H-pyrrolo[2,3-b]pyridine-3-carboxylate | (6-{3-azabicyclo[3.1.0]hexan-3-yl}pyridin-3-yl)methanol | 1H-Pyrrolo[2,3-b]-pyridine-3-carboxylic acid methyl ester |

-continued

| Intermediate | Name | Name of starting material 1 | Name of starting material 2 |
|---|---|---|---|
| 35 | methyl 1-[(6-{3-azabicyclo[3.1.0]hexan-3-yl}pyridin-3-yl)methyl]-3-(1-methyl-1H-pyrazol-4-yl)-1H-pyrazole-4-carboxylate | (6-{3-azabicyclo[3.1.0]hexan-3-yl}pyridin-3-yl)methanol | Methyl 3-(1-methyl-1H-pyrazol-4-yl)-1H-pyrazole-4-carboxylate |
| 36 | Ethyl 1-[(6-{3-azabicyclo[3.1.0]hexan-3-yl}pyridin-3-yl)methyl]-3-methoxy-1H-pyrazole-4-carboxylate | (6-{3-azabicyclo[3.1.0]hexan-3-yl}pyridin-3-yl)methanol | Ethyl 3-methoxy-1H-pyrazole-4-carboxylate |
| 37 | Benzyl 3-amino-1-(6-{3-azabicyclo-[3.1.0]hexan-3-yl}-2-methylpyridin-3-yl)methyl]-1H-pyrazole-4-carboxylate | (6-{3-Azabicyclo[3.1.0]hexan-3-yl}-2-methyl-pyridin-3-yl)methanol | Benzyl 3-amino-1H-pyrazole-4-carboxylate |
| 38 | Ethyl 1-[(6-{3-azabicyclo[3.1.0]hexan-3-yl}-2-methylpyridin-3-yl)methyl]-3-bromo-1H-pyrazole-4-carboxylate | (6-{3-Azabicyclo[3.1.0]hexan-3-yl}-2-methyl-pyridin-3-yl)methanol | Ethyl 3-bromo-1H-pyrazole-4-carboxylate |
| 39 | Methyl 1-[(6-{3-azabicyclo[3.1.0]hexan-3-yl}-2-methylpyridin-3-yl)methyl]-1H-pyrrolo[2,3-b]pyridine-3-carboxylate | (6-{3-Azabicyclo[3.1.0]hexan-3-yl}-2-methyl-pyridin-3-yl)methanol | Methyl 1H-pyrrolo[2,3-b]pyridine-3-carboxylate |
| 40 | Ethyl 1-[(5-bromo-6-{6,6-difluoro-3-azabicyclo[3.1.0]hexan-3-yl}pyridin-3-yl)methyl]-1H-pyrazole-4-carboxylate | (5-bromo-6-{6,6-difluoro-3-azabicyclo[3.1.0]hexan-3-yl}pyridin-3-yl)methanol | Ethyl 1H-pyrazole-4-carboxylate |

Intermediate 40b

Methyl 3-(1-methyl-1H-pyrazol-4-yl)-1H-pyrazole-4-carboxylate 3-(1-Methyl-1H-pyrazol-4-yl)-1H-pyrazole-4-carboxylic acid (1 g) is dissolved in MeOH (50 mL), thionylchloride (3 mL) is added, stirred for 16 h at 50° C. and concentrated in vacuo. The residue is dissolved in MeOH, filtered through a PL-HCO$_3$ MP SPE cartridge, washed with MeOH and concentrated in vacuo to give the title compound.

LC (Method 1): $t_R$=0.73 min; Mass spectrum (ESI$^+$): m/z=207 (CI) [M+H]$^+$.

Intermediate 41

1-[(6-{3-Azabicyclo[3.1.0]hexan-3-yl}-2-methylpyridin-3-yl)methyl]-3-chloro-1H-pyrazole-4-carboxylic acid

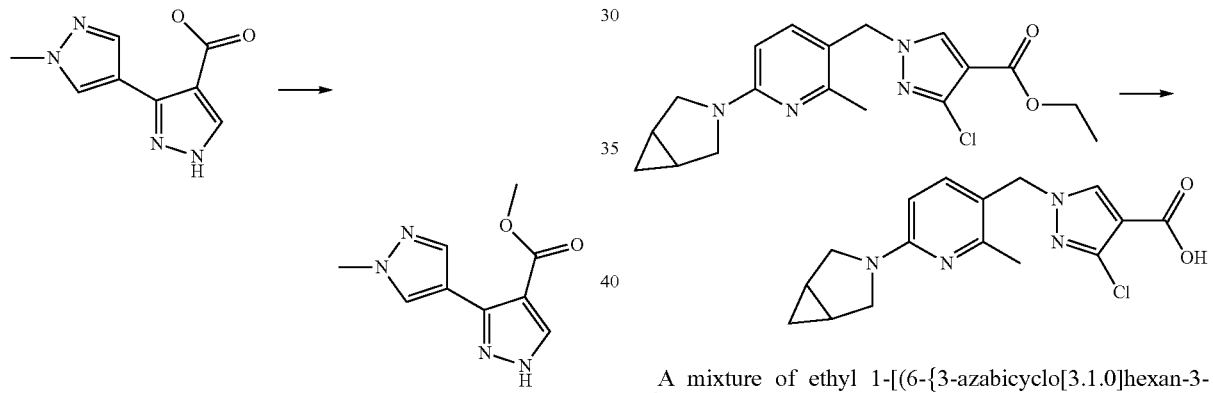

A mixture of ethyl 1-[(6-{3-azabicyclo[3.1.0]hexan-3-yl}-2-methylpyridin-3-yl)methyl]-3-chloro-1H-pyrazole-4-carboxylate (124 mg), 1 M NaOH in water (2 mL), EtOH (2 mL) and 1,4-dioxane (5 mL) is stirred at 50° C. for ~2 h. After cooling to rt 4 M aqueous HCl (0.5 mL) is added and the solvents are evaporated in vacuo to give the title compound (containing NaCl).

LC (Method 1): $t_R$=0.71 min; Mass spectrum (ESI$^+$): m/z=333/335 (CI) [M+H]$^+$.

Intermediates 42-69 are prepared in analogy to Intermediate 41:

| Intermediate | Structure | $t_R$ | Mass spectrum (ESI+): m/z [M + H]$^+$ | LC Method |
|---|---|---|---|---|
| 42 | 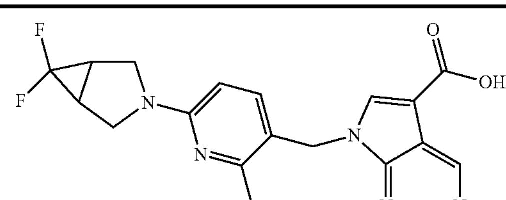 | 0.28 | 386 | Method 4 |

| Intermediate | Structure | $t_R$ | Mass spectrum (ESI+): m/z [M + H]+ | LC Method |
|---|---|---|---|---|
| 43 | 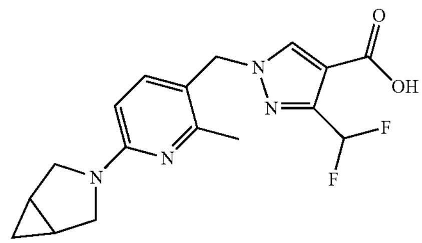 [SMILES: Cc1nc(N2CC3CC3C2)ccc1Cn1cc(C(=O)O)c(C(F)F)n1] | 0.72 | 349 | Method 1 |
| 44 | 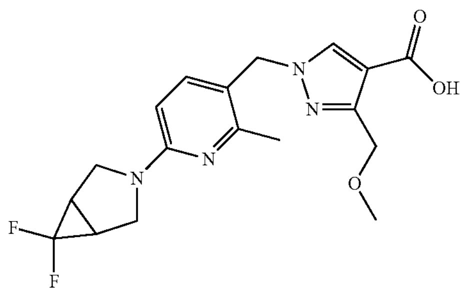 [SMILES: COCc1nn(Cc2ccc(N3CC4C(C3)C4(F)F)nc2C)cc1C(=O)O] | 0.31 | 379 | Method 4 |
| 45 | 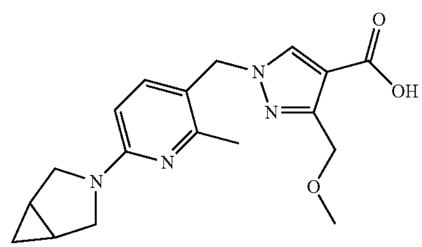 [SMILES: COCc1nn(Cc2ccc(N3CC4CC4C3)nc2C)cc1C(=O)O] | 0.67 | 343 | Method 1 |
| 46 | 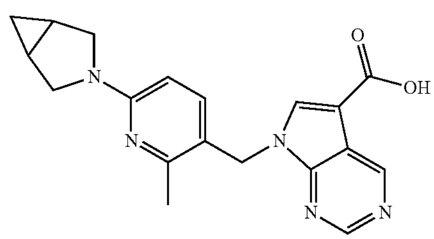 [SMILES: Cc1nc(N2CC3CC3C2)ccc1Cn1cc(C(=O)O)c2cncnc21] | 0.63 | 350 | Method 1 |
| 47 | 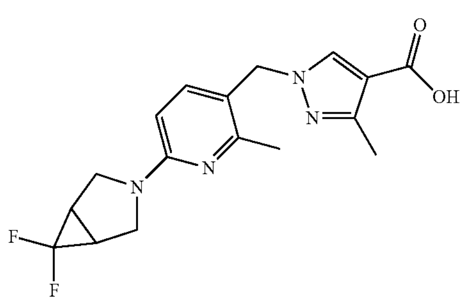 [SMILES: Cc1nc(N2CC3C(C2)C3(F)F)ccc1Cn1cc(C(=O)O)c(C)n1] | 0.32 | 349 | Method 4 |
| 48 | 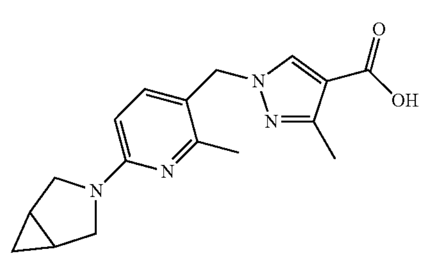 [SMILES: Cc1nc(N2CC3CC3C2)ccc1Cn1cc(C(=O)O)c(C)n1] | 0.68 | 313 | Method 1 |

-continued

| Intermediate | Structure | $t_R$ | Mass spectrum (ESI+): m/z [M + H]+ | LC Method |
|---|---|---|---|---|
| 49 | 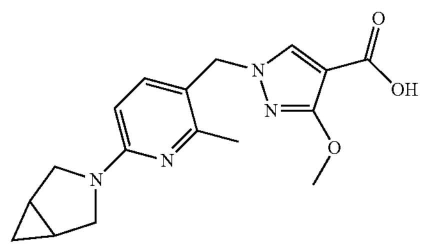 [SMILES: COc1nn(Cc2ccc(N3CC4CC4C3)nc2C)cc1C(=O)O] | 0.67 | 329 | Method 1 |
| 50 | 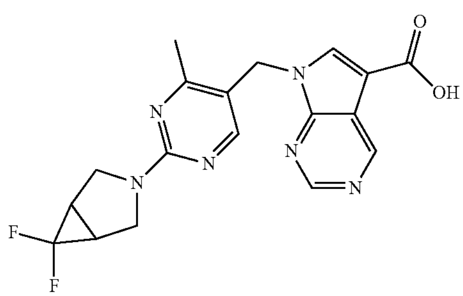 [SMILES: Cc1nc(N2CC3C(C2)C3(F)F)ncc1Cn1cc(C(=O)O)c2cncnc21] | 0.77 | 387 | Method 1 |
| 51 | 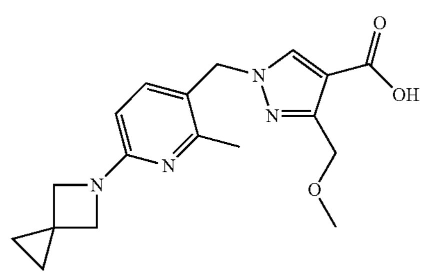 [SMILES: COCc1nn(Cc2ccc(N3CC4(CC4)C3)nc2C)cc1C(=O)O] | 0.32 | 343 | Method 4 |
| 52 | 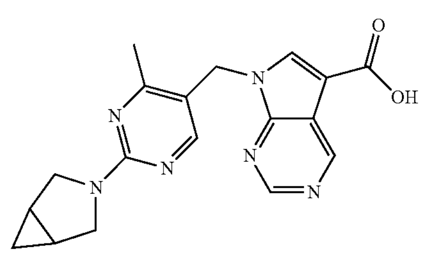 [SMILES: Cc1nc(N2CC3CC3C2)ncc1Cn1cc(C(=O)O)c2cncnc21] | 0.35 | 351 | Method 4 |
| 53 | 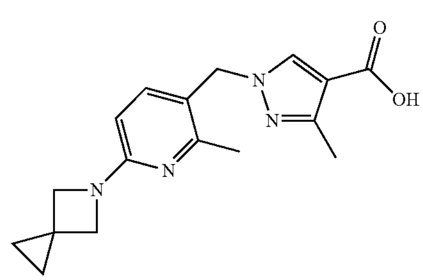 [SMILES: Cc1nc(N2CC3(CC3)C2)ccc1Cn1cc(C(=O)O)c(C)n1] | 0.33 | 313 | Method 4 |

-continued

| Intermediate | Structure | $t_R$ | Mass spectrum (ESI+): m/z [M + H]+ | LC Method |
|---|---|---|---|---|
| 54 | 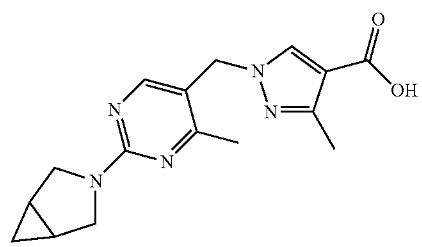 [SMILES: Cc1nc(N2CC3CC3C2)ncc1Cn1cc(C(=O)O)c(C)n1] | 0.39 | 314 | Method 4 |
| 55 | 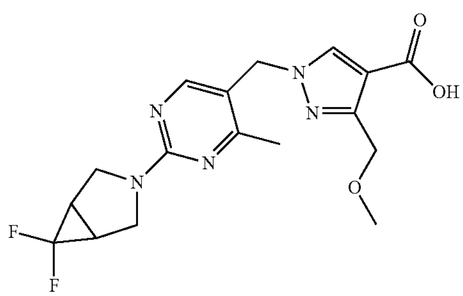 [SMILES: COCc1nn(Cc2cnc(N3CC4C(C3)C4(F)F)nc2C)cc1C(=O)O] | 0.47 | 380 | Method 4 |
| 56 | 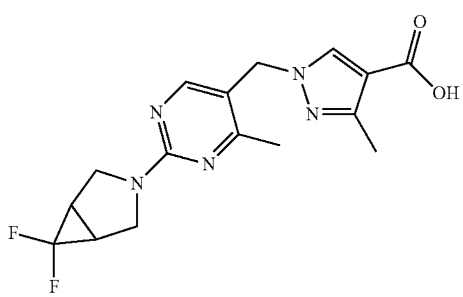 [SMILES: Cc1nc(N2CC3C(C2)C3(F)F)ncc1Cn1cc(C(=O)O)c(C)n1] | 0.48 | 350 | Method 4 |
| 57 | 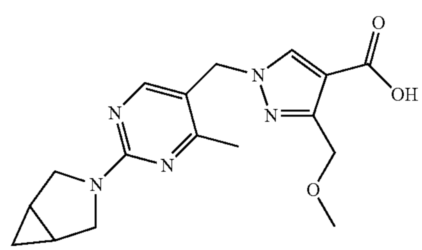 [SMILES: COCc1nn(Cc2cnc(N3CC4CC4C3)nc2C)cc1C(=O)O] | 0.74 | 344 | Method 1 |
| 58 | 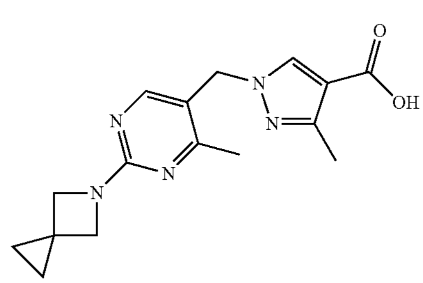 [SMILES: Cc1nc(N2CC3(CC3)C2)ncc1Cn1cc(C(=O)O)c(C)n1] | 0.39 | 314 | Method 4 |

-continued

| Intermediate | Structure | $t_R$ | Mass spectrum (ESI+): m/z [M + H]⁺ | LC Method |
| --- | --- | --- | --- | --- |
| 59 | 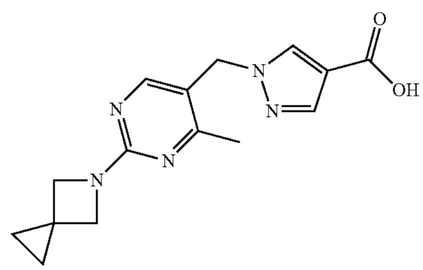 [SMILES: Cc1nc(N2CC3(CC3)C2)ncc1Cn1cc(C(=O)O)cn1] | 0.56 | 328 | Method 2 |
| 60 | 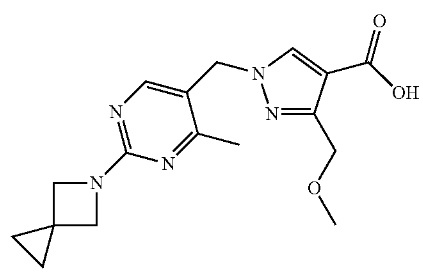 [SMILES: COCc1nn(Cc2cnc(N3CC4(CC4)C3)nc2C)cc1C(=O)O] | 0.38 | 344 | Method 4 |
| 61 | 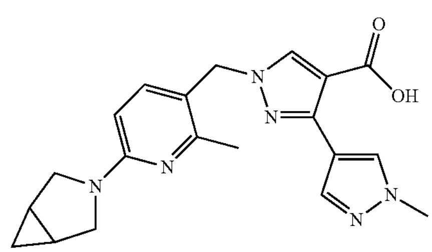 [SMILES: Cc1nc(N2CC3CC3C2)ccc1Cn1cc(C(=O)O)c(-c2cnn(C)c2)n1] | 0.70 | 379 | Method 1 |
| 62 | 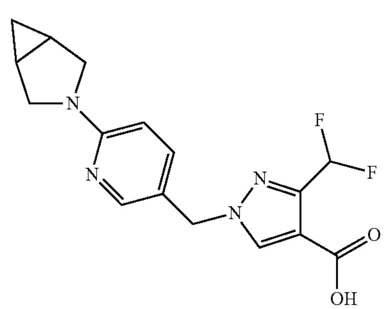 [SMILES: O=C(O)c1cn(Cc2ccc(N3CC4CC4C3)nc2)nc1C(F)F] | 0.71 | 335 | Method 1 |
| 63 | 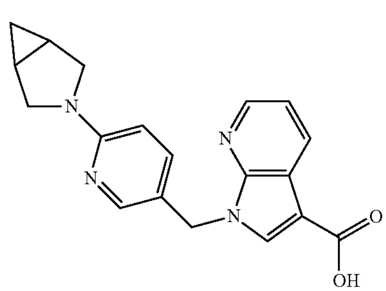 [SMILES: O=C(O)c1cn(Cc2ccc(N3CC4CC4C3)nc2)c2ncccc12] | 0.75 | 335 | Method 1 |

-continued

| Intermediate | Structure | $t_R$ | Mass spectrum (ESI+): m/z [M + H]+ | LC Method |
|---|---|---|---|---|
| 64 | 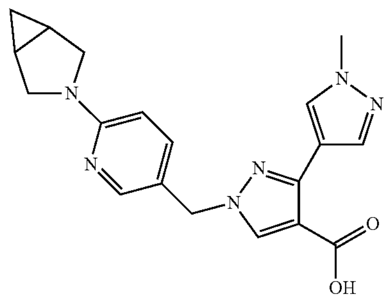 [SMILES: Cn1cc(-c2nn(Cc3ccc(N4CC5CC5C4)nc3)cc2C(=O)O)cn1] | 0.69 | 365 | Method 1 |
| 65 | 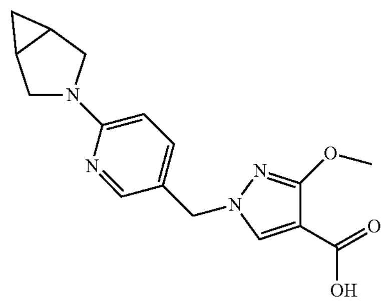 [SMILES: COc1nn(Cc2ccc(N3CC4CC4C3)nc2)cc1C(=O)O] | 0.66 | 315 | Method 1 |
| 66 | 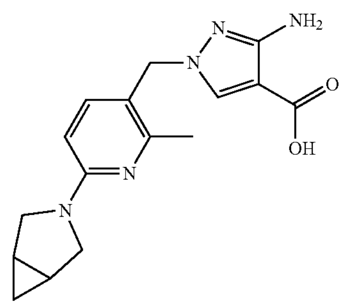 [SMILES: Cc1nc(N2CC3CC3C2)ccc1Cn1cc(C(=O)O)c(N)n1] | 0.59 | 314 | Method 2 |
| 67 | 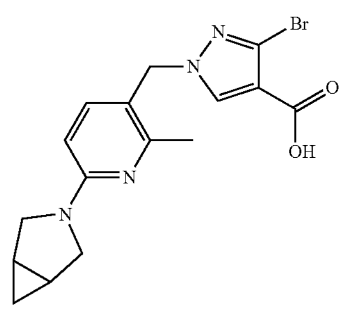 [SMILES: Cc1nc(N2CC3CC3C2)ccc1Cn1cc(C(=O)O)c(Br)n1] | 0.71 | 377 | Method 1 |
| 68 | 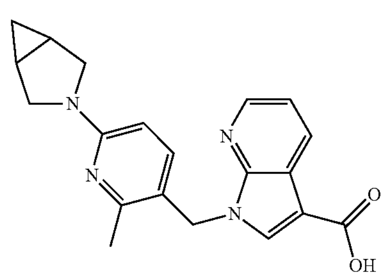 [SMILES: Cc1nc(N2CC3CC3C2)ccc1Cn1cc(C(=O)O)c2cccnc21] | 0.75 | 349 | Method 1 |

-continued

| Intermediate | Structure | $t_R$ | Mass spectrum (ESI+): m/z [M + H]+ | LC Method |
|---|---|---|---|---|
| 69 | (structure) | 0.94 | 399 | Method 1 |

| Intermediate | Name | Name of starting material |
|---|---|---|
| 42 | 7-[(6-{6,6-Difluoro-3-azabicyclo[3.1.0]hexan-3-yl}-2-methylpyridin-3-yl)methyl]-7H-pyrrolo[2,3-d]pyrimidine-5-carboxylic acid | Methyl 7-[(6-{6,6-difluoro-3-azabicyclo-[3.1.0]hexan-3-yl}-2-methylpyridin-3-yl)-methyl]-7H-pyrrolo[2,3-d]pyrimidine-5-carboxylate |
| 43 | 1-[(6-{3-Azabicyclo[3.1.0]hexan-3-yl}-2-methylpyridin-3-yl)methyl]-3-(difluoromethyl)-1H-pyrazole-4-carboxylic acid | Ethyl 1-[(6-{3-azabicyclo[3.1.0]hexan-3-yl}-2-methylpyridin-3-yl)methyl]-3-(difluoromethyl)-1H-pyrazole-4-carboxylate |
| 44 | 1-[(6-{6,6-Difluoro-3-azabicyclo[3.1.0]hexan-3-yl}-2-methylpyridin-3-yl)methyl]-3-(methoxymethyl)-1H-pyrazole-4-carboxylic acid | Methyl 1-[(6-{6,6-difluoro-3-azabicyclo-[3.1.0]hexan-3-yl}-2-methylpyridin-3-yl)-methyl]-3-(methoxymethyl)-1H-pyrazole-4-carboxylate |
| 45 | 1-[(6-{3-Azabicyclo[3.1.0]hexan-3-yl}-2-methylpyridin-3-yl)methyl]-3-(methoxymethyl)-1H-pyrazole-4-carboxylic acid | Methyl 1-[(6-{3-azabicyclo[3.1.0]hexan-3-yl}-2-methylpyridin-3-yl)methyl]-3-(methoxymethyl)-1H-pyrazole-4-carboxylate |
| 46 | 7-[(6-{3-Azabicyclo[3.1.0]hexan-3-yl}-2-methylpyridin-3-yl)methyl]-7H-pyrrolo[2,3-d]pyrimidine-5-carboxylic acid | Methyl 7-[(6-{3-azabicyclo[3.1.0]hexan-3-yl}-2-methylpyridin-3-yl)methyl]-7H-pyrrolo[2,3-d]pyrimidine-5-carboxylate |
| 47 | 1-[(6-{6,6-Difluoro-3-azabicyclo[3.1.0]hexan-3-yl}-2-methylpyridin-3-yl)methyl]-3-methyl-1H-pyrazole-4-carboxylic acid | Methyl 1-[(6-{6,6-difluoro-3-azabicyclo-[3.1.0]hexan-3-yl}-2-methylpyridin-3-yl)-methyl]-3-methyl-1H-pyrazole-4-carboxylate |
| 48 | 1-[(6-{3-Azabicyclo[3.1.0]hexan-3-yl}-2-methylpyridin-3-yl)methyl]-3-methyl-1H-pyrazole-4-carboxylic acid | Methyl 1-[(6-{3-azabicyclo[3.1.0]hexan-3-yl}-2-methylpyridin-3-yl)methyl]-3-methyl-1H-pyrazole-4-carboxylate |
| 49 | 1-[(6-{3-Azabicyclo[3.1.0]hexan-3-yl}-2-methylpyridin-3-yl)methyl]-3-methoxy-1H-pyrazole-4-carboxylic acid | Ethyl 1-[(6-{3-azabicyclo[3.1.0]hexan-3-yl}-2-methylpyridin-3-yl)methyl]-3-methoxy-1H-pyrazole-4-carboxylate |
| 50 | 7-[(2-{6,6-Difluoro-3-azabicyclo[3.1.0]hexan-3-yl}-4-methylpyrimidin-5-yl)methyl]-7H-pyrrolo[2,3-d]pyrimidine-5-carboxylic acid | Methyl 7-[(2-{6,6-difluoro-3-azabicyclo-[3.1.0]hexan-3-yl}-4-methylpyrimidin-5-yl)-methyl]-7H-pyrrolo[2,3-d]pyrimidine-5-carboxylate |
| 51 | 1-[(6-{5-Azaspiro[2.3]hexan-5-yl}-2-methylpyridin-3-yl)methyl]-3-(methoxymethyl)-1H-pyrazole-4-carboxylic acid | Methyl 1-[(6-{5-azaspiro[2.3] hexan-5-yl}-2-methylpyridin-3-yl)methyl]-3-(methoxymethyl)-1H-pyrazole-4-carboxylate |
| 52 | 7-[(2-{3-Azabicyclo[3.1.0]hexan-3-yl}-4-methylpyrimidin-5-yl)methyl]-7H-pyrrolo[2,3-d]pyrimidine-5-carboxylic acid | Methyl 7-[(2-{3-azabicyclo[3.1.0]hexan-3-yl}-4-methylpyrimidin-5-yl)methyl]-7H-pyrrolo[2,3-d]pyrimidine-5-carboxylate |
| 53 | 1-[(6-{5-Azaspiro[2.3]hexan-5-yl}-2-methylpyridin-3-yl)methyl]-3-methyl-1H-pyrazole-4-carboxylic acid | Methyl 1-[(6-{5-azaspiro[2.3] hexan-5-yl}-2-methylpyridin-3-yl)methyl]-3-methyl-1H-pyrazole-4-carboxylate |
| 54 | 1-[(2-{3-azabicyclo[3.1.0]hexan-3-yl}-4-methylpyrimidin-5-yl)methyl]-3-methyl-1H-pyrazole-4-carboxylic acid | Methyl 1-[(2-{3-azabicyclo[3.1.0]hexan-3-yl}-4-methylpyrimidin-5-yl)methyl]-3-methyl-1H-pyrazole-4-carboxylate |
| 55 | 1-[(2-{6,6-Difluoro-3-azabicyclo[3.1.0]hexan-3-yl}-4-methylpyrimidin-5-yl)methyl]-3-(methoxymethyl)-1H-pyrazole-4-carboxylic acid | Methyl 1-[(2-{6,6-difluoro-3-azabicyclo-[3.1.0]hexan-3-yl}-4-methylpyrimidin-5-yl)-methyl]-3-(methoxymethyl)-1H-pyrazole-4-carboxylate |
| 56 | 1-[(2-{6,6-Difluoro-3-azabicyclo[3.1.0]hexan-3-yl}-4-methylpyrimidin-5-yl)methyl]-3-methyl-1H-pyrazole-4-carboxylic acid | Methyl 1-[(2-{6,6-difluoro-3-azabicyclo-[3.1.0]hexan-3-yl}-4-methylpyrimidin-5-yl)-methyl]-3-methyl-1H-pyrazole-4-carboxylate |
| 57 | 1-[(2-{3-Azabicyclo[3.1.0]hexan-3-yl}-4-methylpyrimidin-5-yl)methyl]-3-(methoxymethyl)-1H-pyrazole-4-carboxylic acid | Methyl 1-[(2-{3-azabicyclo[3.1.0]hexan-3-yl}-4-methylpyrimidin-5-yl)methyl]-3-(methoxymethyl)-1H-pyrazole-4-carboxylate |
| 58 | 1-[(2-{5-Azaspiro[2.3]hexan-5-yl}-4-methyl-pyrimidin-5-yl)methyl]-3-methyl-1H-pyrazole-4-carboxylic acid | Methyl 1-[(2-{5-azaspiro[2.3] hexan-5-yl}-4-methylpyrimidin-5-yl)methyl]-3-methyl-1H-pyrazole-4-carboxylate |
| 59 | 1-[(2-{5-Azaspiro[2.3]hexan-5-yl}-4-methyl-pyrimidin-5-yl)methyl]-1H-pyrazole-4-carboxylic acid | Ethyl 1-[(2-{5-azaspiro[2.3] hexan-5-yl}-4-methylpyrimidin-5-yl)methyl]-1H-pyrazole-4-carboxylate |

-continued

| Intermediate | Name | Name of starting material |
|---|---|---|
| 60 | 1-[(2-{5-Azaspiro[2.3]hexan-5-yl}-4-methylpyrimidin-5-yl)methyl]-3-(methoxymethyl)-1H-pyrazole-4-carboxylic acid | Methyl 1-[(2-{5-azaspiro[2.3] hexan-5-yl}-4-methylpyrimidin-5-yl)methyl]-3-(methoxymethyl)-1H-pyrazole-4-carboxylate |
| 61 | 1-[(6-{3-Azabicyclo[3.1.0]hexan-3-yl}pyridin-3-yl)methyl]-3-(1-methyl-1H-pyrazol-4-yl)-1H-pyrazole-4-carboxylic acid | Methyl 1-[(6-{3-azabicyclo[3.1.0]hexan-3-yl}-2-methylpyridin-3-yl)methyl]-3-(1-methyl-1H-pyrazol-4-yl)-1H-pyrazole-4-carboxylate |
| 62 | 1-[(6-{3-azabicyclo[3.1.0]hexan-3-yl}pyridin-3-yl)methyl]-3-(difluoromethyl)-1H-pyrazole-4-carboxylic acid | Ethyl 1-[(6-{3-azabicyclo[3.1.0]hexan-3-yl}pyridin-3-yl)methyl]-3-(difluoromethyl)-1H-pyrazole-4-carboxylate |
| 63 | 1-[(6-{3-azabicyclo[3.1.0]hexan-3-yl}pyridin-3-yl)methyl]-1H-pyrrolo[2,3-b]pyridine-3-carboxylic acid | Methyl 1-[(6-{3-azabicyclo[3.1.0]hexan-3-yl}pyridin-3-yl)methyl]-1H-pyrrolo[2,3-b]pyridine-3-carboxylate |
| 64 | 1-[(6-{3-azabicyclo[3.1.0]hexan-3-yl}pyridin-3-yl)methyl]-3-(1-methyl-1H-pyrazol-4-yl)-1H-pyrazole-4-carboxylic acid | methyl 1-[(6-{3-azabicyclo[3.1.0]hexan-3-yl}pyridin-3-yl)methyl]-3-(1-methyl-1H-pyrazol-4-yl)-1H-pyrazole-4-carboxylate |
| 65 | 1-[(6-{3-azabicyclo[3.1.0]hexan-3-yl}pyridin-3-yl)methyl]-3-methoxy-1H-pyrazole-4-carboxylic acid | Ethyl 1-[(6-{3-azabicyclo[3.1.0]hexan-3-yl}pyridin-3-yl)methyl]-3-methoxy-1H-pyrazole-4-carboxylate |
| 66 | 3-amino-1-[(6-{3-azabicyclo[3.1.0]hexan-3-yl}-2-methylpyridin-3-yl)methyl]-1H-pyrazole-4-carboxylic acid | Benzyl 3-amino-1-[(6-{3-azabicyclo[3.1.0]-hexan-3-yl}-2-methylpyridin-3-yl)methyl]-1H-pyrazole-4-carboxylate |
| 67 | 1-[(6-{3-azabicyclo[3.1.0]hexan-3-yl}-2-methylpyridin-3-yl)methyl]-3-bromo-1H-pyrazole-4-carboxylic acid | Ethyl 1-[(6-{3-azabicyclo[3.1.0]hexan-3-yl}-2-methylpyridin-3-yl)methyl]-3-bromo-1H-pyrazole-4-carboxylate |
| 68 | 1-[(6-{3-azabicyclo[3.1.0]hexan-3-yl}-2-methylpyridin-3-yl)methyl]-1H-pyrrolo[2,3-b]pyridine-3-carboxylic acid | Methyl 1-[(6-{3-azabicyclo[3.1.0]hexan-3-yl}-2-methylpyridin-3-yl)methyl]-1H-pyrrolo[2,3-b]pyridine-3-carboxylate |
| 69 | 1-[(5-bromo-6-{6,6-difluoro-3-azabicyclo-[3.1.0]hexan-3-yl}pyridin-3-yl)methyl]-1H-pyrazole-4-carboxylic acid | Ethyl 1-[(5-bromo-6-{6,6-difluoro-3-azabicyclo[3.1.0]hexan-3-yl}pyridin-3-yl)methyl]-1H-pyrazole-4-carboxylate |

Intermediate 70

3-Amino-1-[(6-{3-azabicyclo[3.1.0]hexan-3-yl}pyridin-3-yl)methyl]-1H-pyrazole-4-carboxylic acid

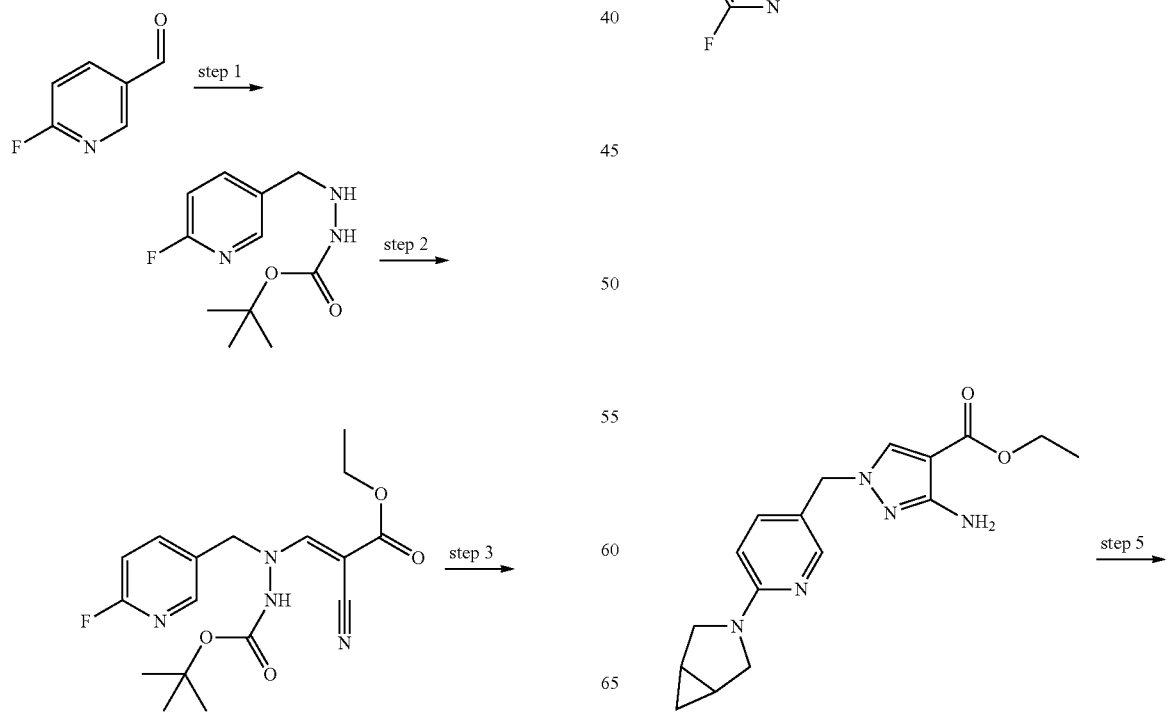

-continued

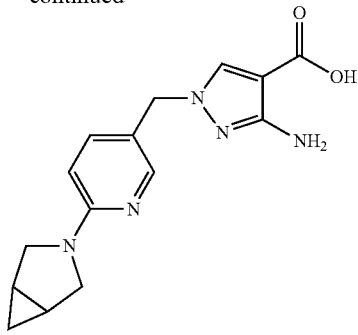

Step 1: N'-[(6-fluoropyridin-3-yl)methyl](tert-butoxy)carbohydrazide 6-fluoropyridine-3-carbaldehyde (1.1 g) is dissolved in THF (10 mL), (tert-butoxy)carbohydrazide (1.28 g) and acetic acid (1 mL) is added and stirred for 5 min at rt. Sodiumcyanoborohydride (0.83 g) is added and stirred for 3 h at rt and 16 h at 40° C. The mixture is filtered, DCM is added, washed with water and concentrated in vacuo. The residue is chromatographed on silica gel (cyclohexane/EtOAc) to give the title compound.

LC (Method 2): $t_R$=0.82 min; Mass spectrum (ESI⁺): m/z=242 [M+H]⁺.

Step 2: Ethyl (2E)-3-({[(tert-butoxy)carbonyl]amino}[(6-fluoropyridin-3-yl)methyl]amino)-2-cyanoprop-2-enoate N'-[(6-fluoropyridin-3-yl)methyl](tert-butoxy)carbohydrazide (650 mg) and ethyl (2E)-2-cyano-3-ethoxyprop-2-enoate (478 mg) are dissolved in dioxane and stirred for 16 h at 80° C. and for 24 h at 90° C. The mixture is purified by HPLC on reversed phase (ACN, water) to give the title compound.

LC (Method 2): $t_R$=0.91 min; Mass spectrum (ESI⁺): m/z=365 [M+H]⁺.

Step 3: Ethyl 3-amino-1-[(6-fluoropyridin-3-yl)methyl]-1H-pyrazole-4-carboxylate Ethyl(2E)-3-({[(tert-butoxy)carbonyl]amino}[(6-fluoropyridin-3-yl)methyl]amino)-2-cyanoprop-2-enoate (469 mg) is dissolved in DMSO and stirred at 80° C. for 3 d. The mixture is purified by HPLC on reversed phase (ACN, water) to give the title compound.

LC (Method 2): $t_R$=0.78 min; Mass spectrum (ESI⁺): m/z=265 [M+H]⁺.

Step 4: Ethyl 3-amino-1-[(6-{3-azabicyclo[3.1.0]hexan-3-yl}pyridin-3-yl)methyl]-1H-pyrazole-4-carboxylate Ethyl 3-amino-1-[(6-fluoropyridin-3-yl)methyl]-1H-pyrazole-4-carboxylate (53 mg) is dissolved in DMSO (1 mL), 3-azabicyclo[3.1.0]hexane hydrochloride (60 mg) and N,N-Diisopropylethylamine (0.15 mL) are added and the mixture is stirred for 2 d at 90° C. The mixture is purified by HPLC on reversed phase (ACN, water) to give the title compound.

LC (Method 2): $t_R$=0.93 min; Mass spectrum (ESI⁺): m/z=328 [M+H]⁺.

Step 5: 3-Amino-1-[(6-{3-azabicyclo[3.1.0]hexan-3-yl}pyridin-3-yl)methyl]-1H-pyrazole-4-carboxylic acid Ethyl 3-amino-1-[(6-{3-azabicyclo[3.1.0]hexan-3-yl}pyridin-3-yl)methyl]-1H-pyrazole-4-carboxylate (70 mg) is dissolved in 1 M NaOH in water (1 mL) and EtOH (4 mL) and stirred at 60° C. for 3 h. After cooling to rt 1 M aqueous HCl (1 mL) is added and the solvents are evaporated in vacuo to give the title compound (containing NaCl).

LC (Method 3): $t_R$=0.56 min; Mass spectrum (ESI⁺): m/z=300 [M+H]⁺.

Intermediate 71

1-[(6-{5-Azaspiro[2.3]hexan-5-yl}-2-methylpyridin-3-yl)methyl]-1H-pyrazole-4-carboxylic acid

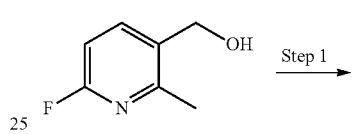

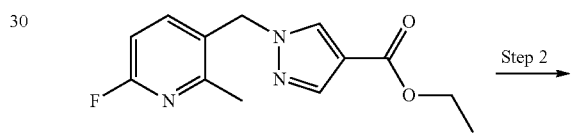

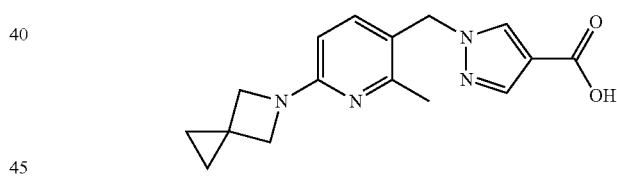

Step 1: Ethyl 1-[(6-fluoro-2-methylpyridin-3-yl)methyl]-1H-pyrazole-4-carboxylate (6-Fluoro-2-methylpyridin-3-yl)methanol (4.12 g) is dissolved in THF (50 mL) and cooled to −10° C. Ethyl 1H-pyrazole-4-carboxylate (4.43 g) and tributyl phosphine (9 mL) are added. Di-tert.-butyl-azodicarboxylate (7.4 g) is slowly added portionwise and the mixture is stirred at rt for 45 min and concentrated in vacuo. The residue is chromatographed on silica gel (cyclohexane/EtOAc) to give the title compound.

LC (Method 2): $t_R$=0.88 min; Mass spectrum (ESI⁺): m/z=264 [M+H]⁺.

Step 2: 1-[(6-{5-azaspiro[2.3]hexan-5-yl}-2-methylpyridin-3-yl)methyl]-1H-pyrazole-4-carboxylic acid Ethyl 1-[(6-fluoro-2-methylpyridin-3-yl)methyl]-1H-pyrazole-4-carboxylate (0.5 g) is dissolved in DMSO (2 mL), 5-azaspiro[2.3]hexane trifluoroacetate (1.2 g) and N,N-Diisopropylethylamine (2 mL) are added and the mixture is stirred for 16 h at 100° C. and additional 5 h at 120° C. After cooling to rt, the N,N-diisopropylethylamine phase is removed, 4 M NaOH (4 mL) is added and stirred at 60° C. for 2 h. 4 M aqueous HCl (4 mL) is added and the mixture is purified by HPLC on reversed phase (ACN, water) to give the title compound.

LC (Method 1): $t_R$=0.68 min; Mass spectrum (ESI$^+$): m/z=299 [M+H]$^+$.

Intermediate 72

1-[(6-{1,1-difluoro-5-azaspiro[2.3]hexan-5-yl}-2-methylpyridin-3-yl)methyl]-1H-pyrazole-4-carboxylic acid

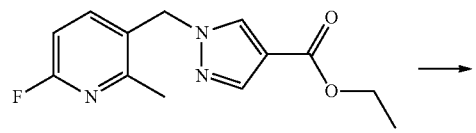 →

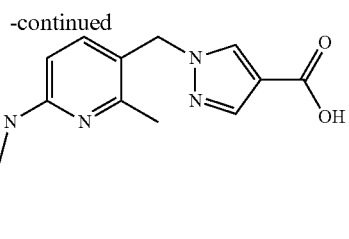

Ethyl 1-[(6-fluoro-2-methylpyridin-3-yl)methyl]-1H-pyrazole-4-carboxylate (263 mg) is dissolved in DMSO (2 mL), 1,1-difluoro-5-azaspiro[2.3]hexane hydrochloride (180 mg) and N,N-diisopropylethylamine (0.6 mL) are added and the mixture is stirred for 16 h at 100° C. and additional 5 h at 120° C. After cooling to rt, 4 M NaOH (1.5 mL) is added and stirred at 60° C. for 2 h. 4 M aqueous HCl (1.5 mL) is added and the mixture is purified by HPLC on reversed phase (ACN, water) to give the title compound.

LC (Method 1): $t_R$=0.69 min; Mass spectrum (ESI$^+$): m/z=335 [M+H]$^+$.

Intermediates 73-75 were prepared in analogy to Intermediate 72:

| Intermediate | Structure | $t_R$ | m/z [M + H]$^+$ | LC Method |
|---|---|---|---|---|
| 73 | 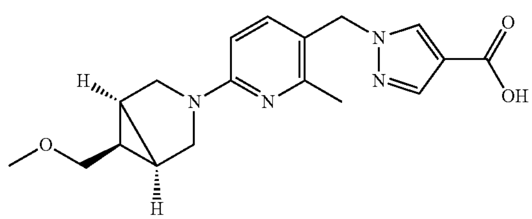 [SMILES: COC[C@H]1[C@H]2CN(c3ccc(Cn4cc(C(=O)O)cn4)c(C)n3)C[C@@H]12] | 0.615 | 343 | Method 4 |
| 74 | 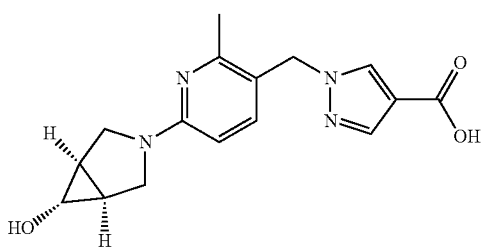 [SMILES: Cc1nc(N2C[C@@H]3[C@@H](O)[C@@H]3C2)ccc1Cn1cc(C(=O)O)cn1] | 0.58 | 315 | Method 1 |
| 75 | 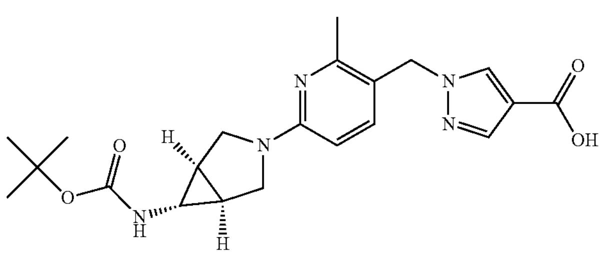 [SMILES: Cc1nc(N2C[C@@H]3[C@H](C2)[C@H]3NC(=O)OC(C)(C)C)ccc1Cn1cc(C(=O)O)cn1] | 0.76 | 414 | Method 1 |

| Intermediate | Name | Name of starting material 1 | Name of starting material 2 |
|---|---|---|---|
| 73 | 1-({6-[(1R,5S,6R)-6-(methoxy-methyl)-3-azabicyclo[3.1.0]hexan-3-yl]-2-methylpyridin-3-yl}methyl)-1H-pyrazole-4-carboxylic acid | Ethyl 1-[(6-fluoro-2-methylpyridin-3-yl)-methyl]-1H-pyrazole-4-carboxylate | (1R,5S,6R)-6-(methoxy-methyl)-3-azabicyclo-[3.1.0]hexane |

-continued

| Intermediate | Name | Name of starting material 1 | Name of starting material 2 |
| --- | --- | --- | --- |
| 74 | 1-({6-[(1R,5S,6R)-6-hydroxy-3-azabicyclo[3.1.0]hexan-3-yl]-2-methylpyridin-3-yl}methyl)-1H-pyrazole-4-carboxylic acid | Ethyl 1-[(6-fluoro-2-methylpyridin-3-yl)methyl]-1H-pyrazole-4-carboxylate | (1R,5S,6R)-3-azabicyclo-[3.1.0]hexan-6-ol hydrochloride |
| 75 | 1-({6-[(1R,5S,6R)-6-{[(tert-butoxy)-carbonyl]amino}-3-azabicyclo[3.1.0]-hexan-3-yl]-2-methylpyridin-3-yl}-methyl)-1H-pyrazole-4-carboxylic acid | Ethyl 1-[(6-fluoro-2-methylpyridin-3-yl)methyl]-1H-pyrazole-4-carboxylate | tert-butyl N-[(1R,5S,6R)-3-azabicyclo[3.1.0]hexan-6-yl]carbamate |

Intermediate 76

7-[(2-{5-Azaspiro[2.3]hexan-5-yl}-4-methylpyrimidin-5-yl)methyl]-7H-pyrrolo[2,3-d]pyrimidine-5-carboxylic acid

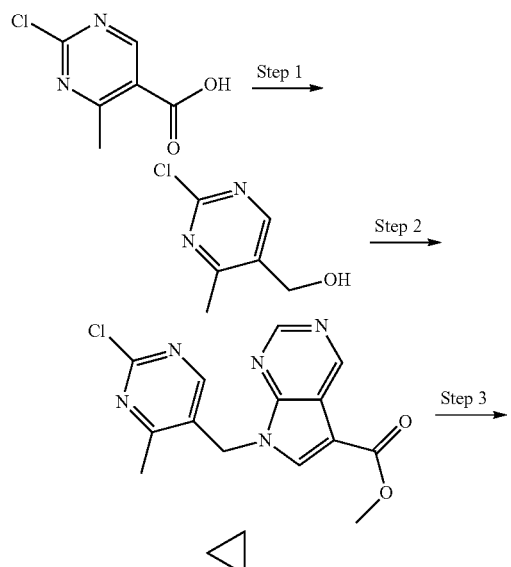

Step 1: (2-chloro-4-methylpyrimidin-5-yl)methanol

2-Chloro-4-methylpyrimidine-5-carboxylic acid (7 g) is dissolved in dimethoxyethane (200 mL) and N-methylmorpholine (4.2 mL) is added. The mixture is cooled to 0° C., isobutylchloroformate (5.1 mL) is added and the mixture is stirred for 30 min at 0° C. Then the mixture is filtered through celite, cooled to 0° C., a solution of NaBH$_4$ (1.6 g) in water (20 mL) is added and stirred for 15 min. Water is added and the mixture is extracted with EtOAc. The organic phase is washed with brine, dried (MgSO$_4$) and concentrated in vacuo. The residue is chromatographed on silica gel (DCM/MeOH 97:3→50:50) to give the title compound.

LC (Method 1): $t_R$=0.50 min; Mass spectrum (ESI$^+$): m/z=159/161 (Cl) [M+H]$^+$.

Step 2: Methyl 7-[(2-chloro-4-methylpyrimidin-5-yl)methyl]-7H-pyrrolo[2,3-d]pyrimidine-5-carboxylate (2-Chloro-4-methylpyrimidin-5-yl)methanol (475 mg) is dissolved in THF (10 mL) and DMSO (2 mL), cooled to −10° C. Methyl 7H-pyrrolo[2,3-d]pyrimidine-5-carboxylate (530 mg), tributyl phosphine (890 µL) are added. Di-tert.-butyl-azodicarblylate (750 mg) is slowly added portionwise and the mixture is stirred at rt for about 30 min. The mixture is purified by HPLC on reversed phase (ACN, water) to give the title compound.

LC (Method 1): $t_R$=0.80 min; Mass spectrum (ESI$^+$): m/z=318/320 (Cl) [M+H]$^+$.

Step 3: 7-[(2-{5-azaspiro[2.3]hexan-5-yl}-4-methylpyrimidin-5-yl)methyl]-7H-pyrrolo[2,3-d]pyrimidine-5-carboxylic acid Methyl 7-[(2-chloro-4-methylpyrimidin-5-yl)methyl]-7H-pyrrolo[2,3-d]pyrimidine-5-carboxylate (200 mg) is dissolved in DMSO (2 mL), 5-azaspiro[2.3]hexane trifluoroacetate (250 mg) and N,N-diisopropylethylamine (0.35 mL) are added and the mixture is stirred for 6 h at 80° C. After cooling to rt, 4 M NaOH (1 mL) is added and stirred at 60° C. for 2 h. 4 M aqueous HCl (1 mL) is added and the mixture is purified by HPLC on reversed phase (ACN, water) to give the title compound.

LC (Method 1): $t_R$=0.72 min; Mass spectrum (ESI$^+$): m/z=351 [M+H]$^+$.

Intermediate 77

N-{[5-chloro-2-(1H-1,2,3,4-tetrazol-1-yl)phenyl]methyl}-1-[(6-fluoro-2-methylpyridin-3-yl)methyl]-1H-pyrazole-4-carboxamide

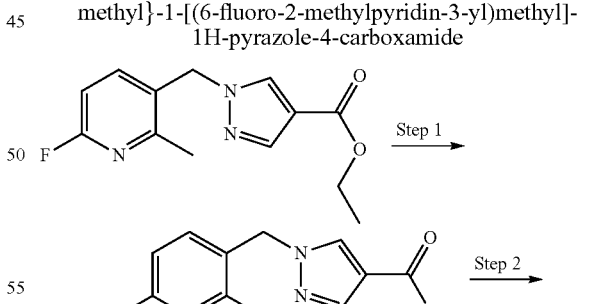

Step 1: 1-[(6-fluoro-2-methylpyridin-3-yl)methyl]-1H-pyrazole-4-carboxylic acid Ethyl 1-[(6-fluoro-2-methylpyridin-3-yl)methyl]-1H-pyrazole-4-carboxylate (9.1 g) is dissolved in THF (150 mL), a solution of LiOH (1.7 g) in water (15 mL) is added and the mixture is stirred for 3 d at 60° C. Acetic acid (3.8 mL) is added and the mixture is concentrated in vacuo. Water is added and the mixture is extracted with DCM/isopropanol 9:1. The organic phase is washed with brine, dried (MgSO$_4$) and concentrated in vacuo to give the title compound.

LC (Method 1): $t_R$=0.72 min; Mass spectrum (ESI$^+$): m/z=236 [M+H]$^+$.

Step 2: N-{[5-chloro-2-(1H-1,2,3,4-tetrazol-1-yl)phenyl]methyl}-1-[(6-fluoro-2-methylpyridin-3-yl)methyl]-1H-pyrazole-4-carboxamide To a solution of 1-[(6-fluoro-2-methylpyridin-3-yl)methyl]-1H-pyrazole-4-carboxylic acid (1.68 g) in DMF (10 mL) is added N,N-diisopropylethylamine (3 mL), O-(7-azabenzotriazol-1-yl)-N,N,N',N'-tetramethyluronium-hexafluoro-phosphat (HATU, 2.85 g) and the mixture is stirred for 5 min. [5-chloro-2-(1H-1,2,3,4-tetrazol-1-yl)phenyl]-methanamine hydrochloride (1.8 g) is added and the mixture is stirred for 1 h. The mixture is purified by HPLC on reversed phase (ACN, water) to give the title compound.

LC (Method 1): $t_R$=0.93 min; Mass spectrum (ESI$^+$): m/z=427/429 (Cl) [M+H]$^+$.

SYNTHESIS OF EXAMPLES

Example 1

1-[(6-{3-azabicyclo[3.1.0]hexan-3-yl}-2-methylpyridin-3-yl)methyl]-N-{[5-chloro-2-(1H-1,2,3,4-tetrazol-1-yl)phenyl]-methyl}-1H-pyrazole-4-carboxamide

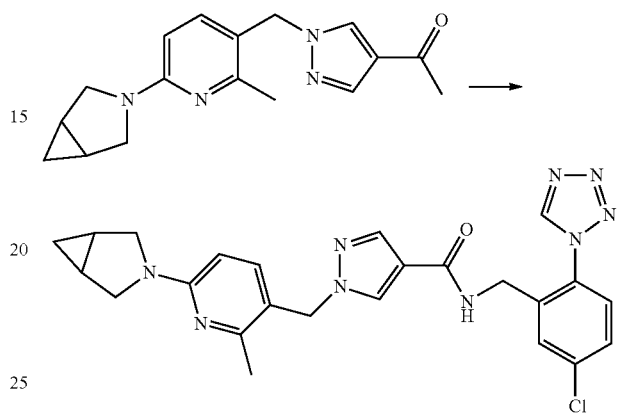

A solution of 1-[(6-{3-azabicyclo[3.1.0]hexan-3-yl}-2-methylpyridin-3-yl)methyl]-1H-pyrazole-4-carboxylic acid (30 mg) in DMF (2 mL) is added N,N-diisopropylethylamine (50 µL) and O-(7-azabenzotriazol-1-yl)-N,N,N',N'-tetramethyluronium-hexafluorophosphat (HATU, 40 mg) is stirred for 5 min. [5-chloro-2-(1H-1,2,3,4-tetrazol-1-yl)-phenyl]methanamine hydrochloride (21 mg) is added and the mixture is stirred for 16 h. The mixture is purified by HPLC on reversed phase (ACN, water) to give the title compound.

LC (Method 1): $t_R$=0.76 min; Mass spectrum (ESI$^+$): m/z=490 [M+H]$^+$.

Examples 2-57 are prepared in analogy to example 1:

| Example | Structure | $t_R$ | Mass spectrum (ESI+): m/z [M + H]+ | LC Method |
|---|---|---|---|---|
| 2 | 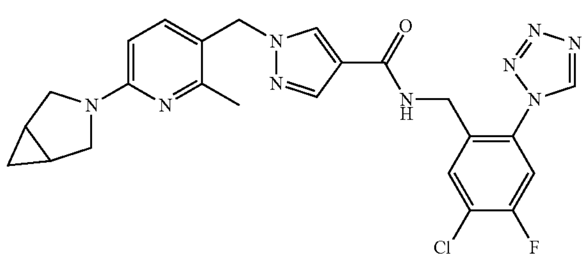 [SMILES: Cc1nc(N2CC3CC3C2)ccc1Cn1cc(C(=O)NCc2cc(Cl)c(F)cc2-n2cnnn2)cn1] | 1.03 | 508 | Method 2 |
| 3 | 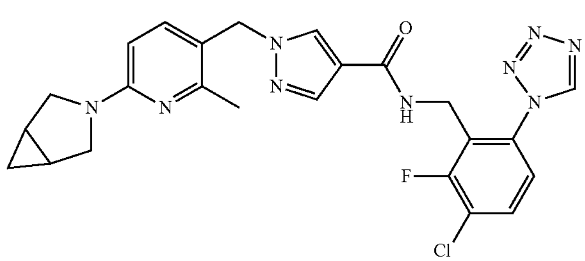 [SMILES: Cc1nc(N2CC3CC3C2)ccc1Cn1cc(C(=O)NCc2c(-n3cnnn3)ccc(Cl)c2F)cn1] | 1.02 | 508 | Method 2 |

| Example | Structure | $t_R$ | Mass spectrum (ESI+): m/z [M + H]+ | LC Method |
|---|---|---|---|---|
| 4 | 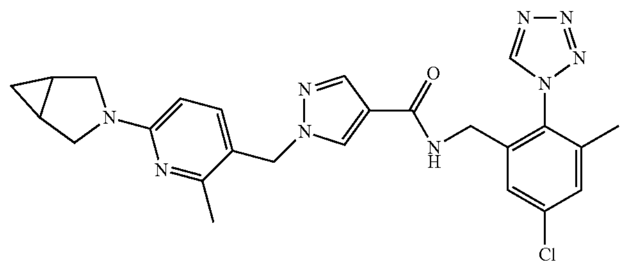 [SMILES: Cc1cc(Cl)cc(CNC(=O)c2cnn(Cc3ccc(N4CC5CC5C4)nc3C)c2)c1-n1cnnn1] | 0.84 | 504 | Method 6 |
| 5 | 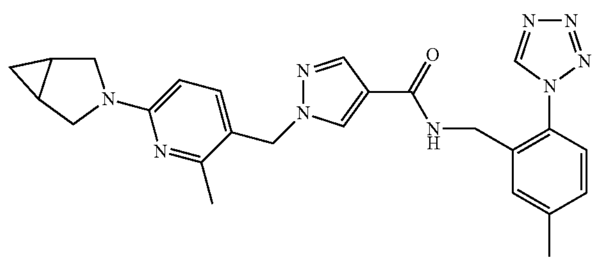 [SMILES: Cc1ccc(-n2cnnn2)c(CNC(=O)c2cnn(Cc3ccc(N4CC5CC5C4)nc3C)c2)c1] | 0.77 | 470 | Method 6 |
| 6 | 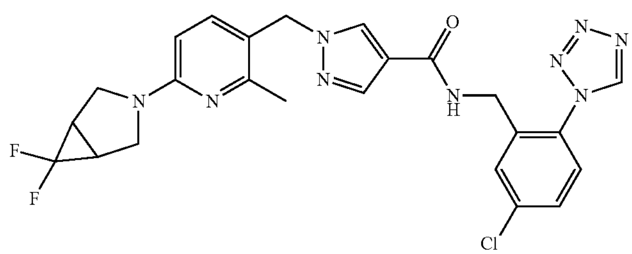 [SMILES: Cc1nc(N2CC3C(C2)C3(F)F)ccc1Cn1cc(C(=O)NCc2cc(Cl)ccc2-n2cnnn2)cn1] | 0.98 | 526 | Method 2 |
| 7 | 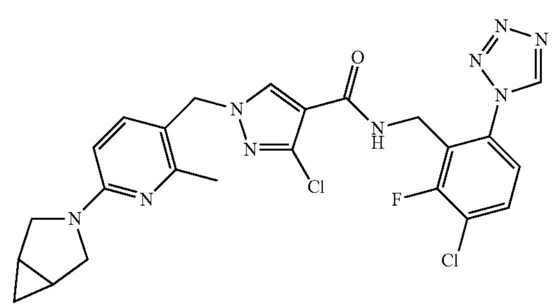 [SMILES: Cc1nc(N2CC3CC3C2)ccc1Cn1cc(C(=O)NCc2c(-n3cnnn3)ccc(Cl)c2F)c(Cl)n1] | 0.92 | 542 | Method 6 |
| 8 | 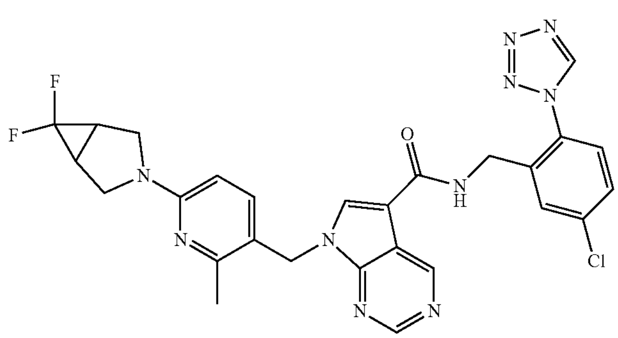 [SMILES: Cc1nc(N2CC3C(C2)C3(F)F)ccc1Cn1cc(C(=O)NCc2cc(Cl)ccc2-n2cnnn2)c2cncnc21] | 0.81 | 577 | Method 6 |

-continued

| Example | Structure | $t_R$ | Mass spectrum (ESI+): m/z [M + H]+ | LC Method |
|---|---|---|---|---|
| 9 | 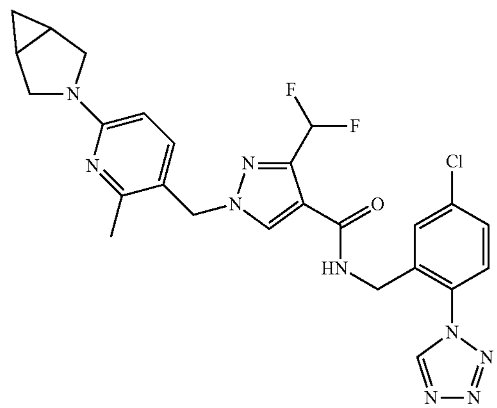 [SMILES: Cc1nc(N2CC3CC3C2)ccc1Cn1cc(C(=O)NCc2cc(Cl)ccc2-n2cnnn2)c(C(F)F)n1] | 0.91 | 540 | Method 7 |
| 10 | 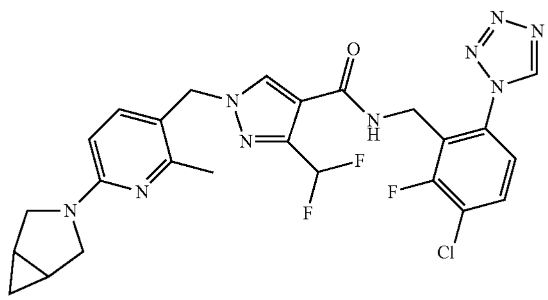 [SMILES: Cc1nc(N2CC3CC3C2)ccc1Cn1cc(C(=O)NCc2c(-n3cnnn3)ccc(Cl)c2F)c(C(F)F)n1] | 0.91 | 558 | Method 6 |
| 11 | 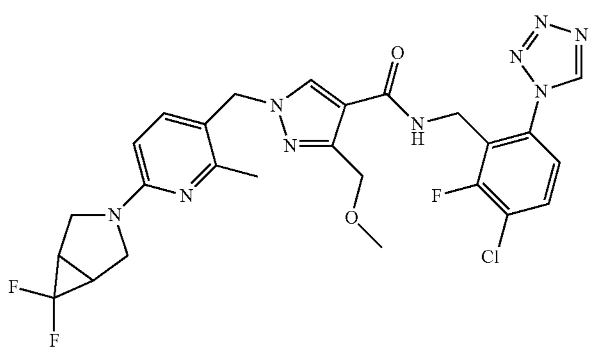 [SMILES: COCc1nn(Cc2ccc(N3CC4C(C3)C4(F)F)nc2C)cc1C(=O)NCc1c(-n2cnnn2)ccc(Cl)c1F] | 0.87 | 588 | Method 6 |
| 12 | 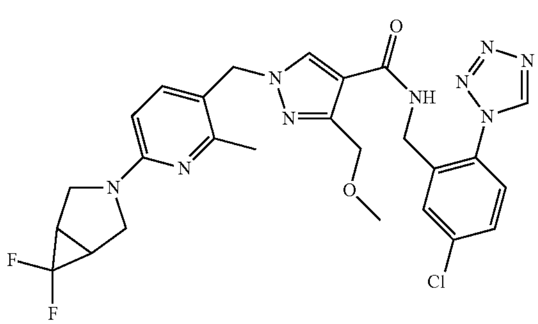 [SMILES: COCc1nn(Cc2ccc(N3CC4C(C3)C4(F)F)nc2C)cc1C(=O)NCc1cc(Cl)ccc1-n1cnnn1] | 0.84 | 570 | Method 6 |

-continued
| Example | Structure | $t_R$ | Mass spectrum (ESI+): m/z [M + H]+ | LC Method |
|---|---|---|---|---|
| 13 | 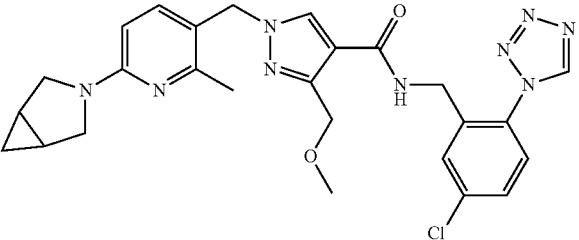 [SMILES: COCc1nn(Cc2ccc(N3CC4CC4C3)nc2C)cc1C(=O)NCc1cc(Cl)ccc1-n1cnnn1] | 4.62 | 534 | Method 9 |
| 14 | 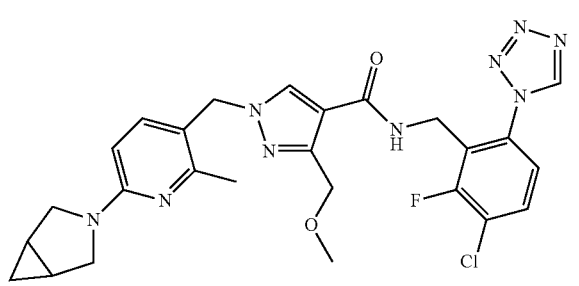 [SMILES: COCc1nn(Cc2ccc(N3CC4CC4C3)nc2C)cc1C(=O)NCc1c(-n2cnnn2)ccc(Cl)c1F] | 0.90 | 552 | Method 6 |
| 15 | 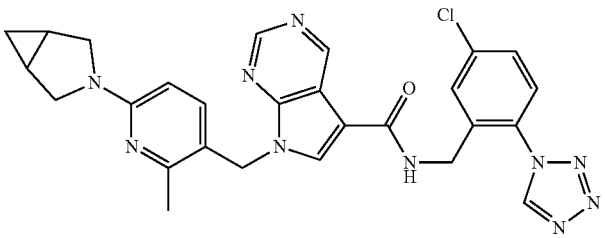 [SMILES: Cc1nc(N2CC3CC3C2)ccc1Cn1cc(C(=O)NCc2cc(Cl)ccc2-n2cnnn2)c2cncnc21] | 0.83 | 541 | Method 6 |
| 16 | 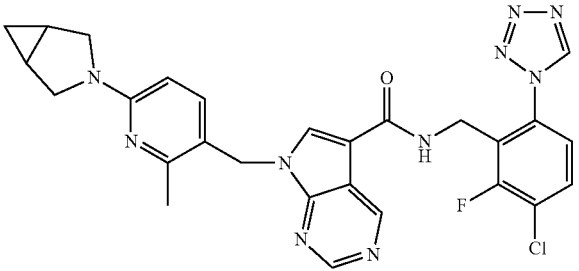 [SMILES: Cc1nc(N2CC3CC3C2)ccc1Cn1cc(C(=O)NCc2c(-n3cnnn3)ccc(Cl)c2F)c2cncnc21] | 0.85 | 559 | Method 6 |
| 17 | 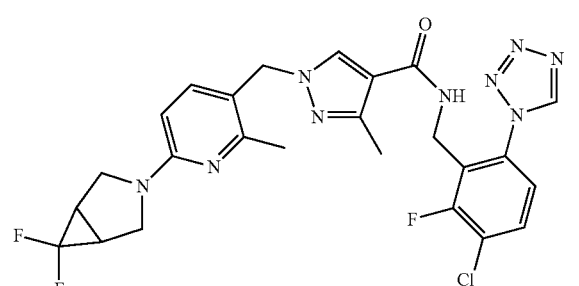 | 0.82 | 558 | Method 6 |

-continued
| Example | Structure | $t_R$ | Mass spectrum (ESI+): m/z [M + H]+ | LC Method |
|---|---|---|---|---|
| 18 | 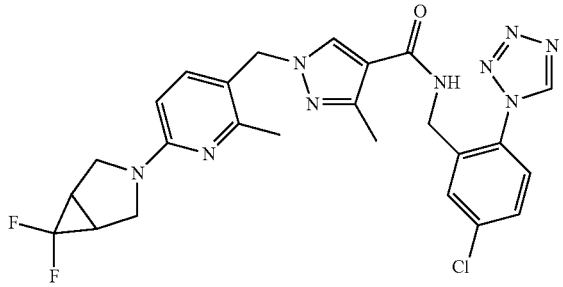 | 0.82 | 540 | Method 6 |
| 19 | 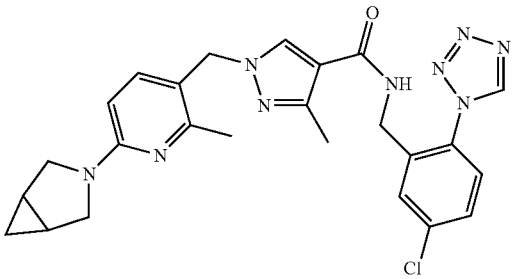 | 0.86 | 504 | Method 6 |
| 20 | 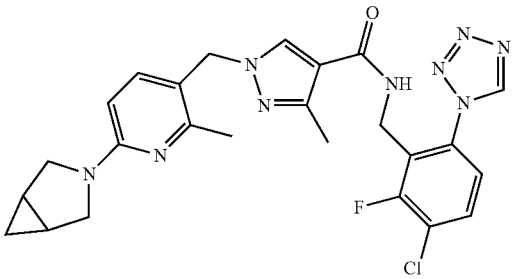 [SMILES: Cc1nc(N2CC3CC3C2)ccc1Cn1cc(C(=O)NCc2c(-n3cnnn3)ccc(Cl)c2F)c(C)n1] | 0.86 | 522 | Method 6 |
| 21 | 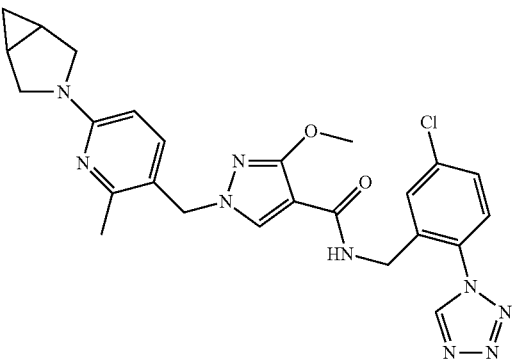 [SMILES: COc1nn(Cc2ccc(N3CC4CC4C3)nc2C)cc1C(=O)NCc1cc(Cl)ccc1-n1cnnn1] | 0.91 | 520 | Method 7 |
| 22 | 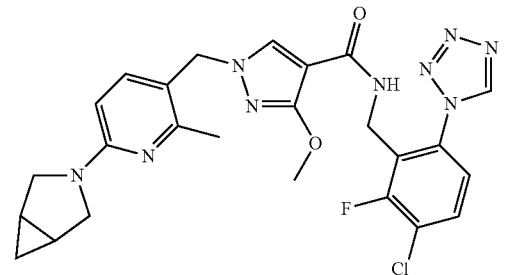 [SMILES: COc1nn(Cc2ccc(N3CC4CC4C3)nc2C)cc1C(=O)NCc1c(-n2cnnn2)ccc(Cl)c1F] | 0.92 | 538 | Method 6 |

-continued
| Example | Structure | $t_R$ | Mass spectrum (ESI+): m/z [M + H]+ | LC Method |
|---|---|---|---|---|
| 23 | 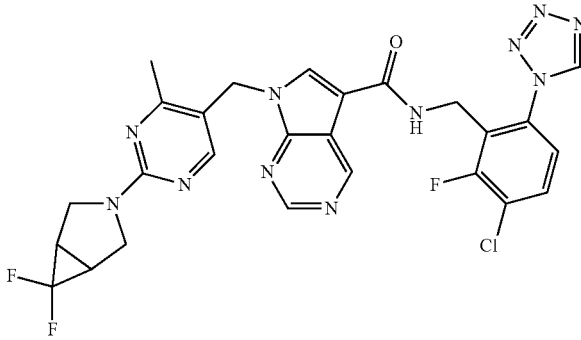 [SMILES: Cc1nc(N2CC3C(C2)C3(F)F)ncc1Cn1cc(C(=O)NCc2c(-n3cnnn3)ccc(Cl)c2F)c2cncnc21] | 0.76 | 596 | Method 6 |
| 24 | 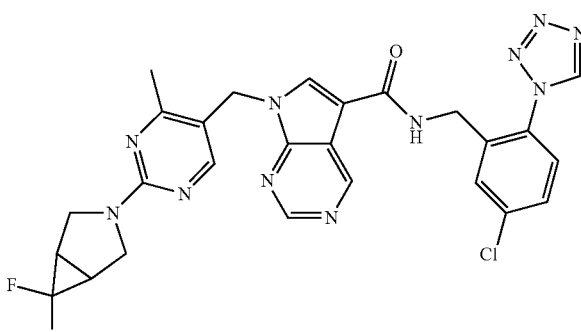 | 0.75 | 578 | Method 6 |
| 25 | 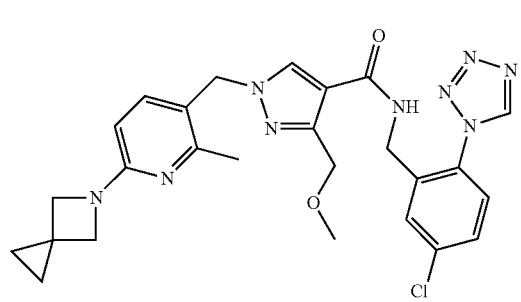 [SMILES: COCc1nn(Cc2ccc(N3CC4(CC4)C3)nc2C)cc1C(=O)NCc1cc(Cl)ccc1-n1cnnn1] | 0.82 | 534 | Method 6 |
| 26 | 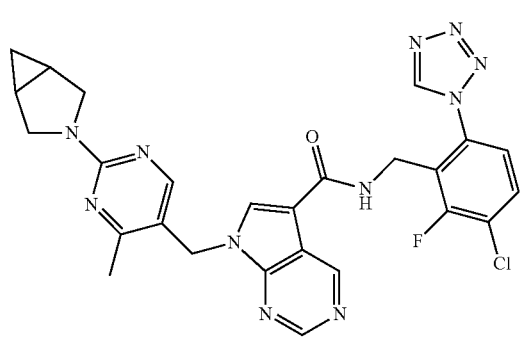 [SMILES: Cc1nc(N2CC3CC3C2)ncc1Cn1cc(C(=O)NCc2c(-n3cnnn3)ccc(Cl)c2F)c2cncnc21] | 0.77 | 560 | Method 6 |

-continued
| Example | Structure | $t_R$ | Mass spectrum (ESI+): m/z [M + H]+ | LC Method |
|---|---|---|---|---|
| 27 | 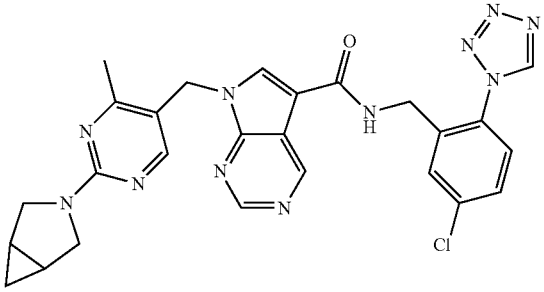 [SMILES: Cc1nc(N2CC3CC3C2)ncc1Cn1cc(C(=O)NCc2cc(Cl)ccc2-n2cnnn2)c2cncnc21] | 0.76 | 542 | Method 6 |
| 28 | 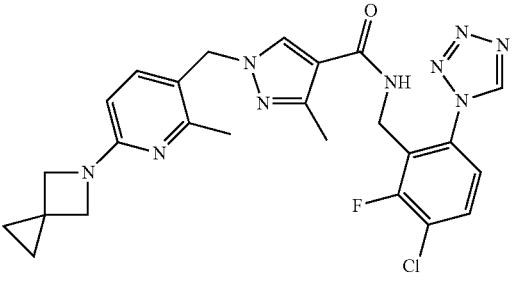 [SMILES: Cc1nc(N2CC3(CC3)C2)ccc1Cn1cc(C(=O)NCc2c(-n3cnnn3)ccc(Cl)c2F)c(C)n1] | 0.80 | 522 | Method 6 |
| 29 | 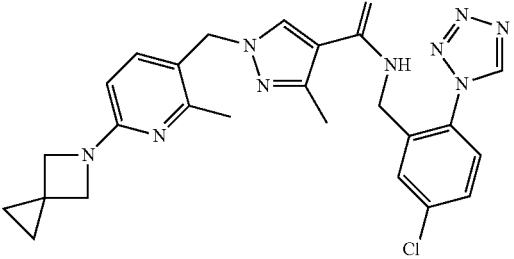 | 0.79 | 504 | Method 6 |
| 30 | 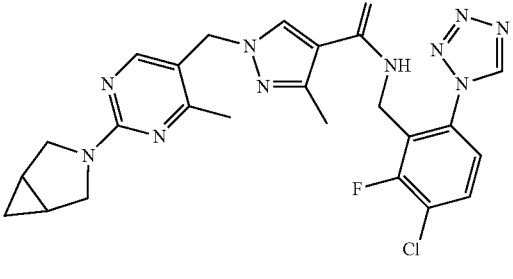 | 0.77 | 523 | Method 6 |
| 31 | 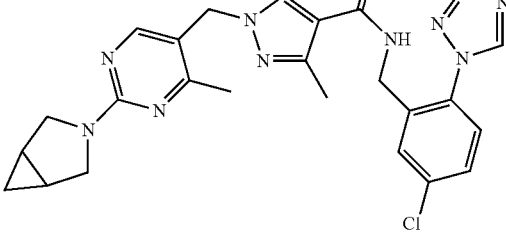 | 0.76 | 505 | Method 6 |

-continued

| Example | Structure | $t_R$ | Mass spectrum (ESI+): m/z [M + H]+ | LC Method |
|---|---|---|---|---|
| 32 | 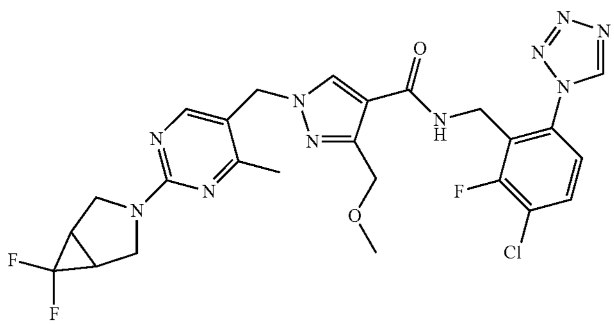 [SMILES: COCc1nn(Cc2cnc(N3CC4C(C3)C4(F)F)nc2C)cc1C(=O)NCc1c(-n2cnnn2)ccc(Cl)c1F] | 0.81 | 589 | Method 6 |
| 33 | 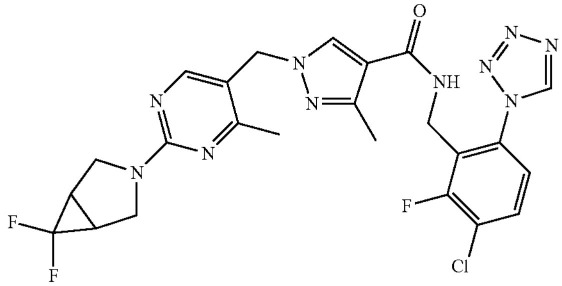 [SMILES: Cc1nc(N2CC3C(C2)C3(F)F)ncc1Cn1cc(C(=O)NCc2c(-n3cnnn3)ccc(Cl)c2F)c(C)n1] | 0.77 | 559 | Method 6 |
| 34 | 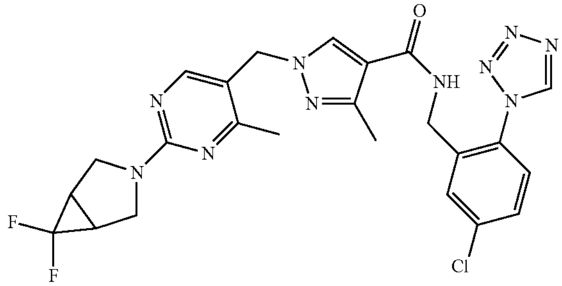 [SMILES: Cc1nc(N2CC3C(C2)C3(F)F)ncc1Cn1cc(C(=O)NCc2cc(Cl)ccc2-n2cnnn2)c(C)n1] | 0.76 | 541 | Method 6 |
| 35 | 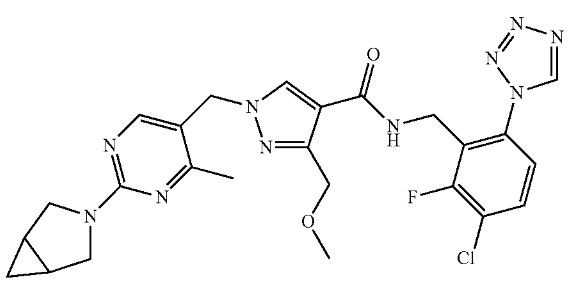 [SMILES: COCc1nn(Cc2cnc(N3CC4CC4C3)nc2C)cc1C(=O)NCc1c(-n2cnnn2)ccc(Cl)c1F] | 0.82 | 553 | Method 6 |
| 36 | 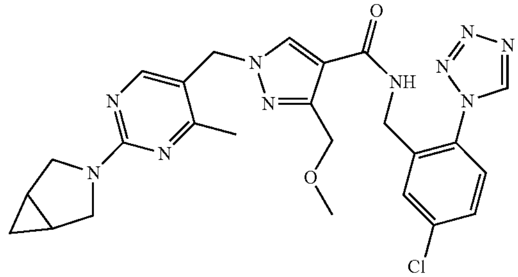 [SMILES: COCc1nn(Cc2cnc(N3CC4CC4C3)nc2C)cc1C(=O)NCc1cc(Cl)ccc1-n1cnnn1] | 0.79 | 535 | Method 6 |

-continued

| Example | Structure | $t_R$ | Mass spectrum (ESI+): m/z [M + H]+ | LC Method |
|---|---|---|---|---|
| 37 | 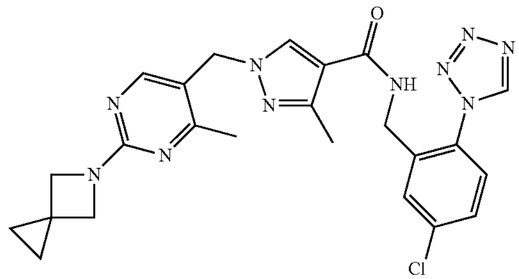 [SMILES: Cc1nc(N2CC3(CC3)C2)ncc1Cn1cc(C(=O)NCc2cc(Cl)ccc2-n2cnnn2)c(C)n1] | 0.72 | 505 | Method 6 |
| 38 | 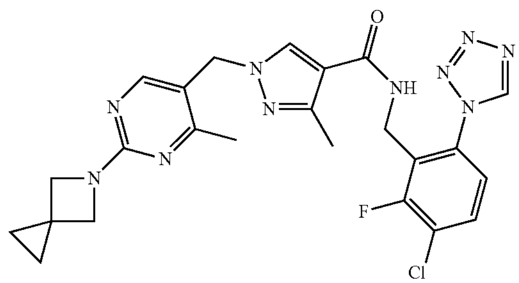 [SMILES: Cc1nc(N2CC3(CC3)C2)ncc1Cn1cc(C(=O)NCc2c(-n3cnnn3)ccc(Cl)c2F)c(C)n1] | 0.73 | 523 | Method 6 |
| 39 | 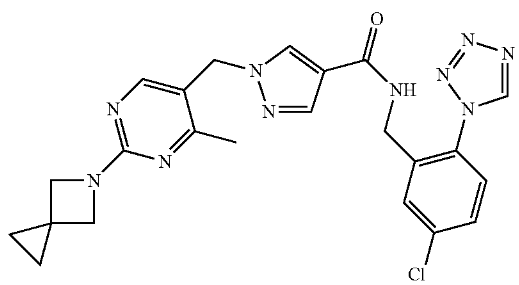 [SMILES: Cc1nc(N2CC3(CC3)C2)ncc1Cn1cc(C(=O)NCc2cc(Cl)ccc2-n2cnnn2)cn1] | 0.68 | 491 | Method 6 |
| 40 | 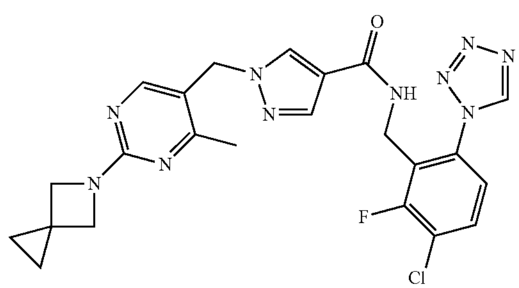 [SMILES: Cc1nc(N2CC3(CC3)C2)ncc1Cn1cc(C(=O)NCc2c(-n3cnnn3)ccc(Cl)c2F)cn1] | 0.70 | 509 | Method 6 |
| 41 | 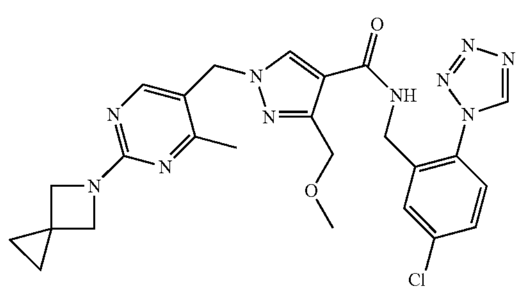 | 0.75 | 535 | Method 6 |

-continued
| Example | Structure | $t_R$ | Mass spectrum (ESI+): m/z [M + H]+ | LC Method |
|---|---|---|---|---|
| 42 | 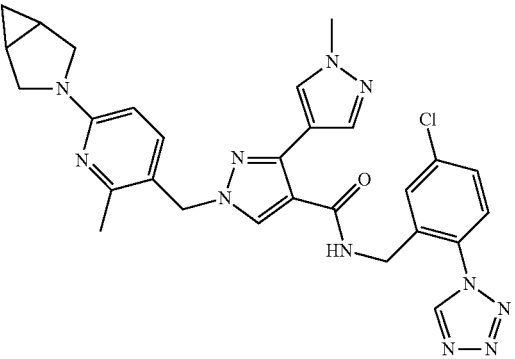 [SMILES: Cc1nc(N2CC3CC3C2)ccc1Cn1cc(C(=O)NCc2cc(Cl)ccc2-n2cnnn2)c(-c2cnn(C)c2)n1] | 0.83 | 570 | Method 7 |
| 43 | 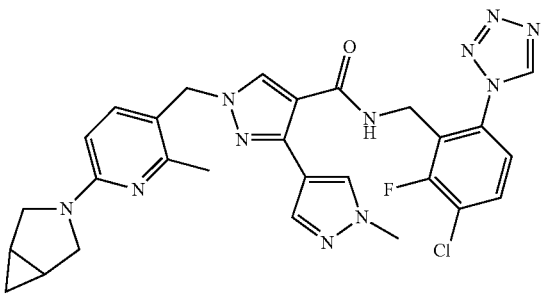 [SMILES: Cc1nc(N2CC3CC3C2)ccc1Cn1cc(C(=O)NCc2c(-n3cnnn3)ccc(Cl)c2F)c(-c2cnn(C)c2)n1] | 0.83 | 588 | Method 6 |
| 44 | 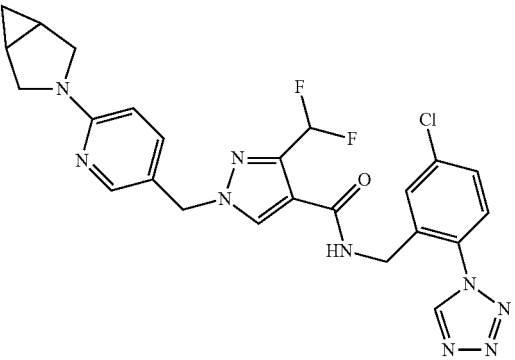 [SMILES: O=C(NCc1cc(Cl)ccc1-n1cnnn1)c1cn(Cc2ccc(N3CC4CC4C3)nc2)nc1C(F)F] | 0.81 | 526 | Method 6 |
| 45 | 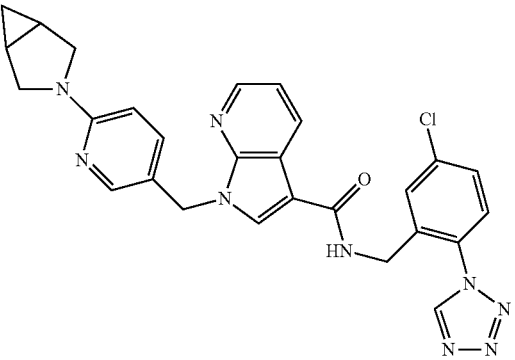 [SMILES: O=C(NCc1cc(Cl)ccc1-n1cnnn1)c1cn(Cc2ccc(N3CC4CC4C3)nc2)c2ncccc12] | 0.83 | 526 | Method 6 |

-continued

| Example | Structure | $t_R$ | Mass spectrum (ESI+): m/z [M + H]+ | LC Method |
|---|---|---|---|---|
| 46 | 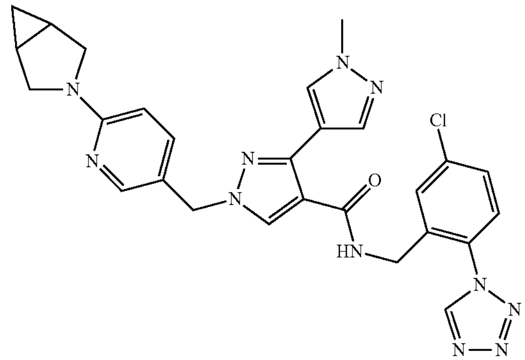 [SMILES: Cn1cc(-c2nn(Cc3ccc(N4CC5CC5C4)nc3)cc2C(=O)NCc2cc(Cl)ccc2-n2cnnn2)cn1] | 0.73 | 556 | Method 6 |
| 47 | 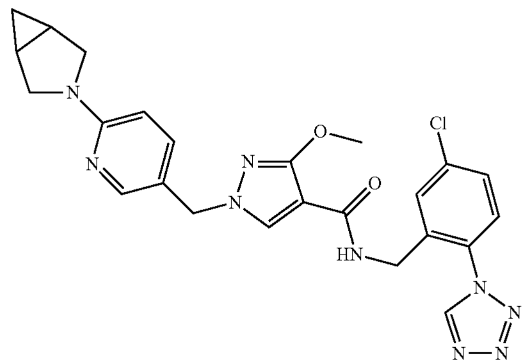 [SMILES: COc1nn(Cc2ccc(N3CC4CC4C3)nc2)cc1C(=O)NCc1cc(Cl)ccc1-n1cnnn1] | 0.80 | 506 | Method 6 |
| 48 | 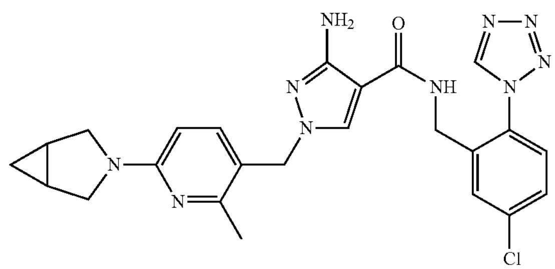 [SMILES: Cc1nc(N2CC3CC3C2)ccc1Cn1cc(C(=O)NCc2cc(Cl)ccc2-n2cnnn2)c(N)n1] | 0.79 | 505 | Method 1 |
| 49 | 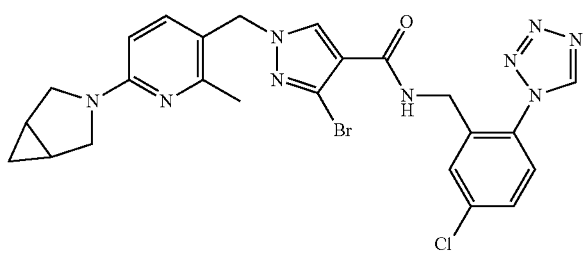 [SMILES: Cc1nc(N2CC3CC3C2)ccc1Cn1cc(C(=O)NCc2cc(Cl)ccc2-n2cnnn2)c(Br)n1] | 0.84 | 568 | Method 1 |
| 50 | 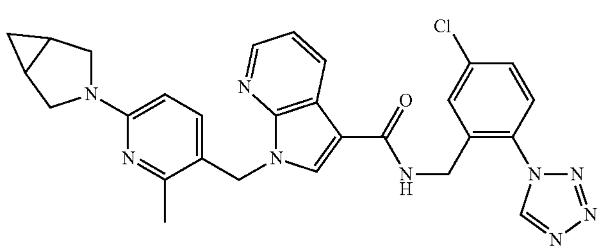 [SMILES: Cc1nc(N2CC3CC3C2)ccc1Cn1cc(C(=O)NCc2cc(Cl)ccc2-n2cnnn2)c2cccnc21] | 0.60 | 540 | Method 5 |

-continued

| Example | Structure | $t_R$ | Mass spectrum (ESI+): m/z [M + H]+ | LC Method |
|---|---|---|---|---|
| 51 | 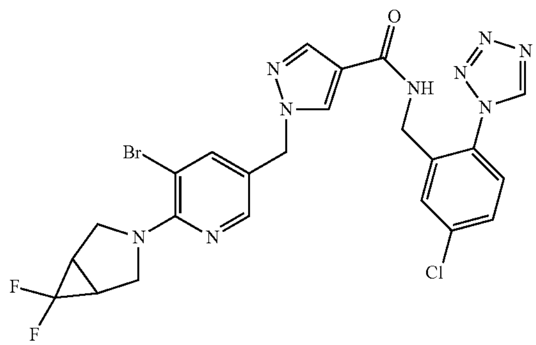 [SMILES: O=C(NCc1cc(Cl)ccc1-n1cnnn1)c1cnn(Cc2cnc(N3CC4C(C3)C4(F)F)c(Br)c2)c1] | 1.04 | 590 | Method 1 |
| 52 | 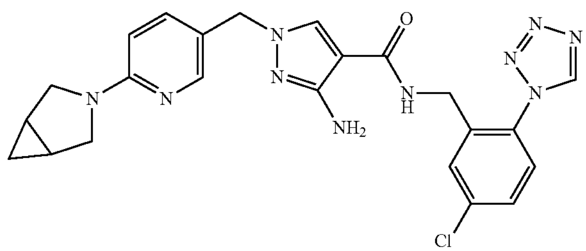 [SMILES: Nc1nn(Cc2ccc(N3CC4CC4C3)nc2)cc1C(=O)NCc1cc(Cl)ccc1-n1cnnn1] | 0.69 | 491 | Method 6 |
| 53 | 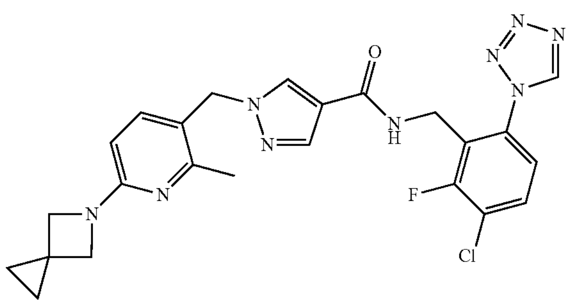 [SMILES: Cc1nc(N2CC3(CC3)C2)ccc1Cn1cc(C(=O)NCc2c(-n3cnnn3)ccc(Cl)c2F)cn1] | 0.97 | 508 | Method 2 |
| 54 | 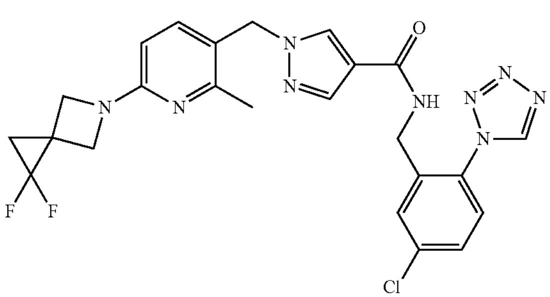 [SMILES: Cc1nc(N2CC3(C2)CC3(F)F)ccc1Cn1cc(C(=O)NCc2cc(Cl)ccc2-n2cnnn2)cn1] | 0.76 | 526 | Method 6 |
| 55 | 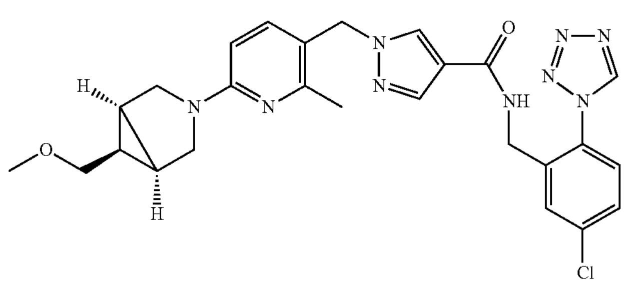 [SMILES: COC[C@H]1[C@H]2CN(c3ccc(Cn4cc(C(=O)NCc5cc(Cl)ccc5-n5cnnn5)cn4)c(C)n3)C[C@@H]12] | 0.75 | 534 | Method 7 |

| Example | Structure | Mass spectrum (ESI+): $t_R$ | m/z [M + H]+ | LC Method |
|---|---|---|---|---|
| 56 | 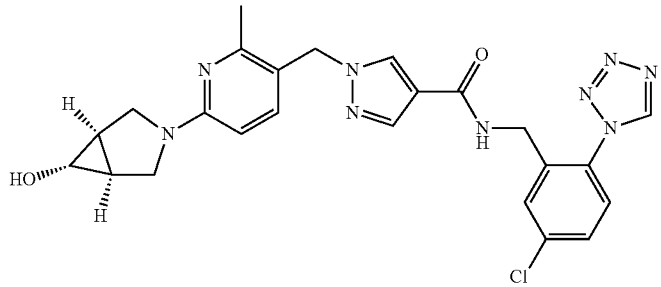 [SMILES: Cc1nc(N2C[C@@H]3[C@@H](O)[C@@H]3C2)ccc1Cn1cc(C(=O)NCc2cc(Cl)ccc2-n2cnnn2)cn1] | 0.61 | 506 | Method 6 |
| 57 | 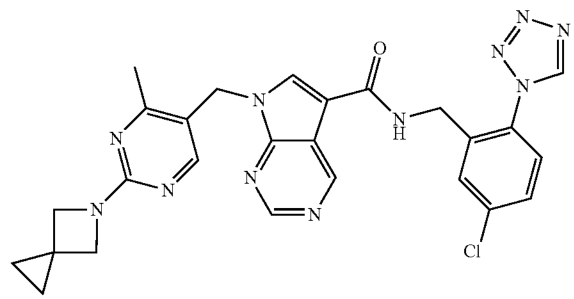 [SMILES: Cc1nc(N2CC3(CC3)C2)ncc1Cn1cc(C(=O)NCc2cc(Cl)ccc2-n2cnnn2)c2cncnc21] | 0.72 | 542 | Method 6 |

| Example | Name | Name of starting material 1 | Name of starting material 2 |
|---|---|---|---|
| 2 | 1-[(6-{3-azabicyclo[3.1.0]hexan-3-yl}-2-methylpyridin-3-yl)methyl]-N-{[5-chloro-4-fluoro-2-(1H-1,2,3,4-tetrazol-1-yl)-phenyl]methyl}-1H-pyrazole-4-carboxamide | 1-[(6-{3-Azabicyclo[3.1.0]-hexan-3-yl}-2-methyl-pyridin-3-yl)methyl]-1H-pyrazole-4-carboxylic acid | [5-chloro-4-fluoro-2-(1H-1,2,3,4-tetrazol-1-yl)phenyl]-methanamine |
| 3 | 1-[(6-{3-azabicyclo[3.1.0]hexan-3-yl}-2-methylpyridin-3-yl)methyl]-N-{[3-chloro-2-fluoro-6-(1H-1,2,3,4-tetrazol-1-yl)-phenyl]methyl}-1H-pyrazole-4-carboxamide | 1-[(6-{3-Azabicyclo[3.1.0]-hexan-3-yl}-2-methyl-pyridin-3-yl)methyl]-1H-pyrazole-4-carboxylic acid | 3-chloro-2-fluoro-6-(1H-1,2,3,4-tetrazol-1-yl)-phenyl]methanamine |
| 4 | 1-[(6-{3-azabicyclo[3.1.0]hexan-3-yl}-2-methylpyridin-3-yl)methyl]-N-{[5-chloro-3-methyl-2-(1H-1,2,3,4-tetrazol-1-yl)-phenyl]methyl}-1H-pyrazole-4-carboxamide | 1-[(6-{3-Azabicyclo[3.1.0]-hexan-3-yl}-2-methyl-pyridin-3-yl)methyl]-1H-pyrazole-4-carboxylic acid | 5-chloro-3-methyl-2-(1H-1,2,3,4-tetrazol-1-yl)-phenyl]methanamine |
| 5 | 1-[(6-{3-azabicyclo[3.1.0]hexan-3-yl}-2-methylpyridin-3-yl)methyl]-N-{[5-methyl-2-(1H-1,2,3,4-tetrazol-1-yl)phenyl]-methyl}-1H-pyrazole-4-carboxamide | 1-[(6-{3-Azabicyclo[3.1.0]-hexan-3-yl}-2-methyl-pyridin-3-yl)methyl]-1H-pyrazole-4-carboxylic acid | [5-methyl-2-(1H-1,2,3,4-tetrazol-1-yl)phenyl]-methanamine |
| 6 | N-{[5-chloro-2-(1H-1,2,3,4-tetrazol-1-yl)phenyl]methyl}-1-[(6-{6,6-difluoro-3-azabicyclo[3.1.0]hexan-3-yl}-2-methyl-pyridin-3-yl)methyl]-1H-pyrazole-4-carboxamide | 1-[(6-{6,6-Difluoro-3-aza-bicyclo[3.1.0]hexan-3-yl}-2-methylpyridin-3-yl)methyl]-1H-pyrazole-4-carboxylic acid | [5-chloro-2-(1H-1,2,3,4-tetrazol-1-yl)phenyl]-methanamine |
| 7 | 1-[(6-{3-azabicyclo[3.1.0]hexan-3-yl}-2-methylpyridin-3-yl)methyl]-3-chloro-N-{[3-chloro-2-fluoro-6-(1H-1,2,3,4-tetrazol-1-yl)phenyl]methyl}-1H-pyrazole-4-carboxamide | 1-[(6-{3-Azabicyclo[3.1.0]-hexan-3-yl}-2-methyl-pyridin-3-yl)methyl]-3-chloro-1H-pyrazole-4-carboxylic acid | 3-chloro-2-fluoro-6-(1H-1,2,3,4-tetrazol-1-yl)-phenyl]methanamine |
| 8 | N-{[5-chloro-2-(1H-1,2,3,4-tetrazol-1-yl)phenyl]methyl}-7-[(6-{6,6-difluoro-3-azabicyclo[3.1.0]hexan-3-yl}-2-methyl-pyridin-3-yl)methyl]-7H-pyrrolo[2,3-d]-pyrimidine-5-carboxamide | 7-[(6-{6,6-Difluoro-3-aza-bicyclo[3.1.0] hexan-3-yl}-2-methylpyridin-3-yl)methyl]-7H-pyrrolo[2,3-d]pyrimidine-5-carboxylic acid | [5-chloro-2-(1H-1,2,3,4-tetrazol-1-yl)phenyl]-methanamine |
| 9 | 1-[(6-{3-azabicyclo[3.1.0]hexan-3-yl}-2-methylpyridin-3-yl)methyl]-N-{[5-chloro-2-(1H-1,2,3,4-tetrazol-1-yl)phenyl]-methyl}-3-(difluoromethyl)-1H-pyrazole-4-carboxamide | 1-[(6-{3-Azabicyclo[3.1.0]-hexan-3-yl}-2-methyl-pyridin-3-yl)methyl]-3-(difluoromethyl)-1H-pyrazole-4-carboxylic acid | [5-chloro-2-(1H-1,2,3,4-tetrazol-1-yl)phenyl]-methanamine |

-continued

| Example | Name | Name of starting material 1 | Name of starting material 2 |
|---|---|---|---|
| 10 | 1-[(6-{3-azabicyclo[3.1.0]hexan-3-yl}-2-methylpyridin-3-yl)methyl]-N-{[3-chloro-2-fluoro-6-(1H-1,2,3,4-tetrazol-1-yl)-phenyl]methyl}-3-(difluoromethyl)-1H-pyrazole-4-carboxamide | 1-[(6-{3-Azabicyclo[3.1.0]-hexan-3-yl}-2-methyl-pyridin-3-yl)methyl]-3-(difluoromethyl)-1H-pyrazole-4-carboxylic acid | 3-chloro-2-fluoro-6-(1H-1,2,3,4-tetrazol-1-yl)-phenyl]methanamine |
| 11 | N-{[3-chloro-2-fluoro-6-(1H-1,2,3,4-tetrazol-1-yl)phenyl]methyl}-1-[(6-{6,6-difluoro-3-azabicyclo[3.1.0]hexan-3-yl}-2-methylpyridin-3-yl)methyl]-3-(methoxymethyl)-1H-pyrazole-4-carboxamide | 1-[(6-{6,6-Difluoro-3-aza-bicyclo[3.1.0] hexan-3-yl}-2-methylpyridin-3-yl)methyl]-3-(methoxymethyl)-1H-pyrazole-4-carboxylic acid | 3-chloro-2-fluoro-6-(1H-1,2,3,4-tetrazol-1-yl)-phenyl]methanamine |
| 12 | N-{[5-chloro-2-(1H-1,2,3,4-tetrazol-1-yl)phenyl]methyl}-1-[(6-{6,6-difluoro-3-azabicyclo[3.1.0]hexan-3-yl}-2-methyl-pyridin-3-yl)methyl]-3-(methoxymethyl)-1H-pyrazole-4-carboxamide | 1-[(6-{6,6-Difluoro-3-aza-bicyclo[3.1.0] hexan-3-yl}-2-methylpyridin-3-yl)methyl]-3-(methoxymethyl)-1H-pyrazole-4-carboxylic acid | [5-chloro-2-(1H-1,2,3,4-tetrazol-1-yl)phenyl]-methanamine |
| 13 | 1-[(6-{3-azabicyclo[3.1.0]hexan-3-yl}-2-methylpyridin-3-yl)methyl]-N-{[5-chloro-2-(1H-1,2,3,4-tetrazol-1-yl)phenyl]-methyl}-3-(methoxymethyl)-1H-pyrazole-4-carboxamide | 1-[(6-{3-Azabicyclo[3.1.0]-hexan-3-yl}-2-methyl-pyridin-3-yl)methyl]-3-(methoxymethyl)-1H-pyrazole-4-carboxylic acid | [5-chloro-2-(1H-1,2,3,4-tetrazol-1-yl)phenyl]-methanamine |
| 14 | 1-[(6-{3-azabicyclo[3.1.0]hexan-3-yl}-2-methylpyridin-3-yl)methyl]-N-{[3-chloro-2-fluoro-6-(1H-1,2,3,4-tetrazol-1-yl)-phenyl]methyl}-3-(methoxymethyl)-1H-pyrazole-4-carboxamide | 1-[(6-{3-Azabicyclo[3.1.0]-hexan-3-yl}-2-methyl-pyridin-3-yl)methyl]-3-(methoxymethyl)-1H-pyrazole-4-carboxylic acid | 3-chloro-2-fluoro-6-(1H-1,2,3,4-tetrazol-1-yl)-phenyl]methanamine |
| 15 | 7-[(6-{3-azabicyclo[3.1.0]hexan-3-yl}-2-methylpyridin-3-yl)methyl]-N-{[5-chloro-2-(1H-1,2,3,4-tetrazol-1-yl)phenyl]-methyl}-7H-pyrrolo[2,3-d]pyrimidine-5-carboxamide | 7-[(6-{3-Azabicyclo[3.1.0]-hexan-3-yl}-2-methyl-pyridin-3-yl)methyl]-7H-pyrrolo[2,3-d]pyrimidine-5-carboxylic acid | [5-chloro-2-(1H-1,2,3,4-tetrazol-1-yl)phenyl]-methanamine |
| 16 | 7-[(6-{3-azabicyclo[3.1.0]hexan-3-yl}-2-methylpyridin-3-yl)methyl]-N-{[3-chloro-2-fluoro-6-(1H-1,2,3,4-tetrazol-1-yl)-phenyl]methyl}-7H-pyrrolo[2,3-d]-pyrimidine-5-carboxamide | 7-[(6-{3-Azabicyclo[3.1.0]-hexan-3-yl}-2-methyl-pyridin-3-yl)methyl]-7H-pyrrolo[2,3-d]pyrimidine-5-carboxylic acid | 3-chloro-2-fluoro-6-(1H-1,2,3,4-tetrazol-1-yl)-phenyl]methanamine |
| 17 | N-{[3-chloro-2-fluoro-6-(1H-1,2,3,4-tetrazol-1-yl)phenyl]methyl}-1-[(6-{6,6-difluoro-3-azabicyclo[3.1.0]hexan-3-yl}-2-methylpyridin-3-yl)methyl]-3-methyl-1H-pyrazole-4-carboxamide | 1-[(6-{6,6-Difluoro-3-aza-bicyclo[3.1.0]hexan-3-yl}-2-methylpyridin-3-yl)methyl]-3-methyl-1H-pyrazole-4-carboxylic acid | 3-chloro-2-fluoro-6-(1H-1,2,3,4-tetrazol-1-yl)-phenyl]methanamine |
| 18 | N-{[5-chloro-2-(1H-1,2,3,4-tetrazol-1-yl)phenyl]methyl}-1-[(6-{6,6-difluoro-3-azabicyclo[3.1.0]hexan-3-yl}-2-methyl-pyridin-3-yl)methyl]-3-methyl-1H-pyrazole-4-carboxamide | 1-[(6-{6,6-Difluoro-3-aza-bicyclo[3.1.0]hexan-3-yl}-2-methylpyridin-3-yl)methyl]-3-methyl-1H-pyrazole-4-carboxylic acid | [5-chloro-2-(1H-1,2,3,4-tetrazol-1-yl)phenyl]-methanamine |
| 19 | 1-[(6-{3-azabicyclo[3.1.0]hexan-3-yl}-2-methylpyridin-3-yl)methyl]-N-{[5-chloro-2-(1H-1,2,3,4-tetrazol-1-yl)phenyl]-methyl}-3-methyl-1H-pyrazole-4-carboxamide | 1-[(6-{3-Azabicyclo[3.1.0]-hexan-3-yl}-2-methyl-pyridin-3-yl)methyl]-3-methyl-1H-pyrazole-4-carboxylic acid | [5-chloro-2-(1H-1,2,3,4-tetrazol-1-yl)phenyl]-methanamine |
| 20 | 1-[(6-{3-azabicyclo[3.1.0]hexan-3-yl}-2-methylpyridin-3-yl)methyl]-N-{[3-chloro-2-fluoro-6-(1H-1,2,3,4-tetrazol-1-yl)-phenyl]methyl}-3-methyl-1H-pyrazole-4-carboxamide | 1-[(6-{3-Azabicyclo[3.1.0]-hexan-3-yl}-2-methyl-pyridin-3-yl)methyl]-3-methyl-1H-pyrazole-4-carboxylic acid | 3-chloro-2-fluoro-6-(1H-1,2,3,4-tetrazol-1-yl)-phenyl]methanamine |
| 21 | 1-[(6-{3-azabicyclo[3.1.0]hexan-3-yl}-2-methylpyridin-3-yl)methyl]-N-{[5-chloro-2-(1H-1,2,3,4-tetrazol-1-yl)phenyl]-methyl}-3-methoxy-1H-pyrazole-4-carboxamide | 1-[(6-{3-Azabicyclo[3.1.0]-hexan-3-yl}-2-methyl-pyridin-3-yl)methyl]-3-methoxy-1H-pyrazole-4-carboxylic acid | [5-chloro-2-(1H-1,2,3,4-tetrazol-1-yl)phenyl]-methanamine |
| 22 | 1-[(6-{3-azabicyclo[3.1.0]hexan-3-yl}-2-methylpyridin-3-yl)methyl]-N-{[3-chloro-2-fluoro-6-(1H-1,2,3,4-tetrazol-1-yl)-phenyl]methyl}-3-methoxy-1H-pyrazole-4-carboxamide | 1-[(6-{3-Azabicyclo[3.1.0]-hexan-3-yl}-2-methyl-pyridin-3-yl)methyl]-3-methoxy-1H-pyrazole-4-carboxylic acid | 3-chloro-2-fluoro-6-(1H-1,2,3,4-tetrazol-1-yl)-phenyl]methanamine |
| 23 | N-{[3-chloro-2-fluoro-6-(1H-1,2,3,4-tetrazol-1-yl)phenyl]methyl}-7-[(2-{6,6-difluoro-3-azabicyclo[3.1.0]hexan-3-yl}-4-methylpyrimidin-5-yl)methyl]-7H-pyrrolo[2,3-d]pyrimidine-5-carboxamide | 7-[(2-{6,6-Difluoro-3-aza-bicyclo[3.1.0]hexan-3-yl}-4-methylpyrimidin-5-yl)-methyl]-7H-pyrrolo[2,3-d]-pyrimidine-5-carboxylic acid | 3-chloro-2-fluoro-6-(1H-1,2,3,4-tetrazol-1-yl)-phenyl]methanamine |
| 24 | N-{[5-chloro-2-(1H-1,2,3,4-tetrazol-1-yl)phenyl]methyl}-7-[(2-{6,6-difluoro-3-azabicyclo[3.1.0]hexan-3-yl}-4-methyl-pyrimidin-5-yl)methyl]-7H-pyrrolo[2,3-d]pyrimidine-5-carboxamide | 7-[(2-{6,6-Difluoro-3-aza-bicyclo[3.1.0]hexan-3-yl}-4-methylpyrimidin-5-yl)-methyl]-7H-pyrrolo[2,3-d]-pyrimidine-5-carboxylic acid | [5-chloro-2-(1H-1,2,3,4-tetrazol-1-yl)phenyl]-methanamine |

-continued

| Example | Name | Name of starting material 1 | Name of starting material 2 |
|---|---|---|---|
| 25 | 1-[(6-{5-azaspiro[2.3]hexan-5-yl}-2-methylpyridin-3-yl)methyl]-N-{[5-chloro-2-(1H-1,2,3,4-tetrazol-1-yl)phenyl]methyl}-3-(methoxymethyl)-1H-pyrazole-4-carboxamide | 1-[(6-{5-Azaspiro[2.3]hexan-5-yl}-2-methylpyridin-3-yl)methyl]-3-(methoxymethyl)-1H-pyrazole-4-carboxylic acid | [5-chloro-2-(1H-1,2,3,4-tetrazol-1-yl)phenyl]methanamine |
| 26 | 7-[(2-{3-azabicyclo[3.1.0]hexan-3-yl}-4-methylpyrimidin-5-yl)methyl]-N-{[3-chloro-2-fluoro-6-(1H-1,2,3,4-tetrazol-1-yl)phenyl]methyl}-7H-pyrrolo[2,3-d]pyrimidine-5-carboxamide | 7-[(2-{3-Azabicyclo[3.1.0]hexan-3-yl}-4-methylpyrimidin-5-yl)methyl]-7H-pyrrolo[2,3-d]pyrimidine-5-carboxylic acid | 3-chloro-2-fluoro-6-(1H-1,2,3,4-tetrazol-1-yl)phenyl]methanamine |
| 27 | 7-[(2-{3-azabicyclo[3.1.0]hexan-3-yl}-4-methylpyrimidin-5-yl)methyl]-N-{[5-chloro-2-(1H-1,2,3,4-tetrazol-1-yl)phenyl]methyl}-7H-pyrrolo[2,3-d]pyrimidine-5-carboxamide | 7-[(2-{3-Azabicyclo[3.1.0]hexan-3-yl}-4-methylpyrimidin-5-yl)methyl]-7H-pyrrolo[2,3-d]pyrimidine-5-carboxylic acid | [5-chloro-2-(1H-1,2,3,4-tetrazol-1-yl)phenyl]methanamine |
| 28 | 1-[(6-{5-azaspiro[2.3]hexan-5-yl}-2-methylpyridin-3-yl)methyl]-N-{[3-chloro-2-fluoro-6-(1H-1,2,3,4-tetrazol-1-yl)phenyl]methyl}-3-methyl-1H-pyrazole-4-carboxamide | 1-[(6-{5-Azaspiro[2.3]hexan-5-yl}-2-methylpyridin-3-yl)methyl]-3-methyl-1H-pyrazole-4-carboxylic acid | 3-chloro-2-fluoro-6-(1H-1,2,3,4-tetrazol-1-yl)phenyl]methanamine |
| 29 | 1-[(6-{5-azaspiro[2.3]hexan-5-yl}-2-methylpyridin-3-yl)methyl]-N-{[5-chloro-2-(1H-1,2,3,4-tetrazol-1-yl)-phenyl]methyl}-3-methyl-1H-pyrazole-4-carboxamide | 1-[(6-{5-Azaspiro[2.3]hexan-5-yl}-2-methylpyridin-3-yl)methyl]-3-methyl-1H-pyrazole-4-carboxylic acid | [5-chloro-2-(1H-1,2,3,4-tetrazol-1-yl)phenyl]methanamine |
| 30 | 1-[(2-{3-azabicyclo[3.1.0]hexan-3-yl}-4-methylpyrimidin-5-yl)methyl]-N-{[3-chloro-2-fluoro-6-(1H-1,2,3,4-tetrazol-1-yl)phenyl]methyl}-3-methyl-1H-pyrazole-4-carboxamide | 1-[(2-{3-Azabicyclo[3.1.0]hexan-3-yl}-4-methylpyrimidin-5-yl)methyl]-3-methyl-1H-pyrazole-4-carboxylic acid | 3-chloro-2-fluoro-6-(1H-1,2,3,4-tetrazol-1-yl)-phenyl]-methanamine |
| 31 | 1-[(2-{3-azabicyclo[3.1.0]hexan-3-yl}-4-methylpyrimidin-5-yl)methyl]-N-{[5-chloro-2-(1H-1,2,3,4-tetrazol-1-yl)phenyl]methyl}-3-methyl-1H-pyrazole-4-carboxamide | 1-[(2-{3-Azabicyclo[3.1.0]hexan-3-yl}-4-methylpyrimidin-5-yl)methyl]-3-methyl-1H-pyrazole-4-carboxylic acid | [5-chloro-2-(1H-1,2,3,4-tetrazol-1-yl)phenyl]methanamine |
| 32 | N-{[3-chloro-2-fluoro-6-(1H-1,2,3,4-tetrazol-1-yl)phenyl]methyl}-1-[(2-{6,6-difluoro-3-azabicyclo[3.1.0]hexan-3-yl}-4-methylpyrimidin-5-yl)methyl]-3-(methoxymethyl)-1H-pyrazole-4-carboxamide | 1-[(2-{6,6-Difluoro-3-azabicyclo[3.1.0] hexan-3-yl}-4-methylpyrimidin-5-yl)methyl]-3-(methoxymethyl)-1H-pyrazole-4-carboxylic acid | 3-chloro-2-fluoro-6-(1H-1,2,3,4-tetrazol-1-yl)phenyl]methanamine |
| 33 | N-{[3-chloro-2-fluoro-6-(1H-1,2,3,4-tetrazol-1-yl)phenyl]methyl}-1-[(2-{6,6-difluoro-3-azabicyclo[3.1.0]hexan-3-yl}-4-methylpyrimidin-5-yl)methyl]-3-methyl-1H-pyrazole-4-carboxamide | 1-[(2-{6,6-Difluoro-3-azabicyclo[3.1.0] hexan-3-yl}-4-methylpyrimidin-5-yl)methyl]-3-methyl-1H-pyrazole-4-carboxylic acid | 3-chloro-2-fluoro-6-(1H-1,2,3,4-tetrazol-1-yl)phenyl]methanamine |
| 34 | N-{[5-chloro-2-(1H-1,2,3,4-tetrazol-1-yl)phenyl]methyl}-1-[(2-{6,6-difluoro-3-azabicyclo[3.1.0]hexan-3-yl}-4-methylpyrimidin-5-yl)methyl]-3-methyl-1H-pyrazole-4-carboxamide | 1-[(2-{6,6-Difluoro-3-azabicyclo[3.1.0]hexan-3-yl}-4-methylpyrimidin-5-yl)methyl]-3-methyl-1H-pyrazole-4-carboxylic acid | [5-chloro-2-(1H-1,2,3,4-tetrazol-1-yl)phenyl]methanamine |
| 35 | 1-[(2-{3-azabicyclo[3.1.0]hexan-3-yl}-4-methylpyrimidin-5-yl)methyl]-N-{[3-chloro-2-fluoro-6-(1H-1,2,3,4-tetrazol-1-yl)phenyl]methyl}-3-(methoxymethyl)-1H-pyrazole-4-carboxamide | 1-[(2-{3-Azabicyclo[3.1.0]hexan-3-yl}-4-methylpyrimidin-5-yl)methyl]-3-(methoxymethyl)-1H-pyrazole-4-carboxylic acid | 3-chloro-2-fluoro-6-(1H-1,2,3,4-tetrazol-1-yl)phenyl]methanamine |
| 36 | 1-[(2-{3-azabicyclo[3.1.0]hexan-3-yl}-4-methylpyrimidin-5-yl)methyl]-N-{[5-chloro-2-(1H-1,2,3,4-tetrazol-1-yl)phenyl]methyl}-3-(methoxymethyl)-1H-pyrazole-4-carboxamide | 1-[(2-{3-Azabicyclo[3.1.0]hexan-3-yl}-4-methylpyrimidin-5-yl)methyl]-3-(methoxymethyl)-1H-pyrazole-4-carboxylic acid | [5-chloro-2-(1H-1,2,3,4-tetrazol-1-yl)phenyl]methanamine |
| 37 | 1-[(2-{5-azaspiro[2.3]hexan-5-yl}-4-methylpyrimidin-5-yl)methyl]-N-{[5-chloro-2-(1H-1,2,3,4-tetrazol-1-yl)phenyl]methyl}-3-methyl-1H-pyrazole-4-carboxamide | 1-[(2-{5-Azaspiro[2.3]hexan-5-yl}-4-methylpyrimidin-5-yl)methyl]-3-methyl-1H-pyrazole-4-carboxylic acid | [5-chloro-2-(1H-1,2,3,4-tetrazol-1-yl)phenyl]methanamine |
| 38 | 1-[(2-{5-azaspiro[2.3]hexan-5-yl}-4-methylpyrimidin-5-yl)methyl]-N-{[3-chloro-2-fluoro-6-(1H-1,2,3,4-tetrazol-1-yl) phenyl]methyl}-3-methyl-1H-pyrazole-4-carboxamide | 1-[(2-{5-Azaspiro[2.3]hexan-5-yl}-4-methylpyrimidin-5-yl)methyl]-3-methyl-1H-pyrazole-4-carboxylic acid | 3-chloro-2-fluoro-6-(1H-1,2,3,4-tetrazol-1-yl)phenyl]methanamine |
| 39 | 1-[(2-{5-azaspiro[2.3]hexan-5-yl}-4-methylpyrimidin-5-yl)methyl]-N-{[5-chloro-2-(1H-1,2,3,4-tetrazol-1-yl)phenyl]methyl}-1H-pyrazole-4-carboxamide | 1-[(2-{5-Azaspiro[2.3]hexan-5-yl}-4-methylpyrimidin-5-yl)methyl]-1H-pyrazole-4-carboxylic acid | [5-chloro-2-(1H-1,2,3,4-tetrazol-1-yl)phenyl]methanamine |

-continued

| Example | Name | Name of starting material 1 | Name of starting material 2 |
|---|---|---|---|
| 40 | 1-[(2-{5-azaspiro[2.3]hexan-5-yl}-4-methylpyrimidin-5-yl)methyl]-N-{[3-chloro-2-fluoro-6-(1H-1,2,3,4-tetrazol-1-yl)phenyl]methyl}-1H-pyrazole-4-carboxamide | 1-[(2-{5-Azaspiro[2.3]hexan-5-yl}-4-methylpyrimidin-5-yl)methyl]-1H-pyrazole-4-carboxylic acid | 3-chloro-2-fluoro-6-(1H-1,2,3,4-tetrazol-1-yl)phenyl]methanamine |
| 41 | 1-[(2-{5-azaspiro[2.3]hexan-5-yl}-4-methylpyrimidin-5-yl)methyl]-N-{[5-chloro-2-(1H-1,2,3,4-tetrazol-1-yl)phenyl]methyl}-3-(methoxymethyl)-1H-pyrazole-4-carboxamide | 1-[(2-{5-Azaspiro[2.3]hexan-5-yl}-4-methylpyrimidin-5-yl)methyl]-3-(methoxymethyl)-1H-pyrazole-4-carboxylic acid | [5-chloro-2-(1H-1,2,3,4-tetrazol-1-yl)phenyl]methanamine |
| 42 | 1-[(6-{3-azabicyclo[3.1.0]hexan-3-yl}-2-methylpyridin-3-yl)methyl]-N-{[5-chloro-2-(1H-1,2,3,4-tetrazol-1-yl)phenyl]methyl}-1'-methyl-1H,1'H-[3,4'-bipyrazole]-4-carboxamide | 1-[(6-{3-Azabicyclo[3.1.0]hexan-3-yl}-2-methylpyridin-3-yl)methyl]-3-(1-methyl-1H-pyrazol-4-yl)-1H-pyrazole-4-carboxylic acid | [5-chloro-2-(1H-1,2,3,4-tetrazol-1-yl)phenyl]methanamine |
| 43 | 1-[(6-{3-azabicyclo[3.1.0]hexan-3-yl}-2-methylpyridin-3-yl)methyl]-N-{[3-chloro-2-fluoro-6-(1H-1,2,3,4-tetrazol-1-yl)phenyl]methyl}-1'-methyl-1H,1'H-[3,4'-bipyrazole]-4-carboxamide | 1-[(6-{3-Azabicyclo[3.1.0]hexan-3-yl}-2-methylpyridin-3-yl)methyl]-3-(1-methyl-1H-pyrazol-4-yl)-1H-pyrazole-4-carboxylic acid | 3-chloro-2-fluoro-6-(1H-1,2,3,4-tetrazol-1-yl)phenyl]methanamine |
| 44 | 1-[(6-{3-azabicyclo[3.1.0]hexan-3-yl}-pyridin-3-yl)methyl]-N-{[5-chloro-2-(1H-1,2,3,4-tetrazol-1-yl)phenyl]-methyl}-3-(difluoromethyl)-1H-pyrazole-4-carboxamide | 1-[(6-{3-azabicyclo[3.1.0]hexan-3-yl}pyridin-3-yl)methyl]-3-(difluoromethyl)-1H-pyrazole-4-carboxylic acid | [5-chloro-2-(1H-1,2,3,4-tetrazol-1-yl)phenyl]methanamine |
| 45 | 1-[(6-{3-azabicyclo[3.1.0]hexan-3-yl}-pyridin-3-yl)methyl]-N-{[5-chloro-2-(1H-1,2,3,4-tetrazol-1-yl) phenyl]methyl}-1H-pyrrolo[2,3-b]pyridine-3-carboxamide | 1-[(6-{3-azabicyclo[3.1.0]hexan-3-yl}pyridin-3-yl)methyl]-1H-pyrrolo[2,3-b]pyridine-3-carboxylic acid | [5-chloro-2-(1H-1,2,3,4-tetrazol-1-yl)phenyl]methanamine |
| 46 | 1-[(6-{3-azabicyclo[3.1.0]hexan-3-yl}-pyridin-3-yl)methyl]-N-{[5-chloro-2-(1H-1,2,3,4-tetrazol-1-yl)phenyl]methyl}-1'-methyl-1H,1'H-[3,4'-bipyrazole]-4-carboxamide | 1-[(6-{3-azabicyclo[3.1.0]hexan-3-yl}pyridin-3-yl)methyl]-3-(1-methyl-1H-pyrazol-4-yl)-1H-pyrazole-4-carboxylic acid | [5-chloro-2-(1H-1,2,3,4-tetrazol-1-yl)phenyl]methanamine |
| 47 | 1-[(6-{3-azabicyclo[3.1.0]hexan-3-yl}-pyridin-3-yl)methyl]-N-{[5-chloro-2-(1H-1,2,3,4-tetrazol-1-yl)phenyl]methyl}-3-methoxy-1H-pyrazole-4-carboxamide | 1-[(6-{3-azabicyclo[3.1.0]hexan-3-yl}pyridin-3-yl)methyl]-3-methoxy-1H-pyrazole-4-carboxylic acid | [5-chloro-2-(1H-1,2,3,4-tetrazol-1-yl)phenyl]methanamine |
| 48 | 3-amino-1-[(6-{3-azabicyclo[3.1.0]hexan-3-yl}-2-methylpyridin-3-yl)methyl]-N-{[5-chloro-2-(1H-1,2,3,4-tetrazol-1-yl)phenyl]methyl}-1H-pyrazole-4-carboxamide | 3-amino-1-[(6-{3-azabicyclo[3.1.0] hexan-3-yl}-2-methylpyridin-3-yl)methyl]-1H-pyrazole-4-carboxylic acid | [5-chloro-2-(1H-1,2,3,4-tetrazol-1-yl)phenyl]methanamine |
| 49 | 1-[(6-{3-azabicyclo[3.1.0]hexan-3-yl}-2-methylpyridin-3-yl)methyl]-3-bromo-N-{[5-chloro-2-(1H-1,2,3,4-tetrazol-1-yl)phenyl] methyl}-1H-pyrazole-4-carboxamide | 1-[(6-{3-azabicyclo[3.1.0]hexan-3-yl}-2-methylpyridin-3-yl)methyl]-3-bromo-1H-pyrazole-4-carboxylic acid | [5-chloro-2-(1H-1,2,3,4-tetrazol-1-yl)phenyl]methanamine |
| 50 | 1-[(6-{3-azabicyclo[3.1.0]hexan-3-yl}-2-methylpyridin-3-yl)methyl]-N-{[5-chloro-2-(1H-1,2,3,4-tetrazol-1-yl)phenyl]methyl}-1H-pyrrolo[2,3-b]pyridine-3-carboxamide | 1-[(6-{3-azabicyclo[3.1.0]hexan-3-yl}-2-methylpyridin-3-yl)methyl]-1H-pyrrolo[2,3-b]pyridine-3-carboxylic acid | [5-chloro-2-(1H-1,2,3,4-tetrazol-1-yl)phenyl]methanamine |
| 51 | 1-[(5-bromo-6-{6,6-difluoro-3-azabicyclo[3.1.0]hexan-3-yl}pyridin-3-yl)methyl]-N-{[5-chloro-2-(1H-1,2,3,4-tetrazol-1-yl)phenyl]methyl}-1H-pyrazole-4-carboxamide | 1-[(5-bromo-6-{6,6-difluoro-3-azabicyclo[3.1.0] hexan-3-yl}pyridin-3-yl)methyl]-1H-pyrazole-4-carboxylic acid | [5-chloro-2-(1H-1,2,3,4-tetrazol-1-yl)phenyl]methanamine |
| 52 | 3-amino-1-[(6-{3-azabicyclo[3.1.0]hexan-3-yl}pyridin-3-yl)methyl]-N-{[5-chloro-2-(1H-1,2,3,4-tetrazol-1-yl)phenyl]methyl}-1H-pyrazole-4-carboxamide | 3-Amino-1-[(6-{3-azabicyclo[3.1.0]hexan-3-yl}pyridin-3-yl)methyl]-1H-pyrazole-4-carboxylic acid | [5-chloro-2-(1H-1,2,3,4-tetrazol-1-yl)phenyl]methanamine |
| 53 | 1-[(6-{5-azaspiro[2.3]hexan-5-yl}-2-methylpyridin-3-yl)methyl]-N-{[3-chloro-2-fluoro-6-(1H-1,2,3,4-tetrazol-1-yl)phenyl]methyl}-1H-pyrazole-4-carboxamide | 1-[(6-{5-Azaspiro[2.3]hexan-5-yl}-2-methylpyridin-3-yl)methyl]-1H-pyrazole-4-carboxylic acid | 3-chloro-2-fluoro-6-(1H-1,2,3,4-tetrazol-1-yl)phenyl]methanamine |
| 54 | N-{[5-chloro-2-(1H-1,2,3,4-tetrazol-1-yl)phenyl]methyl}-1-[(6-{1,1-difluoro-5-azaspiro[2.3]hexan-5-yl}-2-methylpyridin-3-yl)methyl]-1H-pyrazole-4-carboxamide | 1-[(6-{1,1-difluoro-5-azaspiro[2.3]hexan-5-yl}-2-methylpyridin-3-yl)methyl]-1H-pyrazole-4-carboxylic acid | [5-chloro-2-(1H-1,2,3,4-tetrazol-1-yl)phenyl]methanamine |

-continued

| Example | Name | Name of starting material 1 | Name of starting material 2 |
|---|---|---|---|
| 55 | N-{[5-chloro-2-(1H-1,2,3,4-tetrazol-1-yl)phenyl]methyl}-1-({6-[(1R,5S,6R)-6-(methoxymethyl)-3-azabicyclo[3.1.0]hexan-3-yl]-2-methylpyridin-3-yl}methyl)-1H-pyrazole-4-carboxamide | 1-({6-[(1R,5S,6R)-6-(methoxymethyl)-3-azabicyclo[3.1.0]hexan-3-yl]-2-methylpyridin-3-yl}methyl)-1H-pyrazole-4-carboxylic acid | [5-chloro-2-(1H-1,2,3,4-tetrazol-1-yl)phenyl]methanamine |
| 56 | N-{[5-chloro-2-(1H-1,2,3,4-tetrazol-1-yl)phenyl]methyl}-1-({6-[(1R,5S,6R)-6-hydroxy-3-azabicyclo[3.1.0]hexan-3-yl]-2-methylpyridin-3-yl}methyl)-1H-pyrazole-4-carboxamide | 1-({6-[(1 R,5S,6R)-6-hydroxy-3-azabicyclo[3.1.0]hexan-3-yl]-2-methylpyridin-3-yl}methyl)-1H-pyrazole-4-carboxylic acid | [5-chloro-2-(1H-1,2,3,4-tetrazol-1-yl)phenyl]methanamine |
| 57 | 7-[(2-{5-azaspiro[2.3]hexan-5-yl}-4-methylpyrimidin-5-yl)methyl]-N-{[5-chloro-2-(1H-1,2,3,4-tetrazol-1-yl)phenyl]methyl}-7H-pyrrolo[2,3-d]pyrimidine-5-carboxamide | 7-[(2-{5-Azaspiro[2.3]hexan-5-yl}-4-methylpyrimidin-5-yl)methyl]-7H-pyrrolo[2,3-d]pyrimidine-5-carboxylic acid | [5-chloro-2-(1H-1,2,3,4-tetrazol-1-yl)phenyl]methanamine |

Example 58

1-({6-[(1R,5S,6R)-6-amino-3-azabicyclo[3.1.0]hexan-3-yl]-2-methylpyridin-3-yl}methyl)-N-{[5-chloro-2-(1H-1,2,3,4-tetrazol-1-yl)phenyl]methyl}-1H-pyrazole-4-carboxamide

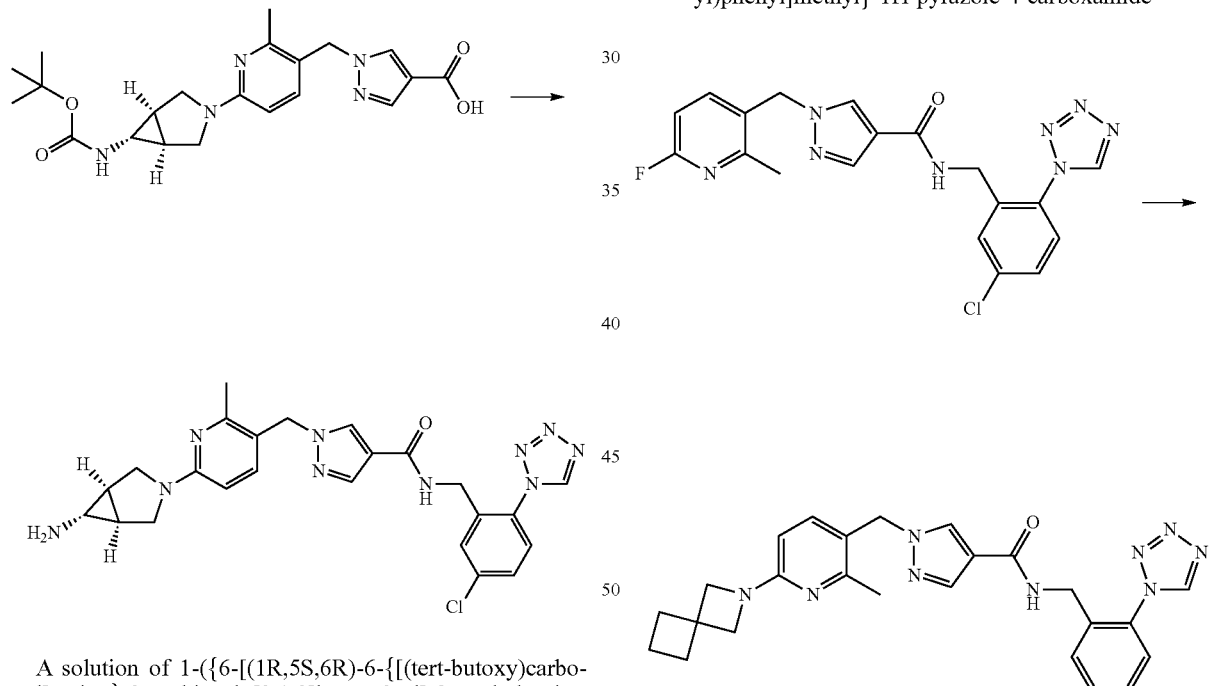

A solution of 1-({6-[(1R,5S,6R)-6-{[(tert-butoxy)carbonyl]amino}-3-azabicyclo[3.1.0]hexan-3-yl]-2-methylpyridin-3-yl}methyl)-1H-pyrazole-4-carboxylic acid trifluoroacetate (16 mg) in DMF (2 mL) is added N,N-diisopropylethylamine (30 µL) and O-(7-azabenzotriazol-1-yl)-N,N,N',N'-tetramethyluronium-hexafluorophosphat (HATU, 13 mg) and stirred for 5 min. [5-chloro-2-(1H-1,2,3,4-tetrazol-1-yl)phenyl]methanamine hydrochloride (10 mg) is added and the mixture is stirred for 16 h. The mixture is filtered through a pad of alumina B, washed with DMF:MeOH=9:1 and concentrated in vacuo. The residue is dissolved in DCM (1 mL) and TFA (1 mL), stirred for 1 h at rt and concentrated in vacuo. The crude product is purified by HPLC on reversed phase (ACN, water) to give the title compound.

LC (Method 6): $t_R$=0.58 min; Mass spectrum (ESI$^+$): m/z=505 [M+H]$^+$.

Example 59

1-[(6-{2-azaspiro[3.3]heptan-2-yl}-2-methylpyridin-3-yl)methyl]-N-{[5-chloro-2-(1H-1,2,3,4-tetrazol-1-yl)phenyl]methyl}-1H-pyrazole-4-carboxamide N-{[5-chloro-2-(1H-1,2,3,4-tetrazol-1-yl)phenyl]methyl}-1-[(6-fluoro-2-methylpyridin-3-yl)methyl]-1H-pyrazole-4-carboxamide (43 mg) dissolved in DMSO (1 mL), 2-azaspiro[3.3]heptane hydrochloride (20 mg) and N,N-diisopropylethylamine (50 µL) are added and the mixture is stirred for 7 d at 60° C. and the mixture is purified by HPLC on reversed phase (ACN, water) to give the title compound.

LC (Method 1): $t_R$=0.83 min; Mass spectrum (ESI$^+$): m/z=504 [M+H]$^+$.

Examples 60-87 are prepared in analogy to example 59:

| Example | Structure | $t_R$ | Mass spectrum (ESI+): m/z [M + H]+ | LC Method |
|---|---|---|---|---|
| 60 | 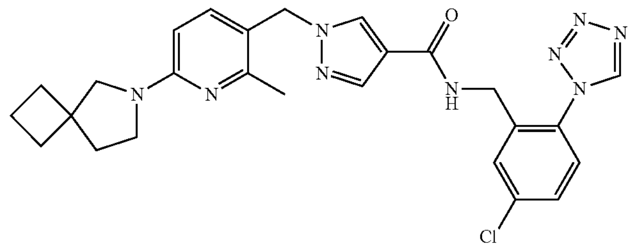 [SMILES: Cc1nc(N2CCC3(CCC3)C2)ccc1Cn1cc(C(=O)NCc2cc(Cl)ccc2-n2cnnn2)cn1] | 0.85 | 518 | Method 1 |
| 61 | 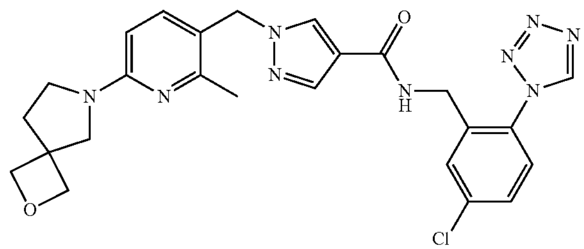 [SMILES: Cc1nc(N2CCC3(COC3)C2)ccc1Cn1cc(C(=O)NCc2cc(Cl)ccc2-n2cnnn2)cn1] | 0.65 | 520 | Method 6 |
| 62 | 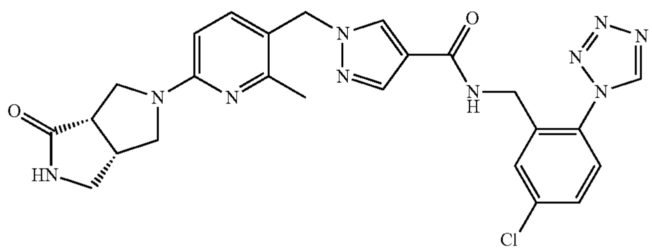 [SMILES: Cc1nc(N2C[C@@H]3CNC(=O)[C@@H]3C2)ccc1Cn1cc(C(=O)NCc2cc(Cl)ccc2-n2cnnn2)cn1] | 0.55 | 533 | Method 6 |
| 63 | 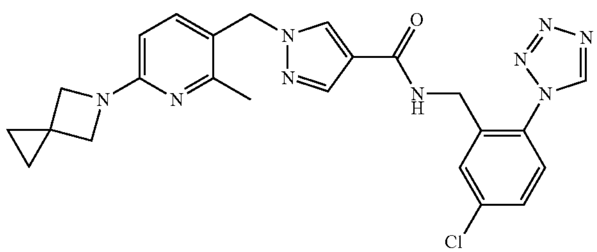 [SMILES: Cc1nc(N2CC3(CC3)C2)ccc1Cn1cc(C(=O)NCc2cc(Cl)ccc2-n2cnnn2)cn1] | 0.75 | 490 | Method 6 |
| 64 | 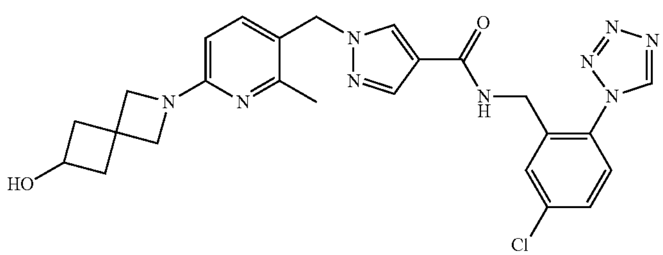 [SMILES: Cc1nc(N2CC3(CC(O)C3)C2)ccc1Cn1cc(C(=O)NCc2cc(Cl)ccc2-n2cnnn2)cn1] | 0.57 | 520 | Method 6 |
| 65 | 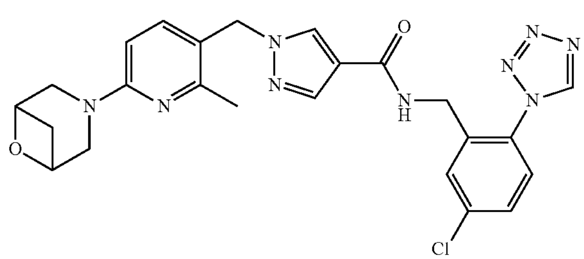 [SMILES: Cc1nc(N2CC3CC(C2)O3)ccc1Cn1cc(C(=O)NCc2cc(Cl)ccc2-n2cnnn2)cn1] | 0.64 | 506 | Method 6 |

-continued

| Example | Structure | $t_R$ | Mass spectrum (ESI+): m/z [M + H]+ | LC Method |
|---|---|---|---|---|
| 66 | 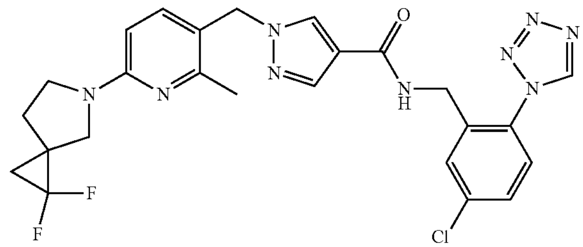 [SMILES: Cc1nc(N2CCC3(C2)CC3(F)F)ccc1Cn1cc(C(=O)NCc2cc(Cl)ccc2-n2cnnn2)cn1] | 0.82 | 540 | Method 6 |
| 67 | 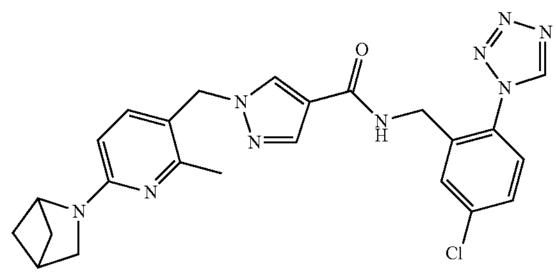 [SMILES: Cc1nc(N2CC3CC2C3)ccc1Cn1cc(C(=O)NCc2cc(Cl)ccc2-n2cnnn2)cn1] | 0.76 | 490 | Method 6 |
| 68 | 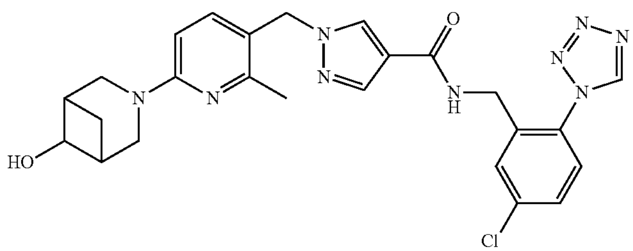 [SMILES: Cc1nc(N2CC3CC(C2)C3O)ccc1Cn1cc(C(=O)NCc2cc(Cl)ccc2-n2cnnn2)cn1] | 0.67 | 520 | Method 6 |
| 69 | 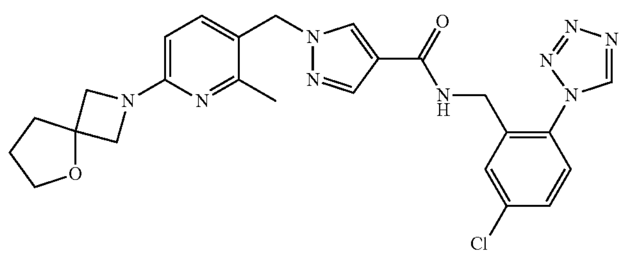 [SMILES: Cc1nc(N2CC3(CCCO3)C2)ccc1Cn1cc(C(=O)NCc2cc(Cl)ccc2-n2cnnn2)cn1] | 0.68 | 520 | Method 6 |
| 70 | 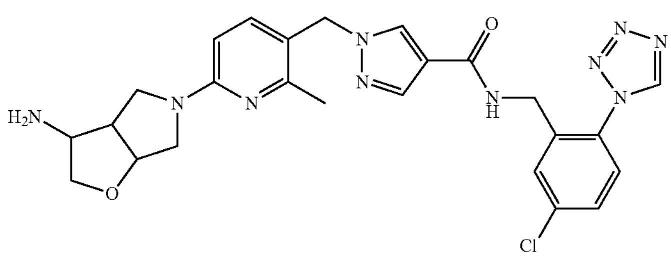 [SMILES: Cc1nc(N2CC3OCC(N)C3C2)ccc1Cn1cc(C(=O)NCc2cc(Cl)ccc2-n2cnnn2)cn1] | 0.54 | 535 | Method 6 |
| 71 | 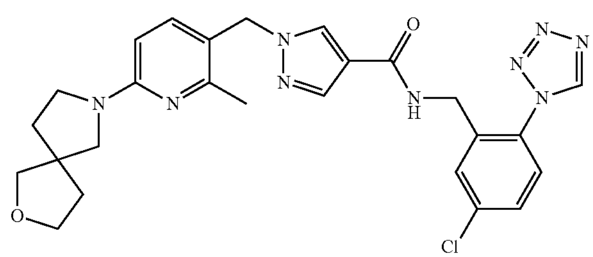 [SMILES: Cc1nc(N2CCC3(CCOC3)C2)ccc1Cn1cc(C(=O)NCc2cc(Cl)ccc2-n2cnnn2)cn1] | 0.70 | 534 | Method 6 |

-continued

| Example | Structure | $t_R$ | Mass spectrum (ESI+): m/z [M + H]+ | LC Method |
|---|---|---|---|---|
| 72 | 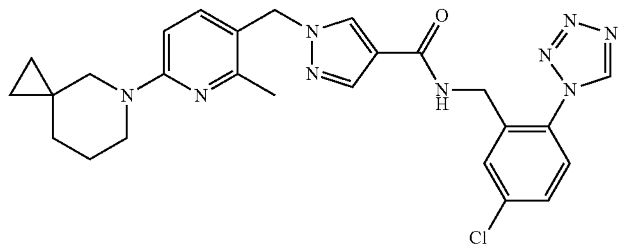 [SMILES: Cc1nc(N2CCCC3(CC3)C2)ccc1Cn1cc(C(=O)NCc2cc(Cl)ccc2-n2cnnn2)cn1] | 0.91 | 518 | Method 6 |
| 73 | 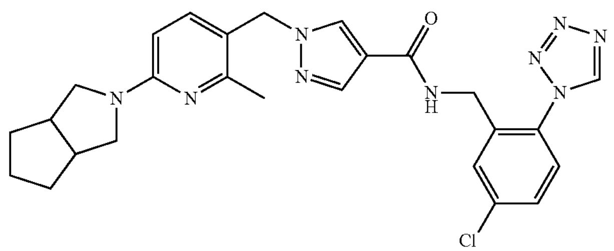 [SMILES: Cc1nc(N2CC3CCCC3C2)ccc1Cn1cc(C(=O)NCc2cc(Cl)ccc2-n2cnnn2)cn1] | 0.91 | 518 | Method 6 |
| 74 | 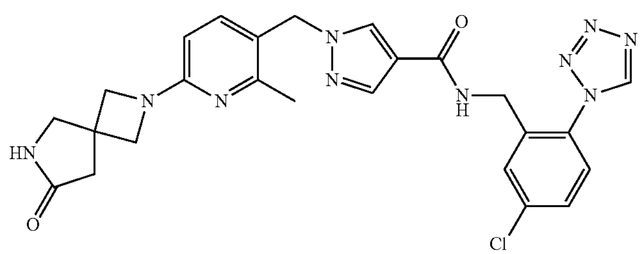 [SMILES: Cc1nc(N2CC3(CNC(=O)C3)C2)ccc1Cn1cc(C(=O)NCc2cc(Cl)ccc2-n2cnnn2)cn1] | 0.52 | 533 | Method 6 |
| 75 | 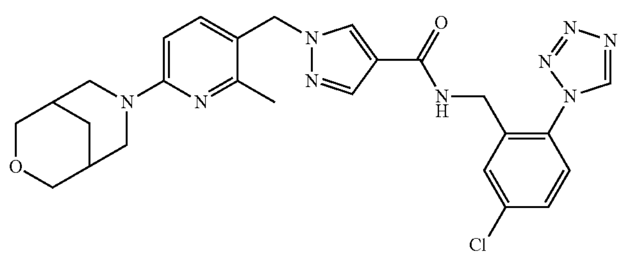 [SMILES: Cc1nc(N2CC3COCC(C3)C2)ccc1Cn1cc(C(=O)NCc2cc(Cl)ccc2-n2cnnn2)cn1] | 0.74 | 534 | Method 6 |
| 76 | 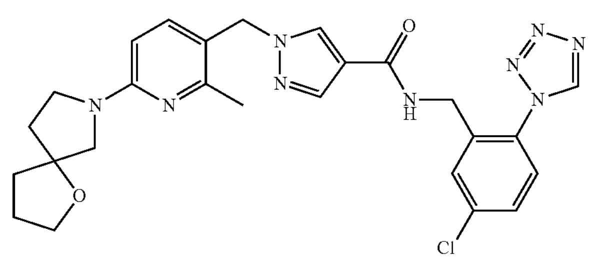 [SMILES: Cc1nc(N2CCC3(CCCO3)C2)ccc1Cn1cc(C(=O)NCc2cc(Cl)ccc2-n2cnnn2)cn1] | 0.74 | 534 | Method 6 |
| 77 | 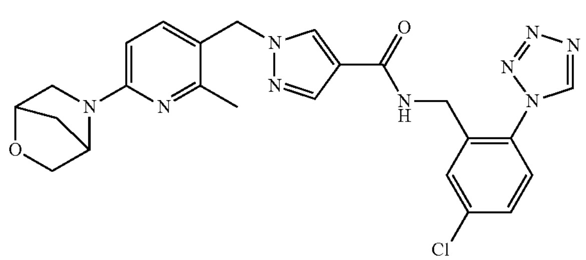 [SMILES: Cc1nc(N2CC3CC2CO3)ccc1Cn1cc(C(=O)NCc2cc(Cl)ccc2-n2cnnn2)cn1] | 0.63 | 506 | Method 6 |

-continued

| Example | Structure | $t_R$ | Mass spectrum (ESI+): m/z [M + H]+ | LC Method |
|---|---|---|---|---|
| 78 | 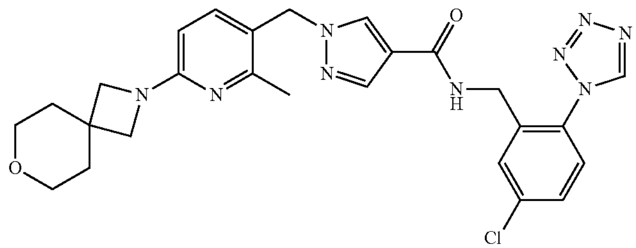 [SMILES: Cc1nc(N2CC3(CCOCC3)C2)ccc1Cn1cc(C(=O)NCc2cc(Cl)ccc2-n2cnnn2)cn1] | 0.66 | 534 | Method 6 |
| 79 | 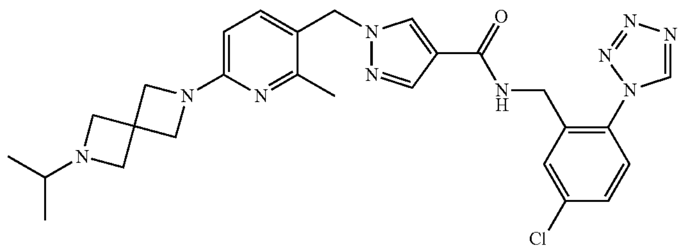 [SMILES: Cc1nc(N2CC3(C2)CN(C(C)C)C3)ccc1Cn1cc(C(=O)NCc2cc(Cl)ccc2-n2cnnn2)cn1] | 0.70 | 547 | Method 6 |
| 80 | 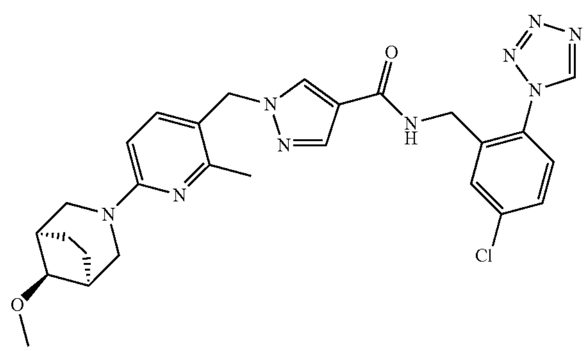 [SMILES: CO[C@H]1[C@@H]2CC[C@H]1CN(c1ccc(Cn3cc(C(=O)NCc4cc(Cl)ccc4-n4cnnn4)cn3)c(C)n1)C2] | 0.85 | 548 | Method 6 |
| 81 | 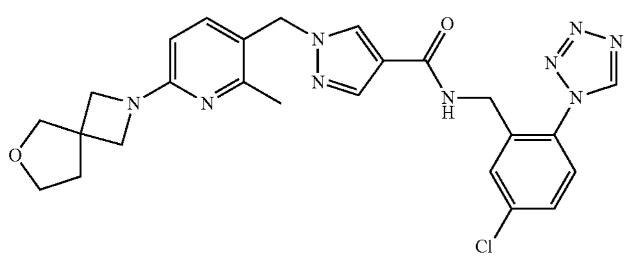 [SMILES: Cc1nc(N2CC3(CCOC3)C2)ccc1Cn1cc(C(=O)NCc2cc(Cl)ccc2-n2cnnn2)cn1] | 0.63 | 520 | Method 6 |
| 82 | 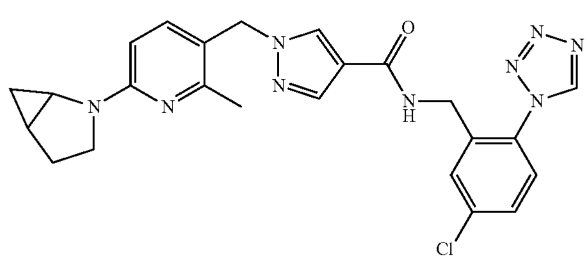 [SMILES: Cc1nc(N2CCC3CC32)ccc1Cn1cc(C(=O)NCc2cc(Cl)ccc2-n2cnnn2)cn1] | 0.77 | 490 | Method 6 |

-continued

| Example | Structure | $t_R$ | Mass spectrum (ESI+): m/z [M + H]+ | LC Method |
|---|---|---|---|---|
| 83 | 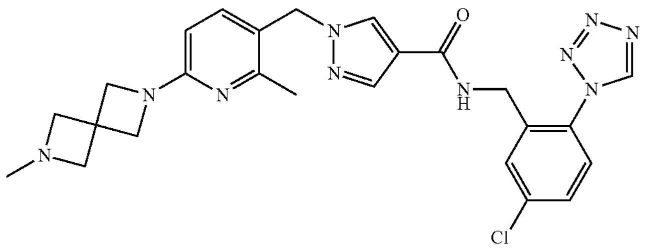 [SMILES: Cc1nc(N2CC3(CN(C)C3)C2)ccc1Cn1cc(C(=O)NCc2cc(Cl)ccc2-n2cnnn2)cn1] | 0.61 | 519 | Method 6 |
| 84 | 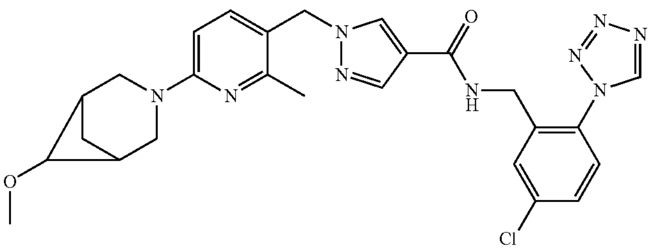 [SMILES: COC1C2CC1CN(c1ccc(Cn3cc(C(=O)NCc4cc(Cl)ccc4-n4cnnn4)cn3)c(C)n1)C2] | 0.80 | 534 | Method 6 |
| 85 | 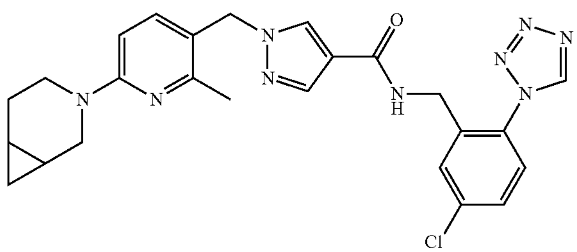 [SMILES: Cc1nc(N2CCC3CC3C2)ccc1Cn1cc(C(=O)NCc2cc(Cl)ccc2-n2cnnn2)cn1] | 0.87 | 504 | Method 6 |
| 86 | 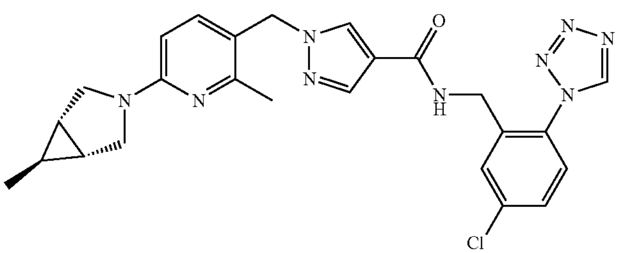 [SMILES: Cc1nc(N2C[C@@H]3[C@@H](C)[C@@H]3C2)ccc1Cn1cc(C(=O)NCc2cc(Cl)ccc2-n2cnnn2)cn1] | 0.89 | 504 | Method 7 |
| 87 | 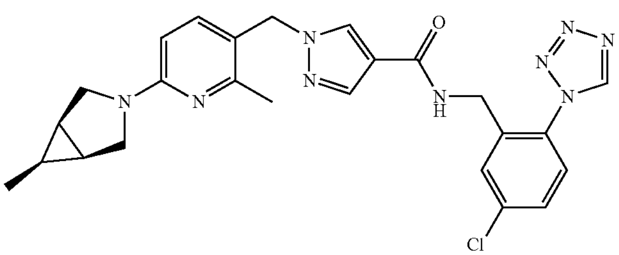 [SMILES: Cc1nc(N2C[C@@H]3[C@H](C)[C@@H]3C2)ccc1Cn1cc(C(=O)NCc2cc(Cl)ccc2-n2cnnn2)cn1] | 0.87 | 504 | Method 7 |

| Example | Name |
|---|---|
| 60 | 1-[(6-{6-azaspiro[3.4]octan-6-yl}-2-methylpyridin-3-yl)methyl]-N-{[5-chloro-2-(1H-1,2,3,4-tetrazol-1-yl)phenyl]methyl}-1H-pyrazole-4-carboxamide |
| 61 | N-{[5-chloro-2-(1H-1,2,3,4-tetrazol-1-yl)phenyl]methyl}-1-[(2-methyl-6-{2-oxa-6-azaspiro[3.4]octan-6-yl}pyridin-3-yl)methyl]-1H-pyrazole-4-carboxamide |
| 62 | 1-({6-[(3aS,6aS)-4-oxo-octahydropyrrolo[3,4-c]pyrrol-2-yl]-2-methylpyridin-3-yl}methyl)-N-{[5-chloro-2-(1H-1,2,3,4-tetrazol-1-yl)phenyl]methyl}-1H-pyrazole-4-carboxamide |
| 63 | 1-[(6-{5-azaspiro[2.3]hexan-5-yl}-2-methylpyridin-3-yl)methyl]-N-{[5-chloro-2-(1H-1,2,3,4-tetrazol-1-yl)phenyl]methyl}-1H-pyrazole-4-carboxamide |

| Example | Name |
|---|---|
| 64 | N-{[5-chloro-2-(1H-1,2,3,4-tetrazol-1-yl)phenyl]methyl}-1-[(6-{6-hydroxy-2-azaspiro[3.3]heptan-2-yl}-2-methylpyridin-3-yl)methyl]-1H-pyrazole-4-carboxamide |
| 65 | N-{[5-chloro-2-(1H-1,2,3,4-tetrazol-1-yl)phenyl]methyl}-1-[(2-methyl-6-{6-oxa-3-azabicyclo[3.1.1]heptan-3-yl}pyridin-3-yl)methyl]-1H-pyrazole-4-carboxamide |
| 66 | N-{[5-chloro-2-(1H-1,2,3,4-tetrazol-1-yl)phenyl]methyl}-1-[(6-{1,1-difluoro-5-azaspiro[2.4]heptan-5-yl}-2-methylpyridin-3-yl)methyl]-1H-pyrazole-4-carboxamide |
| 67 | 1-[(6-{2-azabicyclo[2.1.1]hexan-2-yl}-2-methylpyridin-3-yl)methyl]-N-{[5-chloro-2-(1H-1,2,3,4-tetrazol-1-yl)phenyl]methyl}-1H-pyrazole-4-carboxamide |
| 68 | N-{[5-chloro-2-(1H-1,2,3,4-tetrazol-1-yl)phenyl]methyl}-1-[(6-{6-hydroxy-3-azabicyclo[3.1.1]heptan-3-yl}-2-methylpyridin-3-yl)methyl]-1H-pyrazole-4-carboxamide |
| 69 | N-{[5-chloro-2-(1H-1,2,3,4-tetrazol-1-yl)phenyl]methyl}-1-[(2-methyl-6-{5-oxa-2-azaspiro[3.4]octan-2-yl}pyridin-3-yl)methyl]-1H-pyrazole-4-carboxamide |
| 70 | 1-[(6-{3-amino-hexahydro-2H-furo[2,3-c]pyrrol-5-yl}-2-methylpyridin-3-yl)methyl]-N-{[5-chloro-2-(1H-1,2,3,4-tetrazol-1-yl)phenyl]methyl}-1H-pyrazole-4-carboxamide |
| 71 | N-{[5-chloro-2-(1H-1,2,3,4-tetrazol-1-yl)phenyl]methyl}-1-[(2-methyl-6-{2-oxa-7-azaspiro[4.4]nonan-7-yl}pyridin-3-yl)methyl]-1H-pyrazole-4-carboxamide |
| 72 | 1-[(6-{5-azaspiro[2.5]octan-5-yl}-2-methylpyridin-3-yl)methyl]-N-{[5-chloro-2-(1H-1,2,3,4-tetrazol-1-yl)phenyl]methyl}-1H-pyrazole-4-carboxamide |
| 73 | N-{[5-chloro-2-(1H-1,2,3,4-tetrazol-1-yl)phenyl]methyl}-1-[(2-methyl-6-{octahydrocyclopenta[c]pyrrol-2-yl}pyridin-3-yl)methyl]-1H-pyrazole-4-carboxamide |
| 74 | N-{[5-chloro-2-(1H-1,2,3,4-tetrazol-1-yl)phenyl]methyl}-1-[(2-methyl-6-{7-oxo-2,6-diazaspiro[3.4]octan-2-yl}pyridin-3-yl)methyl]-1H-pyrazole-4-carboxamide |
| 75 | N-{[5-chloro-2-(1H-1,2,3,4-tetrazol-1-yl)phenyl]methyl}-1-[(2-methyl-6-{3-oxa-7-azabicyclo[3.3.1]nonan-7-yl}pyridin-3-yl)methyl]-1H-pyrazole-4-carboxamide |
| 76 | N-{[5-chloro-2-(1H-1,2,3,4-tetrazol-1-yl)phenyl]methyl}-1-[(2-methyl-6-{1-oxa-7-azaspiro[4.4]nonan-7-yl}pyridin-3-yl)methyl]-1H-pyrazole-4-carboxamide |
| 77 | N-{[5-chloro-2-(1H-1,2,3,4-tetrazol-1-yl)phenyl]methyl}-1-[(2-methyl-6-{2-oxa-5-azabicyclo[2.2.1]heptan-5-yl}pyridin-3-yl)methyl]-1H-pyrazole-4-carboxamide |
| 78 | N-{[5-chloro-2-(1H-1,2,3,4-tetrazol-1-yl)phenyl]methyl}-1-[(2-methyl-6-{7-oxa-2-azaspiro[3.5]nonan-2-yl}pyridin-3-yl)methyl]-1H-pyrazole-4-carboxamide |
| 79 | N-{[5-chloro-2-(1H-1,2,3,4-tetrazol-1-yl)phenyl]methyl}-1-({2-methyl-6-[6-(propan-2-yl)-2,6-diazaspiro[3.3]heptan-2-yl]pyridin-3-yl}methyl)-1H-pyrazole-4-carboxamide |
| 80 | N-{[5-chloro-2-(1H-1,2,3,4-tetrazol-1-yl)phenyl]methyl}-1-({6-[(1R,5S,8S)-8-methoxy-3-azabicyclo[3.2.1]octan-3-yl]-2-methylpyridin-3-yl}methyl)-1H-pyrazole-4-carboxamide |
| 81 | N-{[5-chloro-2-(1H-1,2,3,4-tetrazol-1-yl)phenyl]methyl}-1-[(2-methyl-6-{6-oxa-2-azaspiro[3.4]octan-2-yl}pyridin-3-yl)methyl]-1H-pyrazole-4-carboxamide |
| 82 | 1-[(6-{2-azabicyclo[3.1.0]hexan-2-yl}-2-methylpyridin-3-yl)methyl]-N-{[5-chloro-2-(1H-1,2,3,4-tetrazol-1-yl)phenyl]methyl}-1H-pyrazole-4-carboxamide |
| 83 | N-{[5-chloro-2-(1H-1,2,3,4-tetrazol-1-yl)phenyl]methyl}-1-[(2-methyl-6-{6-methyl-2,6-diazaspiro[3.3]heptan-2-yl}pyridin-3-yl)methyl]-1H-pyrazole-4-carboxamide |
| 84 | N-{[5-chloro-2-(1H-1,2,3,4-tetrazol-1-yl)phenyl]methyl}-1-[(6-{6-methoxy-3-azabicyclo[3.1.1]heptan-3-yl}-2-methylpyridin-3-yl)methyl]-1H-pyrazole-4-carboxamide |
| 85 | 1-[(6-{3-azabicyclo[4.1.0]heptan-3-yl}-2-methylpyridin-3-yl)methyl]-N-{[5-chloro-2-(1H-1,2,3,4-tetrazol-1-yl)phenyl]methyl}-1H-pyrazole-4-carboxamide |
| 86 | N-{[5-chloro-2-(1H-1,2,3,4-tetrazol-1-yl)phenyl]methyl}-1-({2-methyl-6-[(1R,5S,6S)-6-methyl-3-azabicyclo[3.1.0]hexan-3-yl]pyridin-3-yl}methyl)-1H-pyrazole-4-carboxamide |
| 87 | N-{[5-chloro-2-(1H-1,2,3,4-tetrazol-1-yl)phenyl]methyl}-1-({2-methyl-6-[(1R,5S,6S)-6-methyl-3-azabicyclo[3.1.0]hexan-3-yl]pyridin-3-yl}methyl)-1H-pyrazole-4-carboxamide |

Example 88

1-({6-[(1R,5S)-1-amino-3-azabicyclo[3.1.0]hexan-3-yl]-2-methylpyridin-3-yl}methyl)-N-{[5-chloro-2-(1H-1,2,3,4-tetrazol-1-yl)phenyl]methyl}-1H-pyrazole-4-carboxamide

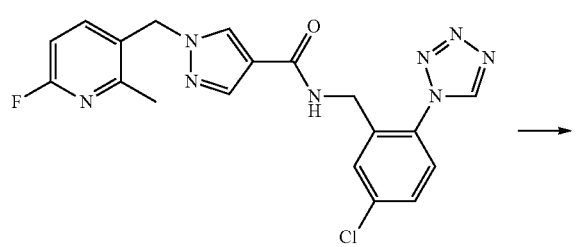

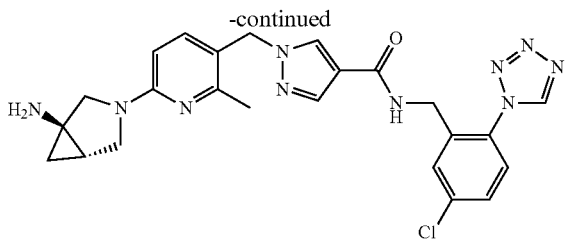

N-{[5-chloro-2-(1H-1,2,3,4-tetrazol-1-yl)phenyl]methyl}-1-[(6-fluoro-2-methylpyridin-3-yl)methyl]-1H-pyrazole-4-carboxamide (43 mg) is dissolved in DMSO (1 mL), tert-butyl N-[(1R,5S)-3-azabicyclo[3.1.0]hexan-1-yl]carbamate (20 mg) and N,N-diisopropylethylamine (50 μL) are added, the mixture is stirred for 7 d at 60° C. and the mixture is purified by HPLC on reversed phase (ACN, water). The residue is dissolved in DCM (1 mL), TFA (1 mL) is added, stirred for 1 h at rt and concentrated in vacuo to give the title compound as trifluoroacetate.

LC (Method 2): $t_R$=0.85 min; Mass spectrum (ESI$^+$): m/z=505 [M+H]$^+$.

Examples 89-93 are prepared in analogy to example 88:

| Example | Structure | $t_R$ | Mass spectrum (ESI+): m/z [M + H]+ | LC Method |
|---|---|---|---|---|
| 89 | 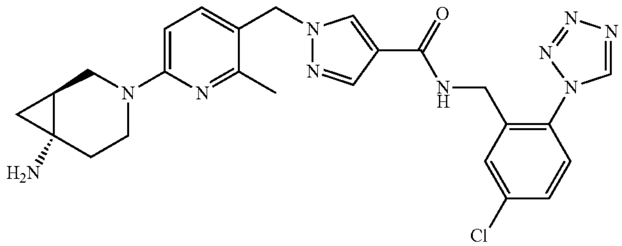 [SMILES: Cc1nc(N2CC[C@@]3(N)C[C@H]3C2)ccc1Cn1cc(C(=O)NCc2cc(Cl)ccc2-n2cnnn2)cn1] | 0.87 | 519 | Method 2 |
| 90 | 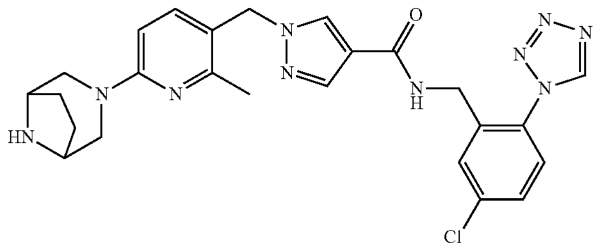 [SMILES: Cc1nc(N2CC3CCC(C2)N3)ccc1Cn1cc(C(=O)NCc2cc(Cl)ccc2-n2cnnn2)cn1] | 0.89 | 519 | Method 2 |
| 91 | 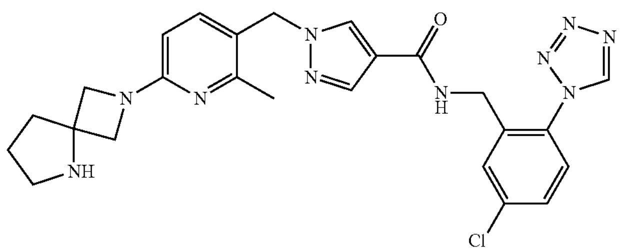 [SMILES: Cc1nc(N2CC3(CCCN3)C2)ccc1Cn1cc(C(=O)NCc2cc(Cl)ccc2-n2cnnn2)cn1] | 0.86 | 519 | Method 2 |
| 92 | 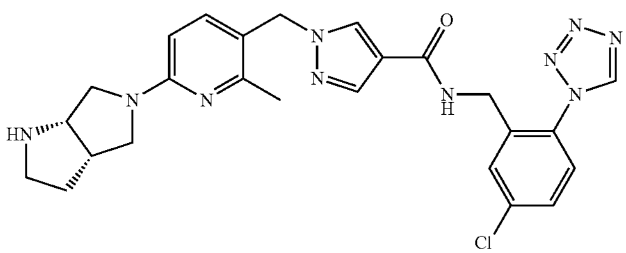 [SMILES: Cc1nc(N2C[C@@H]3CCN[C@@H]3C2)ccc1Cn1cc(C(=O)NCc2cc(Cl)ccc2-n2cnnn2)cn1] | 0.88 | 519 | Method 2 |
| 93 | 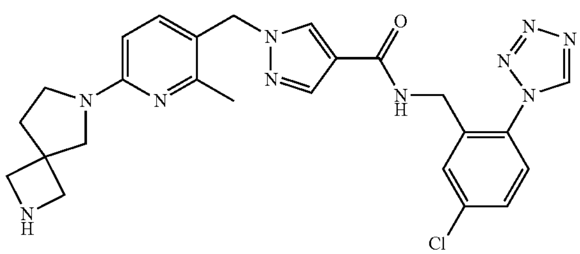 [SMILES: Cc1nc(N2CCC3(CNC3)C2)ccc1Cn1cc(C(=O)NCc2cc(Cl)ccc2-n2cnnn2)cn1] | 0.92 | 519 | Method 2 |

| Example | Name |
|---|---|
| 89 | 1-({6-[(1S,6S)-6-amino-3-azabicyclo[4.1.0]heptan-3-yl]-2-methylpyridin-3-yl}methyl)-N-{[5-chloro-2-(1H-1,2,3,4-tetrazol-1-yl)phenyl]methyl}-1H-pyrazole-4-carboxamide |
| 90 | N-{[5-chloro-2-(1H-1,2,3,4-tetrazol-1-yl)phenyl]methyl}-1-[(6-{3,8-diazabicyclo[3.2.1]octan-3-yl}-2-methylpyridin-3-yl)methyl]-1H-pyrazole-4-carboxamide |
| 91 | N-{[5-chloro-2-(1H-1,2,3,4-tetrazol-1-yl)phenyl]methyl}-1-[(6-{2,5-diazaspiro[3.4]octan-2-yl}-2-methylpyridin-3-yl)methyl]-1H-pyrazole-4-carboxamide |

| Example | Name |
|---|---|
| 92 | 1-({6-[(3aS,6aS)-octahydropyrrolo[3,4-b]pyrrol-5-yl]-2-methylpyridin-3-yl}methyl)-N-{[5-chloro-2-(1H-1,2,3,4-tetrazol-1-yl)phenyl]methyl}-1H-pyrazole-4-carboxamide |
| 93 | N-{[5-chloro-2-(1H-1,2,3,4-tetrazol-1-yl)phenyl]methyl}-1-[(6-{2,6-diazaspiro[3.4]octan-6-yl}-2-methylpyridin-3-yl)methyl]-1H-pyrazole-4-carboxamide |

Example 94

1-[(6-{5-azaspiro[2.3]hexan-5-yl}-2-methylpyridin-3-yl)methyl]-N-{[2-fluoro-6-(1H-1,2,3,4-tetrazol-1-yl)phenyl]methyl}-1H-pyrazole-4-carboxamide

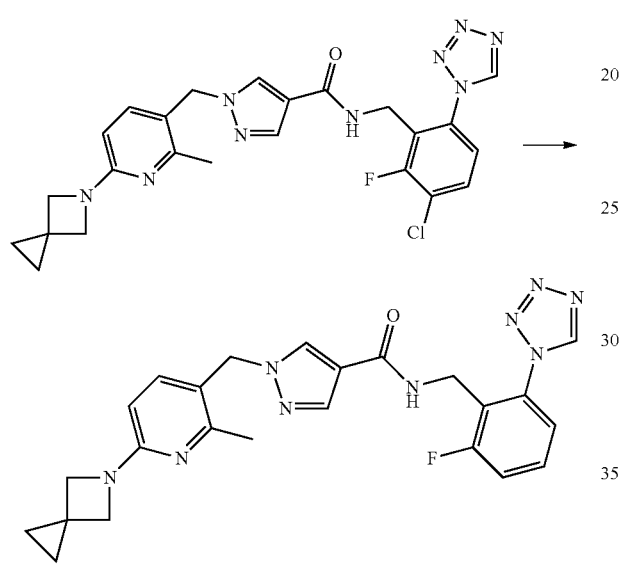

1-[(6-{5-azaspiro[2.3]hexan-5-yl}-2-methylpyridin-3-yl)methyl]-N-{[3-chloro-2-fluoro-6-(1H-1,2,3,4-tetrazol-1-yl)-phenyl]methyl}-1H-pyrazole-4-carboxamide (29 mg) is dissolved in MeOH (3 mL), triethylamine (8 mg) and Pd/C (10%) are added and the mixture is shaked at rt under 50 psi hydrogen pressure. The mixture is filtered and concentrated in vacuo. The residue is purified by HPLC on reversed phase (ACN, water) to give the title compound. LC (Method 2): $t_R$=0.93 min; Mass spectrum (ESI$^+$): m/z=474 [M+H]$^+$.

The invention claimed is:
1. A compound of formula (I)

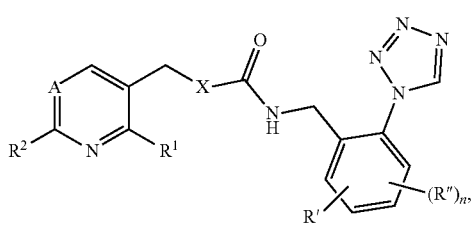

wherein
A is selected from the group consisting of N, CH, C—F, C—Cl, C—Br, C—CN, and C—CH$_3$;

$R^1$ is selected from the group consisting of H and C$_{1-3}$-alkyl optionally substituted with 1 to 3 F;
$R^2$ is selected from the group consisting of
saturated 6-12-membered bicyclic ring systems containing 1 to 3 N atoms as ring members and optionally 1 to 2 ring members selected from the group consisting of C=O, O, S, S=O, and SO$_2$,
provided that the ring systems do not contain any heteroatom-heteroatom bonds between ring members,
wherein said ring systems are attached to the heteroaromatic ring in formula (I) via an N atom, and
wherein said ring systems are optionally substituted with 1 to 6 F, optionally substituted with 1 substituent $R^3$, and optionally substituted with 1 or 2 CH$_3$ groups;
X is selected from the group consisting of
5-membered heteroaryls containing 1 to 3 N atoms, and
9-membered heteroaryls consisting of a 5-membered ring fused to a 6-membered ring and containing 1 to 3 N atoms,
wherein said heteroaryls are attached to the carbonyl group in formula (I) via a C atom of the 5-membered ring and to the X-adjacent CH$_2$ group in formula (I) via a non-adjacent C or N atom of the 5-membered ring, and
wherein said heteroaryls are optionally substituted with 1 substituent $R^4$;
$R^3$ is selected from the group consisting of
C$_{1-3}$-alkyl, C$_{1-3}$-alkylene-OH, C$_{1-3}$-alkylene-O—CH$_3$, —CN, —NH$_2$, —OH, and —O—C$_{1-3}$-alkyl;
$R^4$ is selected from the group consisting of
F, Cl, Br, C$_{1-3}$-alkyl optionally substituted with 1 to 3 F, C$_{1-3}$-alkylene-OH, C$_{1-3}$-alkylene-O—CH$_3$, —CN, —NH$_2$, —OH, —O—C$_{1-3}$-alkyl, and 5-membered heteroaryls containing 1—NH—, —N<, —O—, or —S— ring member and optionally additionally 1 or 2=N— ring members and being optionally substituted with 1 or 2 CH$_3$ groups;
R' is selected from the group consisting of F, Cl, C$_{1-3}$-alkyl optionally substituted with 1 to 3 F, C$_{3-4}$-cycloalkyl, —CN, —O—C$_{1-3}$-alkyl optionally substituted with 1 to 3 F, and —SO$_2$—C$_{1-3}$-alkyl;
R" is at each occurrence independently selected from the group consisting of F, Cl, and CH$_3$; and
n is an integer selected from the group consisting of 0, 1, and 2;
or a salt thereof.
2. The compound according to claim 1, wherein
A is selected from the group consisting of N, CH and C—Br,
or a salt thereof.
3. The compound according to claim 1, wherein
$R^1$ is selected from the group consisting of H and CH$_3$,
or a salt thereof.

4. The compound according to claim 1, wherein
$R^2$ is selected from the group consisting of
saturated 6-10-membered bicyclic ring systems containing 1 to 2 N atoms as ring members and optionally 1 ring member selected from the group consisting of C=O and O,
provided that the ring systems do not contain any heteroatom-heteroatom bonds between ring members,
wherein said ring systems are attached to the heteroaromatic ring in formula (I) via an N atom, and
wherein said ring systems are optionally substituted with 1 or 2 F, optionally substituted with 1 substituent $R^3$, and optionally substituted with 1 $CH_3$ group,
or a salt thereof.

5. The compound according to claim 1, wherein X is selected from the group consisting of

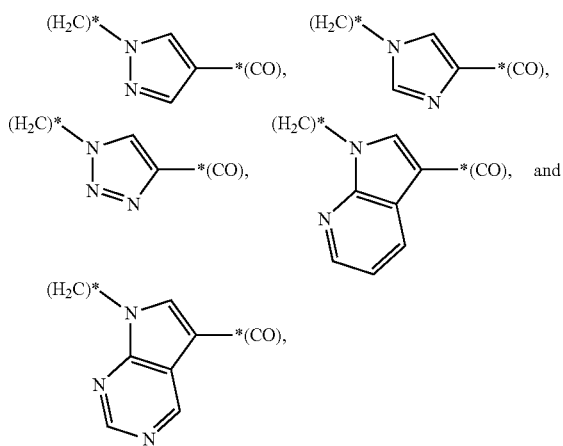

each of which is optionally substituted with 1 substituent $R^4$ and
wherein the bonds with asterisk and brackets indicate the sites of attachment of the C=O group and the X-adjacent $CH_2$ group of formula (I),
or a salt thereof.

6. The compound according to claim 1, wherein $R^3$ is selected from the group consisting of $CH_3$, $CH(CH_3)_2$, $CH_2$—$OCH_3$, $NH_2$, —OH, and —O—$CH_3$,
or a salt thereof.

7. The compound according to claim 1, wherein
$R^4$ is selected from the group consisting of Cl, Br, $C_{1-3}$-alkyl optionally substituted with 1 to 3 F, $C_{1-3}$-alkylene-O—$CH_3$, —$NH_2$, —O—$CH_3$, and 5-membered heteroaryls containing 1—NH— ring member and optionally additionally 1 or 2=N— ring members and being optionally substituted with 1 $CH_3$ group,
or a salt thereof.

8. The compound according to claim 1, wherein R' is selected from the group consisting of F, Cl, $CH_3$, $CHF_2$, $CF_3$, and —CN,
or a salt thereof.

9. A pharmaceutically acceptable salt of a compound according to claim 1.

10. A pharmaceutical composition comprising one or more compounds according to claim 1, or pharmaceutically acceptable salts thereof, optionally together with one or more inert carriers and/or diluents.

11. A pharmaceutical composition comprising one or more compounds according to claim 1, or pharmaceutically acceptable salts thereof, and one or more additional therapeutic agents, optionally together with one or more inert carriers and/or diluents.

12. The pharmaceutical composition according to claim 11, wherein the one or more additional therapeutic agents are selected from the group consisting of antidiabetic agents, agents for the treatment of overweight and/or obesity, agents for the treatment of high blood pressure, heart failure and/or atherosclerosis and agents for the treatment of ocular diseases.

13. A method for the treatment of an ocular disease, comprising administering to a patient in need thereof a pharmaceutically effective amount of one or more compounds according to claim 1, or pharmaceutically acceptable salts thereof, wherein the ocular disease is characterized by unwanted plasma kallikrein activity.

14. The method of claim 13, wherein the ocular disease is selected from the group consisting of diabetic macular edema, age-related macular degeneration and choroidal neovascularization.

* * * * *